(12) United States Patent
Vince et al.

(10) Patent No.: US 9,987,211 B2
(45) Date of Patent: Jun. 5, 2018

(54) SUNLESS TANNING COMPOUNDS AND COMPOSITIONS

(71) Applicant: REGENTS OF THE UNIVERSITY OF MINNESOTA, Minneapolis, MN (US)

(72) Inventors: Robert Vince, Minneapolis, MN (US); Abbas Raza, Minneapolis, MN (US); Christine Dreis, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days. days.

(21) Appl. No.: 14/901,979

(22) PCT Filed: Jul. 2, 2014

(86) PCT No.: PCT/US2014/045319
§ 371 (c)(1),
(2) Date: Dec. 29, 2015

(87) PCT Pub. No.: WO2015/003095
PCT Pub. Date: Jan. 8, 2015

(65) Prior Publication Data
US 2017/0000712 A1    Jan. 5, 2017

Related U.S. Application Data

(60) Provisional application No. 61/842,717, filed on Jul. 3, 2013.

(51) Int. Cl.
| | | |
|---|---|---|
| *A61K 8/49* | (2006.01) |
| *A61K 8/58* | (2006.01) |
| *C07D 239/54* | (2006.01) |
| *A61K 8/04* | (2006.01) |
| *C07F 7/08* | (2006.01) |
| *A61K 8/11* | (2006.01) |
| *A61K 8/02* | (2006.01) |
| *A61Q 19/04* | (2006.01) |
| *C07D 487/16* | (2006.01) |
| *C07D 403/12* | (2006.01) |
| *C07D 403/06* | (2006.01) |
| *C07D 239/52* | (2006.01) |

(52) U.S. Cl.
CPC .......... *A61K 8/4953* (2013.01); *A61K 8/0204* (2013.01); *A61K 8/046* (2013.01); *A61K 8/11* (2013.01); *A61K 8/585* (2013.01); *A61Q 19/04* (2013.01); *C07D 239/52* (2013.01); *C07D 239/54* (2013.01); *C07D 403/06* (2013.01); *C07D 403/12* (2013.01); *C07D 487/16* (2013.01); *C07F 7/0889* (2013.01); *A61K 2800/91* (2013.01)

(58) Field of Classification Search
CPC ...... A61K 2800/91; A61K 8/585; A61K 8/11; A61K 8/046; A61K 8/0204; A61K 8/4953; C07F 7/0889
See application file for complete search history.

(56) References Cited

U.S. PATENT DOCUMENTS

| | | |
|---|---|---|
| 2,949,403 A | 8/1960 | Andreadis et al. |
| 3,177,120 A | 4/1965 | Black et al. |
| 4,136,165 A | 1/1979 | Moller et al. |
| 4,199,576 A | 4/1980 | Reller et al. |
| 4,248,861 A | 2/1981 | Schutt et al. |
| 4,434,154 A | 2/1984 | McShane et al. |
| 4,559,157 A | 12/1985 | Smith et al. |
| 4,608,392 A | 8/1986 | Jacquet et al. |
| 4,708,865 A | 11/1987 | Turner et al. |
| 4,820,508 A | 4/1989 | Wortzman |
| 4,992,478 A | 2/1991 | Geria |
| 5,232,688 A | 8/1993 | Ziegler et al. |
| 5,252,322 A | 10/1993 | Stoner et al. |
| 9,364,406 B2 | 6/2016 | Vince et al. |
| 9,403,778 B2 | 8/2016 | Vince et al. |

FOREIGN PATENT DOCUMENTS

| | | | |
|---|---|---|---|
| DE | 10150412 | * | 4/2003 |
| EP | 0487404 A1 | | 5/1992 |
| WO | 1993004665 A1 | | 3/1993 |
| WO | 2008121850 A2 | | 10/2008 |

OTHER PUBLICATIONS

Berens et al. DE 10150412; published: Apr. 17, 2003, English translation obtained on Dec. 19, 2016.*
Itahara, "NMR and UV Study of 1,1'-(α, ω-Alkanediyl)bis[thymine] and 1,1'-(α, ω-Alkanediyl)bis[uracil]", Bull. Chem. Soc. Jpn, 70, 2239-2247 (1997).
Patent Cooperation Treaty, International Searching Authority, Search Report and Written Opinion for PCT/US2014/045319, 11 pages, dated Sep. 26, 2014.
Rajchel, et al., "Photodimers Derived From 5-Alkyluracils Linked in 1,1'-Positions with Propanone", Polish Journal of Chemistry, 54, 123-128 (1980).

* cited by examiner

*Primary Examiner* — Johann R Richter
*Assistant Examiner* — Genevieve S Alley
(74) *Attorney, Agent, or Firm* — Viksnins Harris Padys Malen LLP

(57) ABSTRACT

The invention provides sunless tanning compositions comprising a compounds of formula (I): or a salt thereof as described herein as well as methods for tanning mammalian skin by contacting the skin with the compounds of formula (I) or compositions comprising compounds of formula (I).

10 Claims, 2 Drawing Sheets

SUNLESS TANNING COMPOUNDS AND COMPOSITIONS

RELATED APPLICATIONS

This application claims priority to U.S. Provisional Application No. 61/842,717 that was filed Jul. 3, 2013. The entire content of this provisional application is hereby incorporated herein by reference.

BACKGROUND OF THE INVENTION

The sun's rays are known to produce ultraviolet radiation, such as sunburn that can have detrimental effects on the skin. Excessive exposure can lead to skin wrinkling, age spots, and even skin cancer. Skin cancer is the most common cancer diagnosed in the United States and the incidence of skin cancer continues to rise. Epidemiological studies have documented that extensive sun exposure increases the risk of developing non-melanoma skin cancer. Photo-protection is the primary preventative health strategy and sunscreens are one of the most important forms of photoprotection.

As people become more aware of the harmful effects of the sun, products such as sunless tanning products or self-tanning products are gaining popularity. These products typically employ a sunless tanning agent, such as dihydroxyacetone to impart color onto the skin that provides the impression of a tan produced by exposure to the sun. Many individuals have a skin complexion which does not tan readily on exposure to sunlight. Others achieve a tan only with great discomfort and possibly adverse effects to the skin due to exposure to sun's rays, e.g., sunburn. Yet, attainment of a tan is highly desired by many individuals for cosmetic and other reasons, especially if this can be accomplished effectively without the usual exposure to the sun, i.e., through skin-tanning agents.

In other instances, individuals who tan with difficulty may desire to enhance or extend the life of a naturally acquired tan without re-exposure to the sun. Also, a suntan may be desired when weather conditions do not permit the sun exposure necessary to acquire a tan. Acquisition of a natural tan by exposure to the sun may be almost impossible for those very light skin persons who tend to burn rather than tan, In addition, the deleterious effects of excessive exposure to sunlight are becoming more generally recognized.

It is known that an artificial tan can be achieved by applying skin-tanning agents to the human skin in a suitable vehicle or base. Examples of known skin-tanning agents include hydroxyaldehydes, such as dihydroxyacetone, (U.S. Pat. No. 2,949,403 and U.S. Pat. No. 5,232,688) and imidazole derivatives, such as 4-(hydroxymethylimidazole) (U.S. Pat. No. 5,252,322).

Dihydroxyacetone is reported to react with skin proteins and amino acids to elicit its skin coloring effect and many compositions using dihydroxyacetone as an active ingredient have been reported including topical composition further containing various dyes, such as catch powder, dogwood powder and walnut powder which are intended to offset the undesirable orange cast or hue which results from the use of dihydroxyacetone on fair skinned humans (U.S. Pat. No. 4,708,865). Other dihydroxyacetone compositions contain sunscreen compounds, such as octyl dimethyl PABA (U.S. Pat. No. 4,434,154 and U.S. Pat. No. 3,177,120). Further, dihydroxyacetone has been formulated into oil-in-water emulsions, into preparations containing up to 50% alcohol which tend to dry the skin, and into "creamy bases", such as are found in hand and face lotions and creams. U.S. Pat. No. 5,232,688 discloses compositions for self-tanning of skin which include an alpha-hydroxy substituted ketone or aldehyde, such as dihydroxyacetone or erythrulose, a polyacrylamide, and a pharmaceutically-acceptable carrier.

There is a need for further sunless tanning agents and compositions comprising such agents.

SUMMARY OF THE INVENTION

In an aspect of the invention there is provided a sunless tanning composition comprising a a compound of formula I:

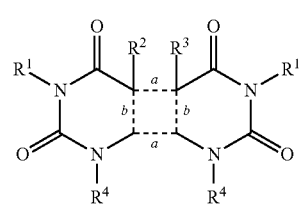

wherein:

each $R^1$ is independently H, $(C_1-C_6)$alkyl, $(C_3-C_7)$carbocycle or $R_aC(=O)—$, and the two $R^4$ groups together form a $—(C_3-C_8)$alkyl- group, a $—(C_2-C_6)$alkyl-Y—$(C_2-C_6)$alkyl- group or a $—(C_1-C_6)$alkyl-Y'—$(C_1-C_6)$alkyl- group; or each $R^4$ is independently H, $(C_1-C_6)$alkyl, $(C_3-C_7)$carbocycle or $R_aC(=O)—$, and the two $R^1$ groups together form a $—(C_3-C_8)$alkyl- group, a $—(C_2-C_6)$alkyl-Y—$(C_2-C_6)$alkyl- group or a $—(C_1-C_6)$alkyl-Y'—$(C_1-C_6)$alkyl- group; or the two $R^4$ groups together form a $—(C_3-C_8)$alkyl- group, a $—(C_2-C_6)$alkyl-Y—$(C_2-C_6)$alkyl group or a $—(C_1-C_6)$alkyl-Y'—$(C_1-C_6)$alkyl- group and the two $R^1$ groups together form a $—(C_3-C_8)$alkyl- group, a $—(C_2-C_6)$alkyl-Y—$(C_2-C_6)$alkyl- group or a $—(C_1-C_6)$alkyl-Y'—$(C_1-C_6)$alkyl-group;

the dashed bonds labeled "a" are absent and the dashed bonds labeled "b" are double bonds; or all the dashed bonds are single bonds;

$R^2$ is H, $(C_1-C_6)$alkyl or aryl, wherein aryl is optionally substituted with one or more $Z^1$ groups;

$R^3$ is H, $(C_1-C_6)$alkyl or aryl, wherein aryl is optionally substituted with one or more $Z^1$ groups;

Y is O, S, NH, $NR_c$, P, $P(=O)$ or POH;

Y' is $Si(R_b)_2$ or $—Si(R_b)_2—O—Si(R_b)_2—$;

each $R_a$ is independently $(C_1-C_6)$alkyl, $(C_3-C_7)$carbocycle or aryl, wherein aryl is optionally substituted with one or more $Z^1$ groups;

each $R_b$ is independently $(C_1-C_6)$alkyl, $(C_3-C_7)$carbocycle or aryl, wherein aryl is optionally substituted with one or more $Z^1$ groups;

each $R_c$ is independently $R_g$ or a $C_1-C_{18}$ saturated or unsaturated carbon chain that is optionally substituted with one or more groups independently selected from oxo $(=O)$, hydroxy, mercapto, $(C_1-C_6)$alkoxy, $(C_1-C_6)$alkoxycarbonyl, $(C_1-C_6)$alkanoyloxy, $NR_dR_e$, carboxy, and aryl, wherein any aryl of $R_c$ is optionally substituted with one or more $R_f$;

each $R_d$ and $R_e$ is independently selected from H, $(C_1-C_6)$alkyl, $(C_1-C_6)$alkanoyl, phenyl, benzyl, and $R_g$;

each $R_f$ is independently selected from $(C_1-C_6)$alkyl, $(C_1-C_6)$alkoxy, $(C_1-C_6)$alkoxycarbonyl, $(C_1-C_6)$alkanoyloxy, $—C(=O)$-phenyl, and $—C(=O)CH_2C(=O)$-phenyl, wherein any phenyl is optionally substituted with one or more groups independently selected from $(C_1-C_6)$alkyl, —$SO_3H$, and $(C_1-C_6)$alkoxy;

each $R_g$ is

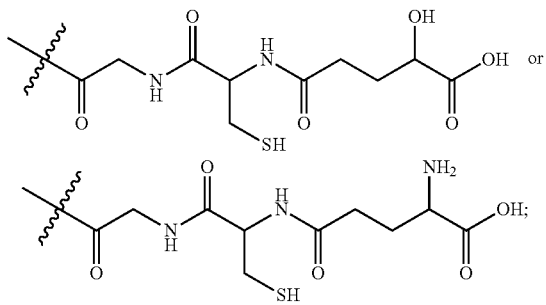

each $Z^1$ is independently selected from $(C_1-C_6)$alkyl, halogen, —CN, —$OR_{n1}$, —$NR_{q1}R_{r1}$, —$NR_{n1}COR_{p1}$, —$NR_{n1}CO_2R_{p1}$, $NO_2$, —$C(O)R_{n1}$, —$C(O)OR_{n1}$ and —$C(O)NR_{q1}R_{r1}$, wherein any $(C_1-C_6)$alkyl of $Z^1$ is optionally substituted with one or more (e.g. 1, 2, 3, 4, 5 or 6) halogen;

each $R_{n1}$ is independently selected from H and $(C_1-C_6)$alkyl, wherein any $(C_1-C_6)$alkyl of $R_{n1}$ is optionally substituted with one or more (e.g. 1, 2, 3, 4, 5 or 6) halogen;

each $R_{p1}$ is independently $(C_1-C_6)$alkyl; and $R_{q1}$ and $R_{r1}$ are each independently selected from H and $(C_1-C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine;

or a salt thereof.

In another aspect, there is provided a sunless tanning composition comprising a compound of formula II:

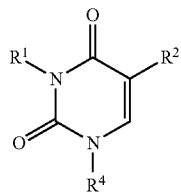

or a pharmaceutically acceptable salt thereof, and a pharmaceutically acceptable carrier,
wherein:
$R^1$ is H, $(C_1-C_6)$alkyl, $(C_3-C_7)$carbocycle or $R_aC(=O)$—;
$R^2$ is H, $(C_1-C_6)$alkyl or aryl, wherein aryl is optionally substituted with one or more (e.g. 1, 2, 3, 4 or 5) $Z^1$ groups;
$R^4$ is H, $(C_1-C_{10})$alkyl, $(C_3-C_7)$carbocycle or $R_aC(=O)$—;
$R_a$ is or $(C_1-C_6)$alkyl, $(C_3-C_7)$carbocycle or aryl, wherein aryl is optionally substituted with one or more (e.g. 1, 2, 3, 4 or 5) $Z^1$ groups;
each $Z^1$ is independently selected from $(C_1-C_6)$alkyl, halogen, —CN, —$OR_{n1}$, —$NR_{q1}R_{r1}$, —$NR_{n1}COR_{p1}$, —$NR_{n1}CO_2R_{p1}$, $NO_2$, —$C(O)R_{n1}$, —$C(O)OR_{n1}$ and —$C(O)NR_{q1}R_{r1}$, wherein any $(C_1-C_6)$alkyl of $Z^1$ is optionally substituted with one or more (e.g. 1, 2, 3, 4, 5 or 6) halogen;
each $R_{n1}$ is independently selected from H and $(C_1-C_6)$alkyl, wherein any $(C_1-C_6)$alkyl of $R_{n1}$ is optionally substituted with one or more (e.g. 1, 2, 3, 4, 5 or 6) halogen;

each $R_{p1}$ is independently $(C_1-C_6)$alkyl; and
$R_{q1}$ and $R_{r1}$ are each independently selected from H and $(C_1-C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine.

In another aspect, there is provided a sunless tanning composition comprising a compound of formula III:

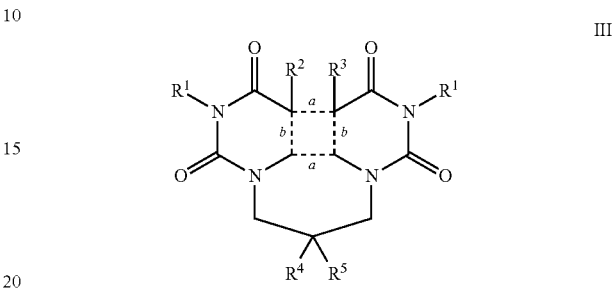

wherein:
each $R^1$ is independently H, $(C_1-C_6)$alkyl, $(C_3-C_7)$carbocycle or $R_aC(=O)$; or the two $R^1$ groups together form a —$(C_3-C_8)$alkyl- group, a —$(C_2-C_6)$alkyl-Y—$(C_2-C_6)$alkyl- group or a —$(C_1-C_6)$alkyl-Y'—$(C_1-C_6)$alkyl- group; or
the dashed bonds labeled "a" are absent and the dashed bonds labeled "b" are double bonds; or all the dashed bonds are single bonds;
$R^2$ is H, $(C_1-C_6)$alkyl or aryl, wherein aryl is optionally substituted with one or more (e.g. 1, 2, 3, 4 or 5) $Z^1$ groups;
$R^3$ is H, $(C_1-C_6)$alkyl or aryl, wherein aryl is optionally substituted with one or more (e.g. 1, 2, 3, 4 or 5) $Z^1$ groups;
$R^4$ is hydroxy, carboxy, $(C_1-C_6)$alkoxycarbonyl, —$OPO_3H_2$, —$OR_c$, or —$NR_dR_e$; and $R^5$ is H; or $R^4$ and $R^5$ taken together are oxo;
Y is O, S, NH, P, P(=O) or POH;
Y' is $Si(R_b)_2$ or —$Si(R_b)_2$—O—$Si(R_b)_2$—;
each $R_a$ is independently $(C_1-C_6)$alkyl, $(C_3-C_7)$carbocycle or aryl, wherein aryl is optionally substituted with one or more (e.g. 1, 2, 3, 4 or 5) $Z^1$ groups;
each $R_b$ is independently $(C_1-C_6)$alkyl, $(C_3-C_7)$carbocycle or aryl, wherein aryl is optionally substituted with one or more (e.g. 1, 2, 3, 4 or 5) $Z^1$ groups;
$R_c$ is $R_f$ or a $C_1-C_{20}$ saturated or $C_2-C_{20}$ unsaturated carbon chain that is optionally substituted with one or more groups independently selected from oxo (=O), hydroxy, mercapto, $(C_1-C_6)$alkoxy, $(C_1-C_6)$alkoxycarbonyl, $(C_1-C_6)$alkanoyloxy, $NR_dR_e$, carboxy, and aryl, wherein aryl is optionally substituted with one or more (e.g. 1, 2, 3, 4 or 5) $Z^1$ groups;
$R_d$ is H, $(C_1-C_6)$alkyl, or $(C_1-C_6)$alkanoyl;
$R_e$ is H or a $C_1-C_{20}$ saturated or $C_2-C_{20}$ unsaturated carbon chain that is optionally substituted with one or more groups independently selected from oxo (=O), hydroxy, mercapto, $(C_1-C_6)$alkoxy, $(C_1-C_6)$alkoxycarbonyl, $(C_1-C_6)$alkanoyloxy, $NR_dR_e$, carboxy, and aryl, wherein aryl is optionally substituted with one or more (e.g. 1, 2, 3, 4 or 5) $Z^1$ groups;
each $R_f$ is:

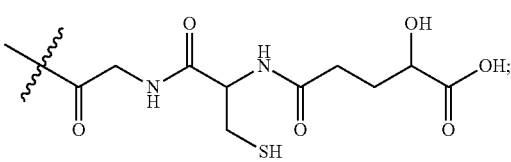 [SMILES: *C(=O)CNC(=O)C(CS)NC(=O)CCC(O)C(=O)O]

each $Z^1$ is independently selected from $(C_1-C_6)$alkyl, halogen, —CN, —OR$_{n1}$, —NR$_{q1}$R$_{r1}$, —NR$_{n1}$COR$_{p1}$, —NR$_{n1}$CO$_2$R$_{p1}$, NO$_2$, —C(O)R$_{n1}$, —C(O)OR$_{n1}$ and —C(O)NR$_{q1}$R$_{r1}$, wherein any $(C_1-C_6)$alkyl of $Z^1$ is optionally substituted with one or more (e.g. 1, 2, 3, 4, 5 or 6) halogen;

each R$_{n1}$ is independently selected from H and $(C_1-C_6)$ alkyl, wherein any $(C_1-C_6)$alkyl of R$_{n1}$ is optionally substituted with one or more (e.g. 1, 2, 3, 4, 5 or 6) halogen; each R$_{p1}$ is independently $(C_1-C_6)$alkyl; and R$_{q1}$ and R$_{r1}$ are each independently selected from H and $(C_1-C_6)$alkyl or R$_{q1}$ and R$_{r1}$ together with the nitrogen to which they are attached form a piperidine, pyrrolidine, morpholine, azetidine, thiomorpholine, piperazine or 4-methylpiperazine;

or a salt thereof.

In another aspect of the invention, there is provided a composition comprising a compound of formula I, II or III for use as a sunless tanning agent.

In another aspect of the invention, there is provided a method of tanning mammalian skin comprising contacting the skin with an effective amount of a compound of formula I, II or III, or a composition comprising said compound.

In another aspect of the invention, there is provided a method of providing an artificial tan to mammalian skin comprising administering to said mammal an effective amount of a compound of formula I, II or III, or a composition comprising said compound.

In another aspect of the invention, there is provided a method of coloring mammalian skin, comprising administering to said mammal an effective amount of a compound of formula I, II or III, or a composition comprising said compound.

In another aspect of the invention, there is provided a method of stimulating pigmentation in mammalian skin, comprising administering to said mammal an effective amount of a compound of formula I, II or III, or a composition comprising said compound.

In another aspect of the invention, there is provided a method of stimulating, or increasing, the production of melanin in melanocytes, comprising contacting said melanocytes with an effective amount of a compound of formula I, II or III, or a composition comprising said compound.

DETAILED DESCRIPTION

Figure 1:
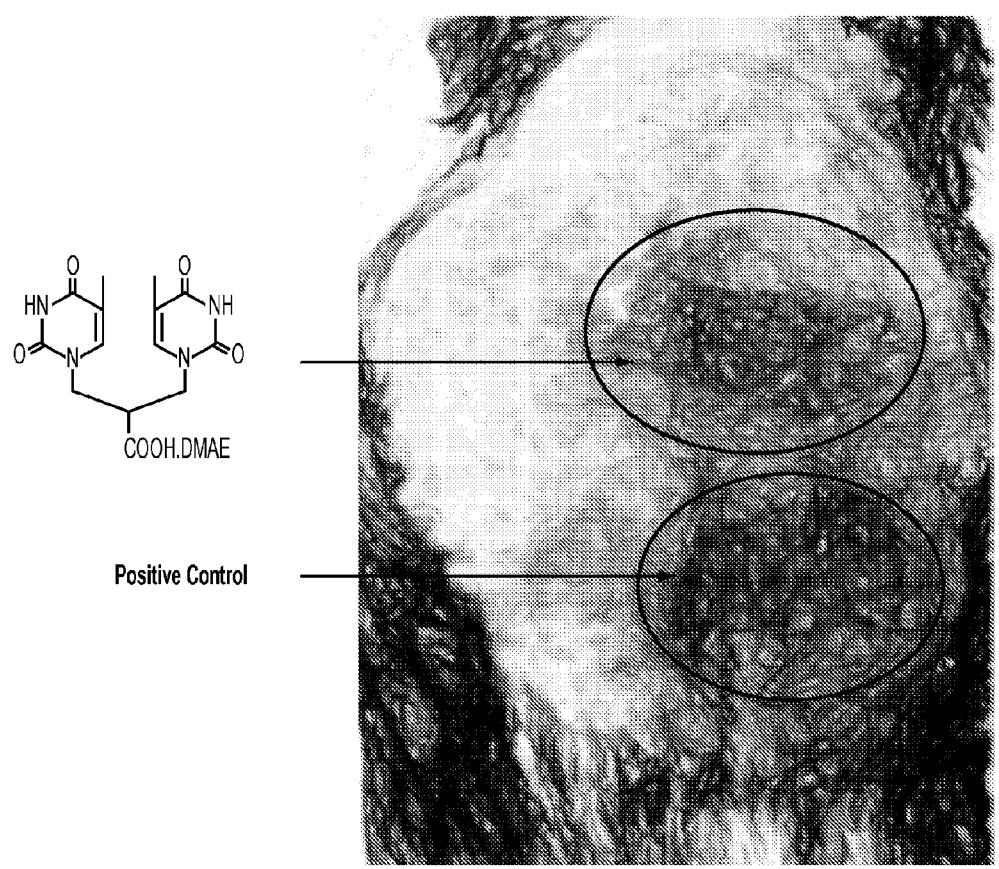
FIG. 1. Application on guinea pig skin of 0.025 mL of 600 µM compound 117 and positive control Thymidine dinucleotide 5'-phosphate twice daily for five consecutive days, a natural DNA component, both demonstrated marked melanin stimulation by day 15 relative to surrounding untreated skin.
Figure 2:
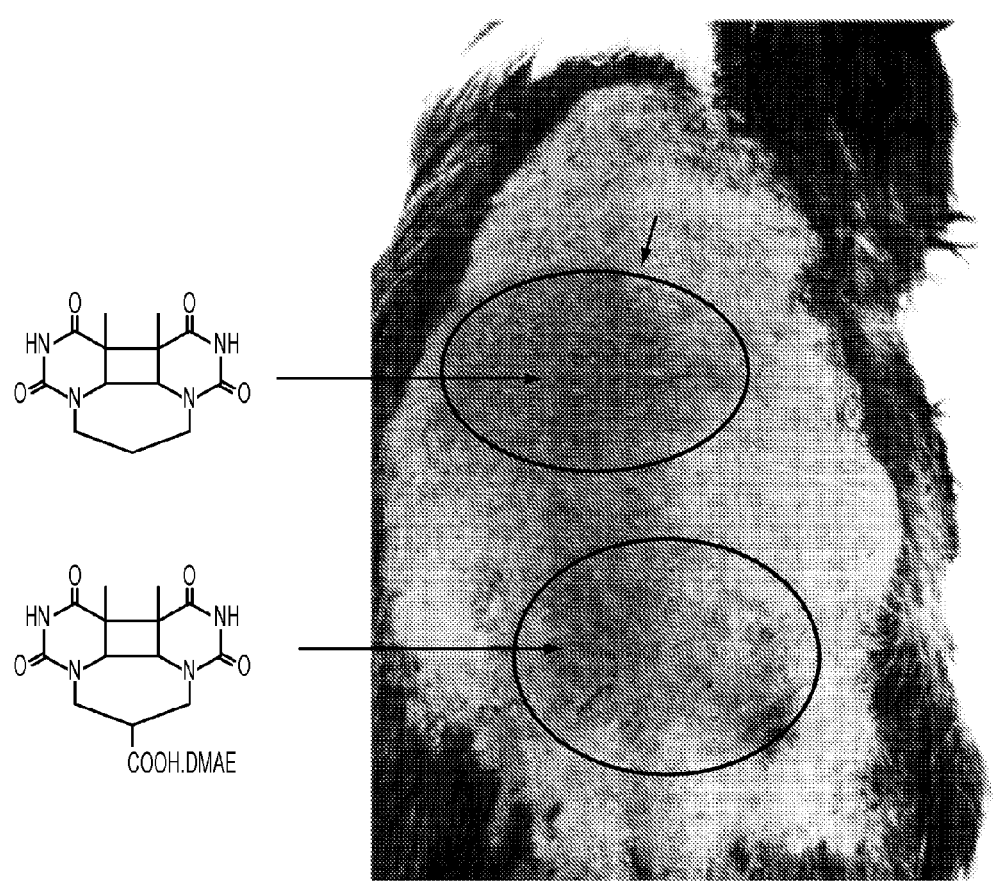
FIG. 2. Application on guinea pig skin of 0.025 mL of 300 µM compounds 10 and 123 twice daily for five consecutive days demonstrated marked melanin stimulation by day 8 relative to surrounding untreated skin.

The following definitions are used, unless otherwise described.

The term "alkyl" as used herein refers to straight and branched hydrocarbon groups. Reference to an individual radical such as propyl embraces only the straight chain radical, a branched chain isomer such as isopropyl being specifically referred to.

The term "halo" or "halogen" as used herein refers to fluoro, chloro, bromo and iodo.

The term "carbocycle" or "carbocyclyl" refers to a single saturated (i.e., cycloalkyl) or a single partially unsaturated (e.g., cycloalkenyl, cycloalkadienyl, etc.) ring having 3 to 7 carbon atoms (i.e. $(C_3-C_7)$carbocycle). The term "carbocycle" or "carbocyclyl" also includes multiple condensed ring systems (e.g. ring systems comprising 2, 3 or 4 carbocyclic rings). Accordingly, carbocycle includes multicyclic carbocycles having 7 to 12 carbon atoms as a bicycle, and up to about 20 carbon atoms as a polycycle. Multicyclic carbocycles can be connected to each other via a single carbon atom to form a spiro connection (e.g. spiropentane, spiro[4,5]decane, spiro[4.5]decane, etc.), via two adjacent carbon atoms to form a fused connection such as a bicyclo [4,5], [5,5], [5,6] or [6,6] system, or 9 or 10 ring atoms arranged as a bicyclo [5,6] or [6,6] system (e.g. decahydronaphthalene, norsabinane, norcarane) or via two non-adjacent carbon atoms to form a bridged connection (e.g. norbornane, bicyclo[2.2.2]octane, etc.). The "carbocycle" or "carbocyclyl" may also be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl and cycloheptyl.

The term "aryl" as used herein refers to a single aromatic ring or a multiple condensed ring system. For example, an aryl group can have 6 to 20 carbon atoms, 6 to 14 carbon atoms, or 6 to 12 carbon atoms. Aryl includes a phenyl radical. Aryl also includes multiple condensed ring systems (e.g. ring systems comprising 2, 3 or 4 rings) having about 9 to 20 carbon atoms in which at least one ring is aromatic. Such multiple condensed ring systems may be optionally substituted with one or more (e.g. 1, 2 or 3) oxo groups on any carbocycle portion of the multiple condensed ring system. It is to be understood that the point of attachment of a multiple condensed ring system, as defined above, can be at any position of the ring system including an aryl or a carbocycle portion of the ring. Typical aryl groups include, but are not limited to, phenyl, indenyl, naphthyl, 1, 2, 3, 4-tetrahydronaphthyl, anthracenyl, and the like.

The term "effective amount" as used herein refers to the amount of the compound or composition that causes skin to darken or tan or otherwise cause a color change in skin.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

Specific values listed below for radicals, substituents, and ranges, are for illustration only; they do not exclude other defined values or other values within defined ranges for the radicals and substituents. Specific values listed are values for compounds of formula I and II as well as all sub-formulas of formula I (e.g. formulas Ia, Ib Ic, Id, Ie, If etc.).

It has been determined that the compounds of formula I, II and III cause a darkening of skin. Accordingly, the invention provides a method for tanning mammalian skin comprising contacting the skin with an effective amount of a compound of formula I, II or III or a composition containing such compound. In another aspect, there is provided a method of providing an artificial tan to mammalian skin comprising contacting the skin with an effective amount of a compound of formula I, II or III or a composition containing such compound. In a particular embodiment, the composition is sprayed on to the subject in a tanning booth. In another aspect, there is provided a method of coloring mammalian skin, comprising contacting the skin with an effective amount of a compound of formula I, II or III or a composition containing such compound. In another aspect of the invention, there is provided a method of stimulating pigmentation in mammalian skin, comprising contacting the skin with an effective amount of a compound of formula I, II or III, or a composition comprising said compound. In another aspect of the invention, there is provided a method of stimulating the production of melanin in melanocytes, comprising contacting said melanocytes with an effective amount of a compound of formula I, II or III, or a composition comprising said compound. In particular embodiments, the foregoing methods involve applying the compounds and compositions topically to human skin. In particular embodiments, the foregoing methods involve applying the compounds and compositions topically to human skin in an aerosol formulation. In particular embodiments, the foregoing methods involve administering the compounds and compositions orally.

The ability of a compound or composition of the invention to darken animal skin may be determined using pharmacological models which are well known to the art. For example, compounds 3a, 10, 24a (5%) in cream vehicle was applied topically to guinea pig dorsal skin which was observed for darkening over the course of several days or weeks.

A specific group of compounds of formula I used in sunless tanning compositions of the invention are compounds of formula Ia:

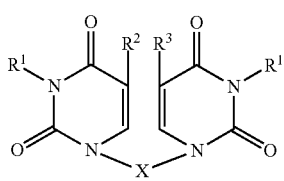

wherein X is a —(C$_3$-C$_5$)alkyl- group or a —(C$_2$-C$_6$)alkyl-Y—(C$_2$-C$_6$)alkyl- group or a —(C$_1$-C$_6$)alkyl-Y'—(C$_1$-C$_6$) alkyl- group; or a salt thereof.

Another specific group of compounds of formula I used in sunless tanning compositions of the invention are compounds of formula Ib:

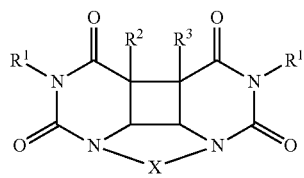

wherein X is a —(C$_3$-C$_8$)alkyl- group or a —(C$_2$-C$_6$)alkyl-Y—(C$_2$-C$_6$)alkyl- group or a —(C$_1$-C$_6$)alkyl-Y'—(C$_1$-C$_6$) alkyl- group; or a salt thereof.

Another specific group of compounds of formula I used in sunless tanning compositions of the invention are compounds of formula Ic:

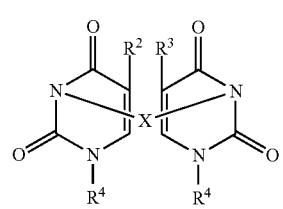

wherein X is a —(C$_3$-C$_8$)alkyl- group or a —(C$_2$-C$_6$)alkyl-Y—(C$_2$-C$_6$)alkyl- group or a —(C$_1$-C$_6$)alkyl-Y'—(C$_1$-C$_6$) alkyl- group; or a salt thereof.

Another specific group of compounds of formula I used in sunless tanning compositions of the invention are compounds of formula Id:

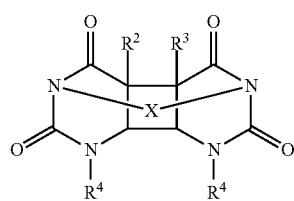

wherein X is a —(C$_3$-C$_8$)alkyl- group or a —(C$_2$-C$_6$)alkyl-Y—(C$_2$-C$_6$)alkyl- group or a —(C$_1$-C$_6$)alkyl-Y'—(C$_1$-C$_6$) alkyl- group; or a salt thereof.

Another specific group of compounds of formula I used in sunless tanning compositions of the invention are compounds of formula Ie:

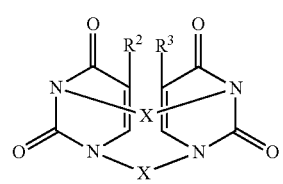

wherein each X is independently a —(C$_3$-C$_8$)alkyl- group or a —(C$_2$-C$_6$)alkyl-Y—(C$_2$-C$_6$)alkyl-group or a —(C$_1$-C$_6$)alkyl-Y'—(C$_1$-C$_6$)alkyl- group; or a salt thereof.

Another specific group of compounds of formula I used in sunless tanning compositions of the invention are compounds of formula If:

wherein each X is independently a —(C$_3$-C$_5$)alkyl- group or a —(C$_2$-C$_6$)alkyl-Y—(C$_2$-C$_6$)alkyl- group or a —(C$_1$-C$_6$)alkyl-Y'—(C$_1$-C$_6$)alkyl- group; or a salt thereof.

Specifically, (C$_1$-C$_6$)alkyl can be methyl, ethyl, propyl, isopropyl, butyl, iso-butyl, sec-butyl, pentyl, 3-pentyl or hexyl.

Specifically, (C$_3$-C$_7$)carbocycle can be cyclopropyl, cyclobutyl, cyclopentyl, cyclohexyl, cycloheptyl and partially unsaturated derivatives thereof.

A specific value for R$^1$ is H.

A specific value for X is —(C$_3$-C$_8$)alkyl- or —(C$_2$-C$_6$)alkyl-Y—(C$_2$-C$_6$)alkyl-.

Another specific value for X is —(C$_2$-C$_6$)alkyl-Y—(C$_2$-C$_6$)alkyl-.

A specific group of compounds of formula I are compounds wherein each R$^1$ is independently H or (C$_1$-C$_6$)alkyl, and the two R$^4$ groups together form a —(C$_2$-C$_6$)alkyl-Y—(C$_2$-C$_6$)alkyl- group.

A specific group of compounds of formula I are compounds wherein R$^1$ is H and X is —(C$_2$-C$_6$)alkyl-Y—(C$_2$-C$_6$)alkyl-; or R$^1$ is (C$_1$-C$_6$)alkyl, (C$_3$-C$_7$)carbocycle, aryl or R$_a$C(=O)—; and X is —(C$_3$-C$_8$)alkyl- or —(C$_2$-C$_6$)alkyl-Y—(C$_2$-C$_6$)alkyl.

A specific value for Y is NH.

A specific group of compounds of formula I are compounds wherein R$^2$ and R$^3$ are each independently (C$_1$-C$_6$)alkyl.

A specific group of compounds of formula I are compounds wherein R$^2$ and R$^3$ are each methyl.

A specific compound of formula I used in sunless tanning compositions of the invention is:

or a salt thereof.

In one embodiment of the invention the compounds of formula I are other than:

In another embodiment of the invention the compounds of formula I are other than:

wherein each R$^{2a}$ is methyl or each R$^{2a}$ is ethyl; and n is 3-6.

A specific group of compounds used in sunless tanning compositions of the invention are compounds of formula I wherein:

each R$^1$ is independently H, (C$_1$-C$_6$)alkyl, (C$_3$-C$_7$)carbocycle or R$_a$C(=O)—, and the two R$^4$ groups together form a —(C$_3$-C$_8$)alkyl- group, a —(C$_2$-C$_6$)alkyl-Y—(C$_2$-C$_6$)alkyl- group or a —(C$_1$-C$_6$)alkyl-Y'—(C$_1$-C$_6$)alkyl- group; or each R$^4$ is independently H, (C$_1$-C$_6$)alkyl, (C$_3$-C$_7$)carbocycle or R$_a$C(=O)—, and the two R$^1$ groups together form a —(C$_3$-C$_8$)alkyl- group, a —(C$_2$-C$_6$)alkyl-Y—(C$_2$-C$_6$) alkyl- group or a —(C$_1$-C$_6$)alkyl-Y'—(C$_1$-C$_6$)alkyl- group; or the two R$^4$ groups together form a —(C$_3$-C$_8$)alkyl- group, a —(C$_2$-C$_6$)alkyl-Y—(C$_2$-C$_6$)alkyl group or a —(C$_1$-C$_6$)alkyl-Y'—(C$_1$-C$_6$)alkyl- group and the two R$^1$ groups together form a —(C$_3$-C$_8$)alkyl- group, a —(C$_2$-C$_6$)alkyl-Y—(C$_2$-C$_6$)alkyl- group or a —(C$_1$-C$_6$)alkyl-Y'—(C$_1$-C$_6$) alkyl-group;

the dashed bonds labeled "a" are absent and the dashed bonds labeled "b" are double bonds; or all the dashed bonds are single bonds;

R$^2$ is H, (C$_1$-C$_6$)alkyl or aryl, wherein aryl is optionally substituted with one or more (e.g. 1, 2, 3, 4 or 5) Z$^1$ groups;

R$^3$ is H, (C$_1$-C$_6$)alkyl or aryl, wherein aryl is optionally substituted with one or more (e.g. 1, 2, 3, 4 or 5) Z$^1$ groups;

Y is O, S, NH, P, P(=O) or POH;

Y' is Si(R$_b$)$_2$ or —Si(R$_b$)$_2$—O—Si(R$_b$)$_2$—;

each R$_a$ is independently (C$_1$-C$_6$)alkyl, (C$_3$-C$_7$)carbocycle or aryl, wherein aryl is optionally substituted with one or more (e.g. 1, 2, 3, 4 or 5) Z$^1$ groups;

each R$_b$ is independently (C$_1$-C$_6$)alkyl, (C$_3$-C$_7$)carbocycle or aryl, wherein aryl is optionally substituted with one or more (e.g. 1, 2, 3, 4 or 5) Z$^1$ groups; and each Z$^1$ is independently selected from (C$_1$-C$_6$)alkyl, halogen, —CN, —OR$_{n1}$, —NR$_{q1}$R$_{r1}$, —NR$_{n1}$COR$_{p1}$, —NR$_{n1}$CO$_2$R$_{p1}$, NO$_2$, —C(O)R$_{n1}$, —C(O)OR$_{n1}$ and —C(O)NR$_{q1}$R$_{r1}$, wherein any (C$_1$-C$_6$)alkyl of Z$^1$ is optionally substituted with one or more (e.g. 1, 2, 3, 4, 5 or 6) halogen;

each R$_{n1}$ is independently selected from H and (C$_1$-C$_6$) alkyl, wherein any (C$_1$-C$_6$)alkyl of R$_{n1}$ is optionally substituted with one or more (e.g. 1, 2, 3, 4, 5 or 6) halogen;

each R$_{p1}$ is independently (C$_1$-C$_6$)alkyl; and

R$_{q1}$ and R$_{r1}$ are each independently selected from H and (C$_1$-C$_6$)alkyl or R$_{q1}$ and R$_{r1}$ together with the nitrogen to which they are attached form a piperidine, pyrrolidine, morpholine, azetidine, thiomorpholine, piperazine or 4-methylpiperazine;

and salts thereof.

A specific compound used in sunless tanning compositions of the invention is a compound selected from the group consisting of:

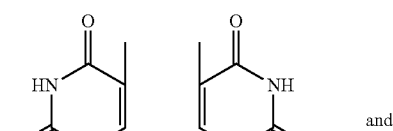

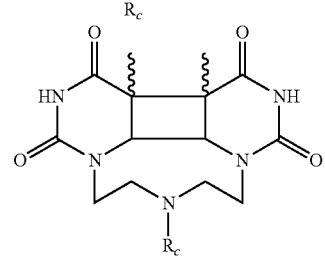

and salts thereof.

A specific R$_c$ is selected from butanoyl, hexadecanoyl, octadecanoyl, benzoyl, 3-phenylprop-2-enoyl, 3-(4-methoxyphenyl)prop-2-enoyl, 3-carboxy-3-hydroxypropanoyl, 2-(N-acetylamino)-3-mercaptopropanoyl, 4-(4-methoxy-3-sulfobenzoyl)benzoyl, 4-(3-(4-methoxyphenyl)-1,3-dioxopropyl)benzoyl, and

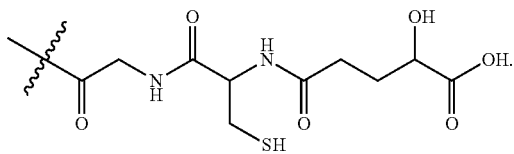 [SMILES: *C(=O)CNC(=O)C(CS)NC(=O)CCC(O)C(=O)O]

A specific compound used in sunless tanning compositions of the invention is a compound selected from the group consisting of:

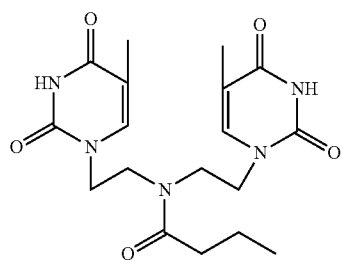

24a

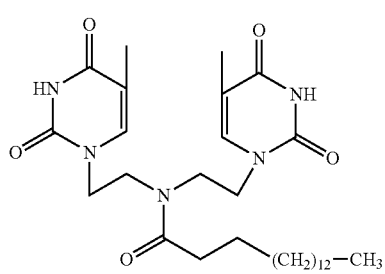

24b

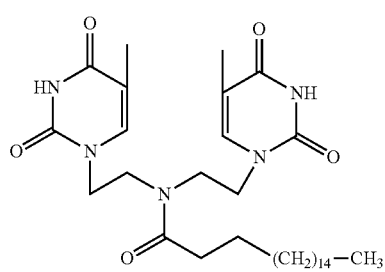

24c

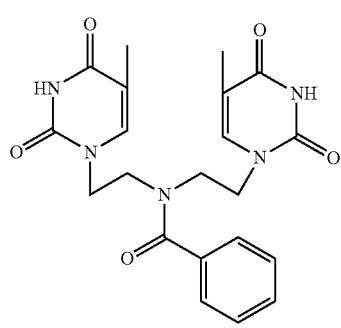

24d

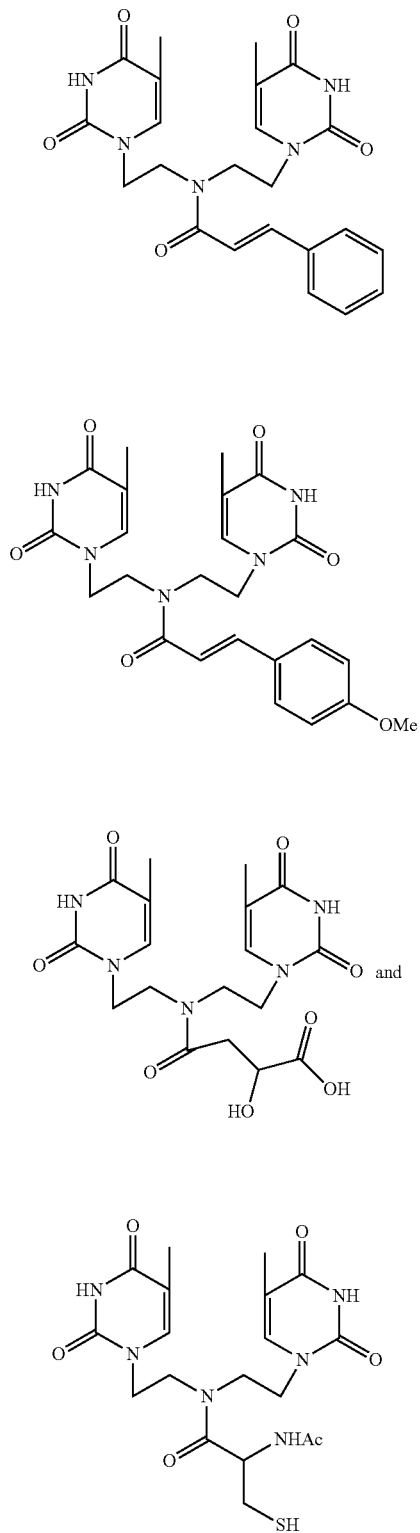
and salts thereof.
A specific compound used in sunless tanning compositions of the invention is a compound selected from the group consisting of:
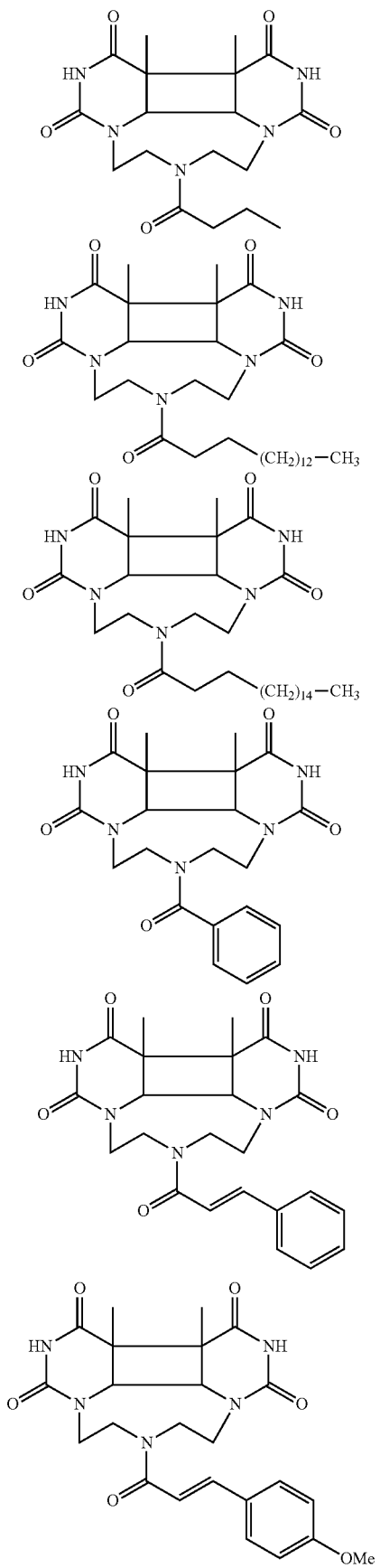

-continued

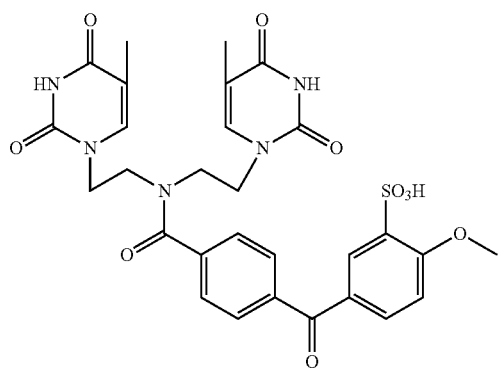

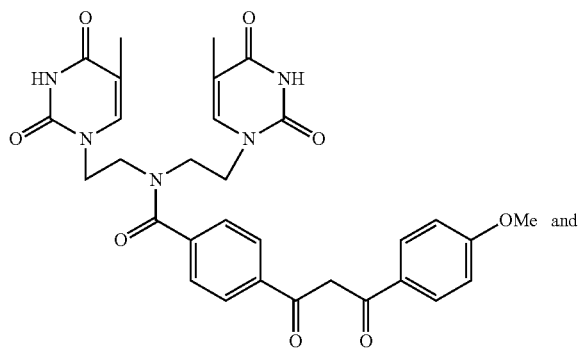

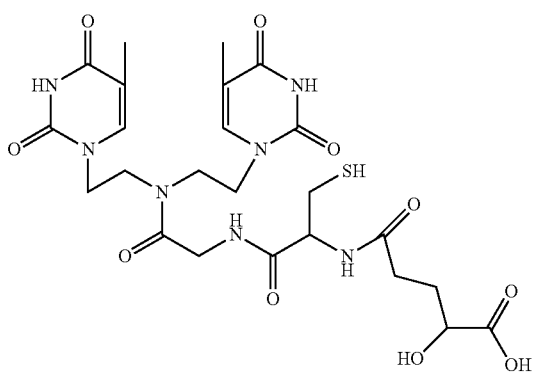

and salts thereof.

Processes for preparing compounds of formula I and II are provided as further embodiments of the invention and are illustrated in Schemes 1 and 2.

Scheme 1

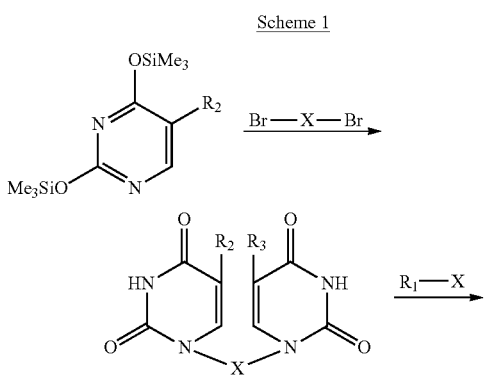

-continued

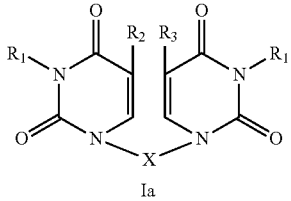

Ia wherein X is —(C$_3$-C$_8$)alkyl- or —(C$_2$-C$_6$)alkyl-Y—(C$_2$-C$_6$)alkyl- or a —(C$_1$-C$_6$)alkyl-Y'—(C$_1$-C$_6$)alkyl-group and all other variables have the values as described herein.

Scheme 2

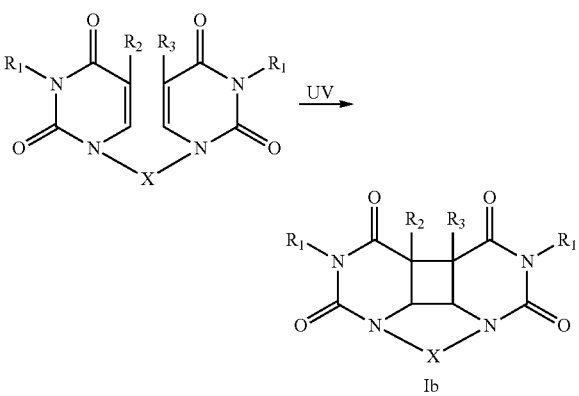

Ib wherein X is —(C$_3$-C$_8$)alkyl- or —(C$_2$-C$_6$)alkyl-Y—(C$_2$-C$_6$)alkyl- or a —(C$_1$-C$_6$)alkyl-Y'—(C$_1$-C$_6$)alkyl-group and all other variables have the values as described herein.

Accordingly, the invention also provides a sunless tanning composition comprising a compound of formula II:

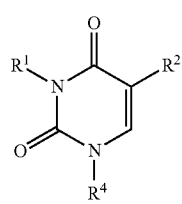

II or a pharmaceutically acceptable salt thereof, and a pharmaceutically acceptable carrier,
wherein:
R$^1$ is H, (C$_1$-C$_6$)alkyl, (C$_3$-C$_7$)carbocycle or R$_a$C(=O)—;
R$^2$ is H, (C$_1$-C$_6$)alkyl or aryl, wherein aryl is optionally substituted with one or more (e.g. 1, 2, 3, 4 or 5) Z$^1$ groups;
R$^4$ is H, (C$_1$-C$_{10}$)alkyl, (C$_3$-C$_7$)carbocycle or R$_a$C(=O)—;
R$_a$ is or (C$_1$-C$_6$)alkyl, (C$_3$-C$_7$)carbocycle or aryl, wherein aryl is optionally substituted with one or more (e.g. 1, 2, 3, 4 or 5) Z$^1$ groups;
each Z$^1$ is independently selected from (C$_1$-C$_6$)alkyl, halogen, —CN, —OR$_{n1}$, —NR$_{q1}$R$_{r1}$, —NR$_{n1}$COR$_{p1}$, —NR$_{n1}$CO$_2$R$_{p1}$, NO$_2$, —C(O)R$_{n1}$, —C(O)OR$_{n1}$ and —C(O)NR$_{q1}$R$_{r1}$, wherein any (C$_1$-C$_6$)alkyl of Z$^1$ is optionally substituted with one or more (e.g. 1, 2, 3, 4, 5 or 6) halogen;

each $R_{n1}$ is independently selected from H and $(C_1$-$C_6)$ alkyl, wherein any $(C_1$-$C_6)$alkyl of $R_{n1}$ is optionally substituted with one or more (e.g. 1, 2, 3, 4, 5 or 6) halogen;

each $R_{p1}$ is independently $(C_1$-$C_6)$alkyl; and $R_{q1}$ and $R_{r1}$ are each independently selected from H and $(C_1$-$C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine.

In another aspect of the invention, sunless tanning compositions of the invention comprise a compound of formula III:

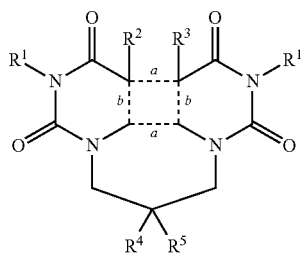

wherein:

each $R^1$ is independently H, $(C_1$-$C_6)$alkyl, $(C_3$-$C_7)$carbocycle or $R_aC(=O)$; or the two $R^1$ groups together form a —$(C_3$-$C_8)$alkyl- group, a —$(C_2$-$C_6)$alkyl-Y—$(C_2$-$C_6)$alkyl- group or a —$(C_1$-$C_6)$alkyl-Y'—$(C_1$-$C_6)$alkyl- group; or the dashed bonds labeled "a" are absent and the dashed bonds labeled "b" are double bonds; or all the dashed bonds are single bonds;

$R^2$ is H, $(C_1$-$C_6)$alkyl or aryl, wherein aryl is optionally substituted with one or more (e.g. 1, 2, 3, 4 or 5) $Z^1$ groups;

$R^3$ is H, $(C_1$-$C_6)$alkyl or aryl, wherein aryl is optionally substituted with one or more (e.g. 1, 2, 3, 4 or 5) $Z^1$ groups;

$R^4$ is hydroxy, carboxy, $(C_1$-$C_6)$alkoxycarbonyl, —$OPO_3H_2$, —$OR_c$, or —$NR_dR_e$; and $R^5$ is H; or $R^4$ and $R^5$ taken together are oxo;

Y is O, S, NH, P, P(=O) or POH;

Y' is $Si(R_b)_2$ or —$Si(R_b)_2$—O—$Si(R_b)_2$—;

each $R_a$ is independently $(C_1$-$C_6)$alkyl, $(C_3$-$C_7)$carbocycle or aryl, wherein aryl is optionally substituted with one or more (e.g. 1, 2, 3, 4 or 5) $Z^1$ groups;

each $R_b$ is independently $(C_1$-$C_6)$alkyl, $(C_3$-$C_7)$carbocycle or aryl, wherein aryl is optionally substituted with one or more (e.g. 1, 2, 3, 4 or 5) $Z^1$ groups;

$R_c$ is $R_f$ or a $C_1$-$C_{20}$ saturated or $C_2$-$C_{20}$ unsaturated carbon chain that is optionally substituted with one or more groups independently selected from oxo (=O), hydroxy, mercapto, $(C_1$-$C_6)$alkoxy, $(C_1$-$C_6)$alkoxycarbonyl, $(C_1$-$C_6)$alkanoyloxy, $NR_dR_e$, carboxy, and aryl, wherein aryl is optionally substituted with one or more (e.g. 1, 2, 3, 4 or 5) $Z^1$ groups;

$R_d$ is H, $(C_1$-$C_6)$alkyl, or $(C_1$-$C_6)$alkanoyl;

$R_e$ is H or a $C_1$-$C_{20}$ saturated or $C_2$-$C_{20}$ unsaturated carbon chain that is optionally substituted with one or more groups independently selected from oxo (=O), hydroxy, mercapto, $(C_1$-$C_6)$alkoxy, $(C_1$-$C_6)$alkoxycarbonyl, $(C_1$-$C_6)$alkanoyloxy, $NR_dR_e$, carboxy, and aryl, wherein aryl is optionally substituted with one or more (e.g. 1, 2, 3, 4 or 5) $Z^1$ groups;

each $R_f$ is:

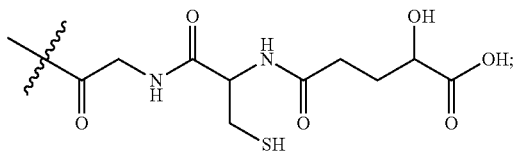 [SMILES: *C(=O)CNC(=O)C(CS)NC(=O)CCC(O)C(=O)O]

each $Z^1$ is independently selected from $(C_1$-$C_6)$alkyl, halogen, —CN, —$OR_{11}$, —$NR_qR_r$, —$NR_{n1}COR_{p1}$, —$NR_{n1}CO_2R_{p1}$, $NO_2$, —$C(O)R_{n1}$, —$C(O)OR_{n1}$ and —$C(O)NR_{q1}R_{r1}$, wherein any $(C_1$-$C_6)$alkyl of $Z^1$ is optionally substituted with one or more (e.g. 1, 2, 3, 4, 5 or 6) halogen;

each $R_{n1}$ is independently selected from H and $(C_1$-$C_6)$ alkyl, wherein any $(C_1$-$C_6)$alkyl of $R_{n1}$ is optionally substituted with one or more (e.g. 1, 2, 3, 4, 5 or 6) halogen;

each $R_{p1}$ is independently $(C_1$-$C_6)$alkyl; and $R_{q1}$ and $R_{r1}$ are each independently selected from H and $(C_1$-$C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine;

or a salt thereof.

A specific group of compounds of formula III are compounds of formula IIIa:

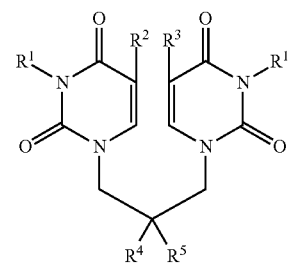

and salts thereof.

A specific group of compounds of formula III are compounds of formula IIIb:

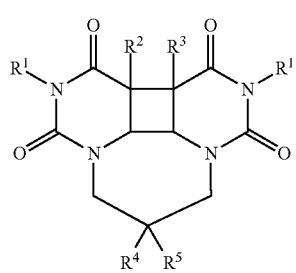

and salts thereof.

A specific value for $R^1$ is independently H or $(C_1$-$C_6)$ alkyl.

A specific value for Y is NH.

A specific value for $R^1$ is H.

Specifically $R^2$ and $R^3$ can each independently be $(C_1$-$C_6)$alkyl.

A specific value for $R^4$ is hydroxyl.

A specific value for $R^4$ is carboxy.

A specific value for $R^4$ is $(C_1$-$C_6)$alkoxycarbonyl.

A specific value for $R^4$ is —OPO$_3$H$_2$.
A specific value for $R^4$ is —OR$_c$.
A specific value for $R^4$ is —NR$_d$R$_e$.

A specific value for $R_c$ is a C$_1$-C$_{20}$ saturated or C$_2$-C$_{20}$ unsaturated alkanoyl group that is optionally substituted with one or more groups independently selected from oxo (=O), hydroxy, mercapto, (C$_1$-C$_6$)alkoxy, (C$_1$-C$_6$)alkoxycarbonyl, (C$_1$-C$_6$)alkanoyloxy, NR$_d$R$_e$, carboxy, and aryl.

A specific value for $R_c$ is a C$_1$-C$_{20}$ saturated or C$_2$-C$_{20}$ unsaturated alkanoyl group that is optionally substituted with one or more groups independently selected from oxo (=O), hydroxy, mercapto, carboxy, and aryl, and R$_f$.

A specific value for $R_c$ is $R_f$.

A specific value for $R_c$ is butanoyl, hexadecanoyl, octadecanoyl, benzoyl, 3-phenylprop-2-enoyl, or 3-(4-methoxyphenyl)prop-2-enoyl.

A specific value for $R_e$ is H or a C$_1$-C$_{20}$ saturated or C$_2$-C$_{20}$ unsaturated alkanoyl group that is optionally substituted with one or more groups independently selected from oxo (=O), hydroxy, mercapto, (C$_1$-C$_6$)alkoxy, (C$_1$-C$_6$)alkoxycarbonyl, (C$_1$-C$_6$)alkanoyloxy, NR$_d$R$_e$, carboxy, and aryl.

A specific value for $R_e$ is a C$_1$-C$_{20}$ saturated or C$_2$-C$_{20}$ unsaturated alkanoyl group that is optionally substituted with one or more groups independently selected from oxo (=O), hydroxy, mercapto, carboxy, and aryl, and R$_f$.

A specific value for $R_e$ is butanoyl, hexadecanoyl, octadecanoyl, benzoyl, 3-phenylprop-2-enoyl, or 3-(4-methoxyphenyl)prop-2-enoyl.

A specific compound is a compound which

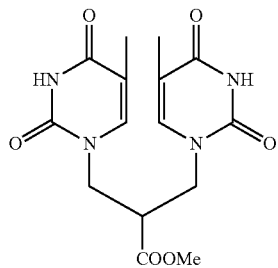

115

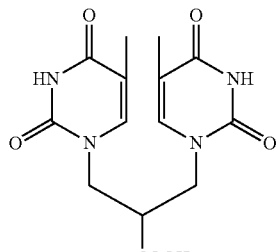

116

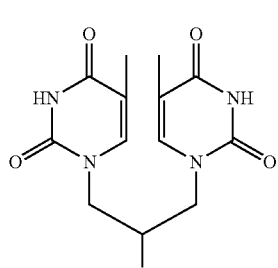

121

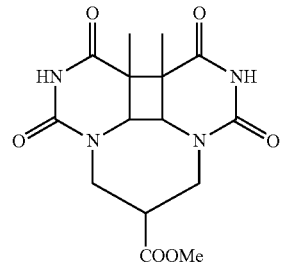

122

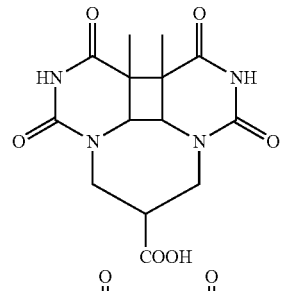

130

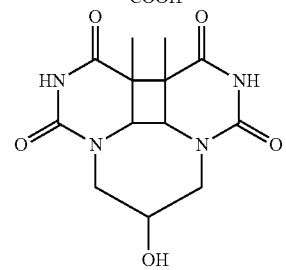

and salts thereof.

A specific compound is a compound which is selected from:

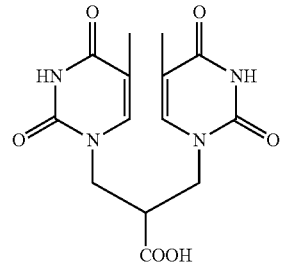

116

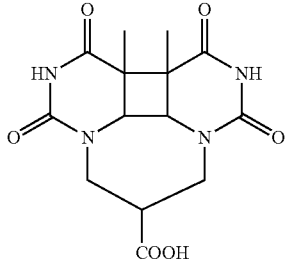

130 and salts thereof. Specific salts include salts with N,N-dimethylaminoethanol or glucosamine.

Processes for preparing compounds of formula I are provided as further embodiments of the invention and are illustrated in Schemes 3 and 4.

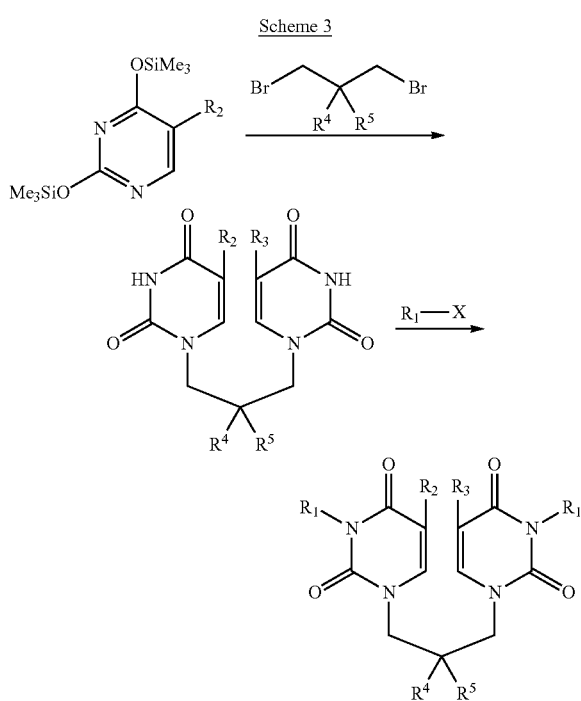

Scheme 3

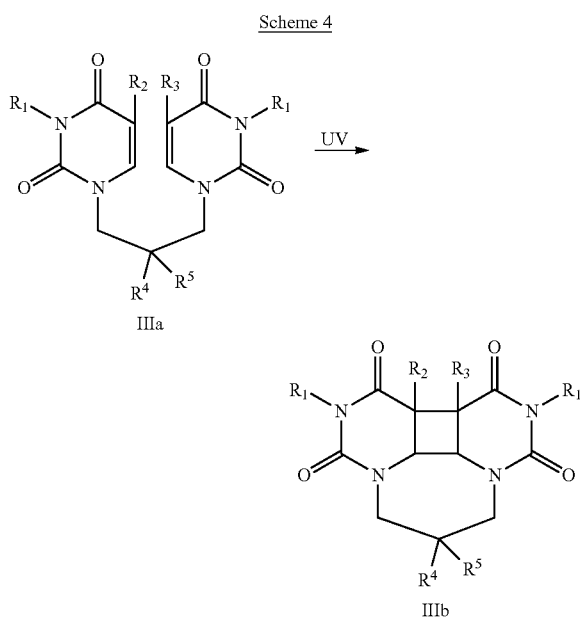

Scheme 4

The invention also provides a sunless tanning composition comprising a mixture of two or more compounds of formula I and/or formula II (as described above), or salts thereof, and a carrier.

The invention also provides processes and intermediates disclosed herein that are useful for preparing compounds of formula II (as described above) or salts thereof.

In cases where compounds are sufficiently basic or acidic, a salt of a compound of the formula can be useful as an intermediate for isolating or purifying a compound of formula I or formula II. Additionally, administration of a compound of formula I or formula II as a pharmaceutically or dermatologically acceptable acid or base salt may be appropriate. Examples of pharmaceutically acceptable salts including dermatologically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts which include dermatologically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I or formula II can be formulated as sunless tanning compositions and administered to a mammalian host, such as a human patient in a variety of forms adapted to the chosen route of administration, i.e., orally or parenterally, by intravenous, intramuscular, topical or subcutaneous routes. It is to be understood that the term pharmaceutically acceptable carrier also includes carriers that are suitable for topical use as described herein below. In one embodiment of the invention the pharmaceutically acceptable carrier is a dermatologically acceptable carrier.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compound may also be administered intravenously or intraperitoneally by infusion or injection. Solutions of the compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In an embodiment it will include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compound in the required amount in the appropriate solvent with various other ingredients enumerated above, as required, followed by filter sterilization. In the case of sterile powders for the preparation of sterile injectable solutions, a particular method of preparation is vacuum drying and the freeze drying techniques, which yield a powder of the active ingredient plus any additional desired ingredient present in the previously sterile-filtered solutions.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, for example, in the range of 6 to 90 mg/kg/day, such as in the range of 15 to 60 mg/kg/day.

The compound may be formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds of formula I or formula II can be formulated as dermatological compositions and applied to a mammalian host, such as a human by a topical route. For topical administration, the present compounds may be applied in pure form, i.e., when they are liquids. However, it will generally be desirable to administer them to the skin as compositions or formulations, in combination with a dermatologically acceptable carrier, which may be a solid carrier or a liquid carrier.

Useful solid carriers include finely divided solids such as talc, clay, microcrystalline cellulose, silica, alumina, cyclodextrins and the like. Useful liquid carriers include water, alcohols or glycols or water-alcohol/glycol blends, in which the present compounds can be dissolved or dispersed at effective levels, optionally with the aid of non-toxic surfactants. Additional carriers include vegetable oils, hydrocarbon oils and waxes, silicone oils, animal and marine fats or oils. Adjuvants such as fragrances and additional antimicrobial agents can be added to the composition to optimize the properties for a given use. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Cosmetic compositions, may contain conventional ingredients known to those of ordinary skill in the art, such as those described in Kirk-Othmer, Encyclopedia of Chemical Technology, Third Edition (1979), Vol. 7, pages 143-176. Specific ingredients, including typical sunscreens, are listed in, for example, the above mentioned Kirk-Othmer Encyclopedia, at pages 153-154. In addition, topical preparations and cosmetic formulations may be prepared as described in U.S. Pat. Nos. 4,199,576, 4,136,165, and 4,248,861. Examples of additional useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The percentage of the components of the compositions and preparations may be varied. In general, a suitable dermatological composition of the invention will typically comprise a compound of formula I or formula II or a mixture thereof in an effective amount and may be between about 0.01-25% of the weight of a dermatological composition. In an embodiment, the amount of the sunless tanning compound in such dermatological compositions is from about 2% to about 12% by weight. In an embodiment, the amount of the sunless tanning compound in such dermatological compositions is about 5% by weight.

The compounds of formula I and formula II and dermatological compositions thereof as described herein can be used in sunscreens or other cosmetic formulations containing compounds that protect skin or DNA in skin from photodamage or repair photodamaged skin or photodamaged DNA in the skin. It is apparent to those of ordinary skill in the art that the compositions or formulations can be in many forms, including, but not limited to, for example, solutions, lotions, oils, sprays, creams, pastes, emulsions, sprays, or aerosols and delivered in a suitable manner.

Compositions of the invention may be formulated as sunscreen or suntan lotion formulations by combining with sun screening agents such as avobenzone, ecamsule, methylanthranilate, oxybenzone, dioxybenzone, sulisobenzone, octinoxate, homosalate, octocrylene and octylsalate. Such compositions may comprise organic UV filters, so-called hydrophilic or lipophilic sun-protection filters, which are effective in the UVA region and/or UVB region and (/or IR and/or VIS region (absorbers). These substances can be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the WO93/04665. Further examples of organic filters are indicated in patent application EP-A 0 487 404. Particularly suitable for a combination are: para-aminobenzoic acid and derivatives thereof: PABA, Ethyl PABA, Ethyl dihydroxypropyl PABA, Ethylhexyl dimethyl PABA, for example marketed by ISP under the name "Escalol 507", Glyceryl PABA, PEG-25 PABA, for example marketed under the name "Uvinul P25" by BASF.

Other UV filter ingredients which may be incorporated in compositions of the invention include:

Salicylates: Homosalate marketed by Merck under the name "Eusolex HMS"; Ethylhexyl salicylate, for example marketed by Symrise under the name "Neo Heliopan OS", Dipropylene glycol salicylate, for example marketed by Scher under the name "Dipsal", TEA salicylate, for example marketed by Symrise under the name "Neo Heliopan TS".

β,β-Diphenylacrylate derivatives: Octocrylene, for example marketed by Merck under the name "Euso-lex® OCR", "Uvinul N539" from BASF, Etocrylene, for example marketed by BASF under the name "Uvinul N35".

Benzophenone derivatives: Benzophenone-1, for example marketed under the name "Uvinul 400"; Benzophenone-2, for example marketed under the name "Uvinul D50"; Benzophenone-3 or Oxybenzone, for example marketed under the name "Uvinul M40"; Benzophenone-4, for example marketed under the name "Uvinul MS40"; Benzophenone-9, for example marketed by BASF under the name "Uvinul DS-49", Benzophenone-5, Benzophenone-6, for example marketed by Norquay under the name "Helisorb 11", Benzophenone-8, for example marketed by American Cyanamid under the name "Spectra-Sorb UV-24", Benzophenone-12 n-hexyl 2-(4-diethylamino-2-hydroxybenzoyl)benzoate or 2-hydroxy-4-methoxybenzophenone, marketed by Merck, Darmstadt, under the name Eusolex® 4360.

Benzylidenecamphor derivatives: 3-Benzylidenecamphor, for example marketed by Chimex under the name "Mexoryl SD", 4-Methylbenzylidenecamphor, for example marketed by Merck under the name "Eusolex 6300", benzylidenecamphorsulfonic acid, for example marketed by Chimex under the name "Mexoryl SL", Camphor benzalkonium methosulfate, for example marketed by Chimex under the name "Mexoryl SO", terephthalylidenedicamphorsulfonic acid, for example marketed by Chimex under the name "Mexoryl SX", Polyacrylamidomethylbenzylidenecamphor marketed by Chimex under the name "Mexoryl SW".

Phenylbenzimidazole derivatives: phenylbenzimidazole-sulfonic acid, for example marketed by Merck under the name "Eusolex 232", disodium phenyl dibenzimidazole tetrasulfonate, for example marketed by Symrise under the name "Neo Heliopan AP".

Phenylbenzotriazole derivatives: Drometrizole trisiloxane, for example marketed by Rhodia Chimie under the name "Silatrizole", Methylenebis(benzotriazolyl)tetramethylbutylphenol in solid form, for example marketed by Fairmount Chemical under the name "MIXXIM BB/100", or in micronized form as an aqueous dispersion, for example marketed by BASF under the name "Tinosorb M".

Triazine derivatives: ethylhexyltriazone, for example marketed under the name "Uvinul T150" by BASF, diethylhexylbutamidotriazone, for example marketed under the name "Uvasorb HEB" by Sigma 3V, 2,4,6-tris(diisobutyl 4'-aminobenzalmalonate)-s-triazine or 2,4,6-tris(biphenyl)-1,3,5-triazine. marketed as Tinosorb A2B by BASF, 2,2'-[6-(4-methoxyphenyl)-1,3,5-triazine-2,4-diyl]bis[5-(2-ethylhexyl)oxy]phenol, marketed as Tinosorb S by BASF, N2,N4-bis[4-[5-(1,1-dimethylpropyl)-2-benzoxazolyl]phenyl]-N-6-(2-ethylhexyl)-1,3,5-triazine-2,4,6-triamine marketed as Uvasorb K 2A by Sigma 3V.

Anthraniline derivatives: Menthyl anthranilate, for example marketed by Symrise under the name "Neo Heliopan MA".

Imidazole derivatives: Ethylhexyldimethoxybenzylidene-dioxoimidazoline propionate.

Benzalmalonate derivatives: polyorganosiloxanes containing functional benzalmalonate groups, such as, for example, polysilicone-15, for example marketed by Hoffmann LaRoche under the name "Parsol SLX".

4,4-Diarylbutadiene derivatives: 1,1-Dicarboxy(2,2'-dim-ethylpropyl)-4,4-diphenylbutadiene.

Benzoxazole derivatives: 2,4-bis[5-(1-dimethylpropyl) benzoxazol-2-yl(4-phenyl) imino]-6-(2-ethylhexyl) imino-1,3,5-triazine, for example marketed by Sigma 3V under the name Uvasorb K2A, and mixtures comprising this.

Suitable organic UV-protecting substances can preferably be selected from: Ethylhexyl salicylate, Phenylbenzimida-zolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid, Disodium phenyldibenzimidazoletetrasulfonate, Methylenebis(benzotriazolyl)tetramethylbutylphenol, Ethylhexyl Triazone, Diethylhexyl Butamido Triazone, Drometrizole trisiloxane, Polysilicone-15,1,1-Dicarboxy(2,2'-dimethylpropyl)-4,4-diphenylbutadiene, 2,4-bis[5-1 (dimethylpropyl)benzoxazol-2-yl(4-phenyl) imino]-6-(2-ethylhexyl)imino-1,3,5-triazine and mixtures thereof. These organic UV filters are generally incorporated into formulations in an amount of 0.01 percent by weight to 20 percent by weight, preferably 1% by weight-10% by weight.

The compositions of the invention may comprise further inorganic UV filters, so-called particulate UV filters. These combinations with particulate UV filters are possible both as powder and also as dispersion or paste. In an embodiment the inorganic UV filter is a titanium dioxide, such as, for example, coated titanium dioxide (for example Eusolex® T-2000, Eusolex® T-AQUA, Eusolex® T-AVO, Eusolex® T-OLEO), a zinc oxide (for example Sachtotec), an iron oxide or a cerium oxide and/or zirconium oxide. Furthermore, combinations with pigmentary titanium dioxide or zinc oxide are also possible, where the particle size of these pigments are greater than or equal to 200 nm, for example Hombitan® FG or Hombitan® FFPharma.

Compositions of the invention may comprise inorganic UV filters which have been aftertreated by conventional methods, as described, for example, in *Cosmetics & Toiletries*, 1990, 105, 53-64. One or more of the following aftertreatment components can be: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerine.

In an embodiment, particulate UV filters used in compositions of the invention are:
- untreated titanium dioxides, such as, the products Microtitanium Dioxide MT 500 B from Tayca; titanium dioxide P25 from Degussa,
- aftertreated micronized titanium dioxides with aluminium oxide and silicon dioxide aftertreatment, such as, the product "Microtitanium Dioxide MT 100 SA from Tayca; or the product "Tioveil Fin" from Uniqema,
- aftertreated micronized titanium dioxides with aluminium oxide and/or aluminium stearate/laurate aftertreatment, such as, Microtitanium Dioxide MT 100 T from Tayca, Eusolex T-2000 from Merck,
- aftertreated micronized titanium dioxides with iron oxide and/or iron stearate aftertreatment, such as, the product "Microtitanium Dioxide MT 100 F" from Tayca,
- aftertreated micronized titanium dioxides with silicon dioxide, aluminium oxide and silicone aftertreatment, such as, the product "Microtitanium Dioxide MT 100 SAS", from Tayca,
- aftertreated micronized titanium dioxides with sodium hexametaphosphates, such as, the product "Microtitanium Dioxide MT 150 W" from Tayca.

The treated micronized titanium dioxides employed for the combination may also be aftertreated with:
- octyltrimethoxysilanes; such as, the product Tego Sun T 805 from Evonik Goldschmidt GmbH,
- silicon dioxide; such as, for example, the product Parsol T-X from DSM,
- aluminium oxide and stearic acid; such as, the product UV-Titan M160 from Sachtleben,
- aluminium and glycerine; such as, the product UV-Titan from Sachtleben,
- aluminium and silicone oils, such as, the product UV-Titan M262 from Sachtleben,
- sodium hexametaphosphate and polyvinylpyrrolidone,
- polydimethylsiloxanes, such as, the product 70250 Cardre UF TiO2SI3" from Cardre,
- polydimethylhydrogenosiloxanes, such as, for example, the product Microtitanium Dioxide USP Grade Hydrophobic" from Color Techniques.

In a particular embodiment, compositions of the invention may include untreated zinc oxides, such as, the product Z-Cote from BASF (Sunsmart), Nanox from Elementis. In another particular embodiment, compositions of the invention may include aftertreated zinc oxides, such as, the following products:
- "Zinc Oxide CS-5" from Toshibi (ZnO aftertreated with polymethylhydrogeno-siloxanes);
- Nanogard Zinc Oxide FN from Nanophase Technologies;
- "SPD-Z1" from Shin-Etsu (ZnO aftertreated with a silicone-grafted acrylic polymer, dispersed in cyclodimethylsiloxanes;
- "Escalol Z100" from ISP (aluminium oxide-aftertreated ZnO dispersed in an ethylhexyl methoxycinnamate/PVP-hexadecene/methicone copolymer mixture); and
- "Fuji ZNO-SMS-10" from Fuji Pigment (ZnO aftertreated with silicon dioxide and polymethylsilesquioxane).

In another particular embodiment, compositions of the invention may include untreated cerium oxide micropigment, for example with the name "Colloidal Cerium Oxide" from Rhone Poulenc. In another particular embodiment, compositions of the invention may include untreated and/or aftertreated iron oxides with the name Nanogar from Arnaud.

By way of example, it is also possible to employ mixtures of various metal oxides, such as, for example, titanium dioxide and cerium oxide, with and without aftertreatment, such as, for example, the product Sunveil A from Ikeda. In addition, mixtures of aluminium oxide, silicon dioxide and silicone-aftertreated titanium dioxide, zinc oxide mixtures, such as, the product UV-Titan M261 from Sachtleben, can also be used in combination with the UV protection agents according to the invention.

Inorganic UV filters are generally incorporated into the preparations in an amount of 0.1 percent by weight to 25 percent by weight, preferably 2% by weight-10% by weight.

By combination of one or more of the said compounds having a UV filter action, the protective action against harmful effects of the UV radiation can be optimized.

All said UV filters can also be employed in encapsulated form. In particular, it is advantageous to employ organic UV filters in encapsulated form. The capsules in preparations to be employed in accordance with the invention are preferably present in amounts which ensure that the encapsulated UV filters are present in the preparation in the percent by weight ratios indicated above.

Particular compositions of the invention comprise at least one further cosmetic active compound, for example selected from antioxidants, anti-ageing compounds, anti-wrinkle, anti-flake, anti-acne, deodorants, anti-cellulite compounds and vitamins. Antioxidants include amino acids (for example glycine, histidine, tyrosine, tryptophan) and derivatives thereof, imidazoles, (for ecample urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to mmol/kg), and also (metal) chelating agents, (for example α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate) and coniferyl benzoate of benzoin resin, rutinic acid and derivatives thereof, a-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Mixtures of antioxidants are likewise suitable for use in the compositions of the invention. Available mixtures are, for example, mixtures comprising, as active ingredients, lecithin, L-(+)-ascorbyl palmitate and citric acid, natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed in such preparations with the compounds according to the invention in percent by weight ratios in the range from 1000:1 to 1:1000, preferably in percent by weight ratios of 100:1 to 1:100.

Of the phenols, the polyphenols, such as flavonoids or bioflavonoids, which are principally known as plant dyes, frequently have an antioxidant potential. Quercetin (cyanidanol, cyanidenolon 1522, meletin, sophoretin, ericin, 3,3',4',5,7-pentahydroxyflavone) is another antioxidant agent suitable for compositions of the invention.

In another aspect, there is provided a kit comprising a composition of the invention and instructions for using said composition for sunless tanning. In a particular embodiment the instructions are printed on packaging containing said composition.

The invention will now be illustrated by the following non-limiting Examples.

EXAMPLES

All chemicals were purchased from Sigma Chemicals, St. Louis, Mo. All compounds were characterized by 1H NMR, 13C NMR, mass and melting point analysis. Nuclear Magnetic Resonance spectra were recorded on a Varian XL 600 MHz instrument. All 1H and $^{13}$C NMR experiments are reported in units, parts per million (ppm), and were measured relative to residual DMSO in the deuterated solvent. All coupling constants were reported in Hz. Melting points were determined on Mel-Temp II apparatus and are uncorrected. Mass analyses were performed on Agilent LC-TOF 1100 mass spectrometer equipped with either an ESI or APCI source.

Example 1: Preparation of Compounds 3a, 3b, 3c and 3d

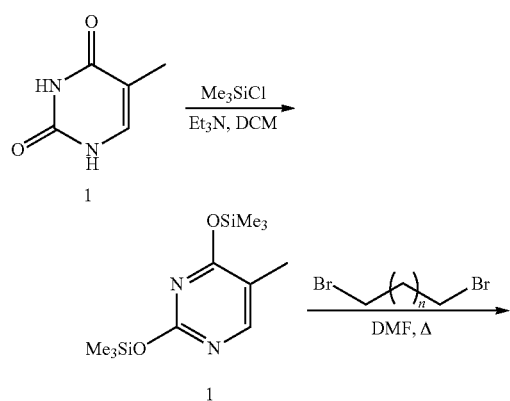

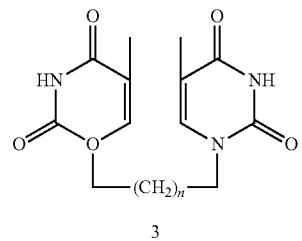

3
3a,; n = 1  3b; n = 2
3c; n = 3  3d; n = 4

To a solution of 1,3-dibromopropane (2.202 g, 10.07 mmol) in 50 mL of anhydrous DMF was added O,O'-bis (trimethylsilyl)-thymine (2) (6.256 g, 23.17 mmol). The solution was heated to 170° C. and stirred overnight. The reaction was cooled to 0° C. and 10 mL of water was added to the reaction mass to precipitate the product. The precipitated mass was stirred for 15 min at 0° C. The solids were filtered off, washed with 100 mL of chloroform-methanol (1:1) and dried under vacuum to give compound 3a (2.351 g, 81%) as an off white solid. $^1$H NMR (600 MHz, DMSO-d$^6$): δ 11.20 (s, 2H), 7.51 (s, 2H), 3.71 (t, 4H, J=7.04 Hz), 1.91 (t, 4H, J=7.04 Hz), 1.73 (s, 6H); $^{13}$C NMR (150 MHz, DMSO-d$^6$): δ 164.72, 151.36, 141.68, 108.98, 45.27, 28.31, 12.37; Mass (ESI-MS): 293.154 (M+H); m.p: 330-334° C.; Compounds 3b, 3c and were prepared following the procedure described for compound 3a. 3b: $^1$H NMR (600 MHz, DMSO-d$^6$): δ 11.18 (s, 2H), 7.50 (s, 2H), 3.62 (br, 4H), 1.73 (s, 6H), 1.53 (br, 4H); $^{13}$C NMR (150 MHz, DMSO-d$^6$): δ 164.71, 151.35, 141.86, 108.90, 47.16, 25.84, 12.37; Mass (ESI-MS): 307.157 (M+H); m.p: 348-350° C.; 3c: $^1$H NMR (600 MHz, DMSO-d$^6$): δ 11.15 (s, 2H), 7.47 (s, 2H), 3.57 (t, 4H, J=7.05 Hz), 1.71 (s, 6H), 1.55 (quintet, 4H, J=7.05 Hz), 1.19 (br quintet, 2H, J=7.05 Hz); $^{13}$C NMR (150 MHz, DMSO-d$^6$): δ 164.70, 151.29, 141.85, 108.82, 47.37, 28.48, 23.12; 12.36; Mass (ESI-MS): 321.174 (M+H); m.p: 250-252° C.; 3d: $^1$H NMR (600 MHz, DMSO-d$^6$): δ 11.14 (s, 2H), 7.48 (s, 2H), 3.56 (t, 4H, J=7.04 Hz), 1.71 (s, 6H), 1.52 (br quintet, 4H, J=7.05 Hz), 1.22 (br quintet, 4H, J=7.04 Hz); $^{13}$C NMR (150 MHz, DMSO-d$^6$): δ 164.71, 151.29, 141.82, 108.82, 47.42, 28.77, 25.87; 12.35; Mass (ESI-MS): 354.141 (M+H); m.p: 233-235° C.

Example 2: Preparation of Compound 8

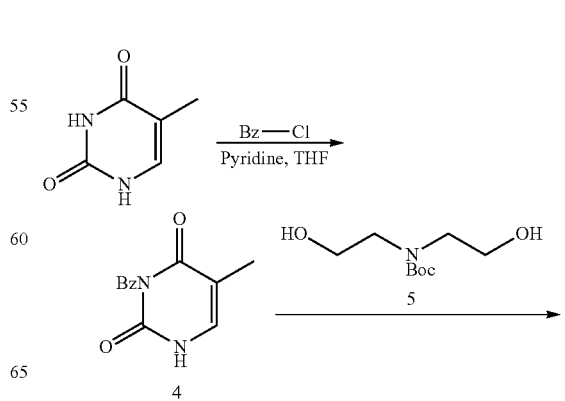

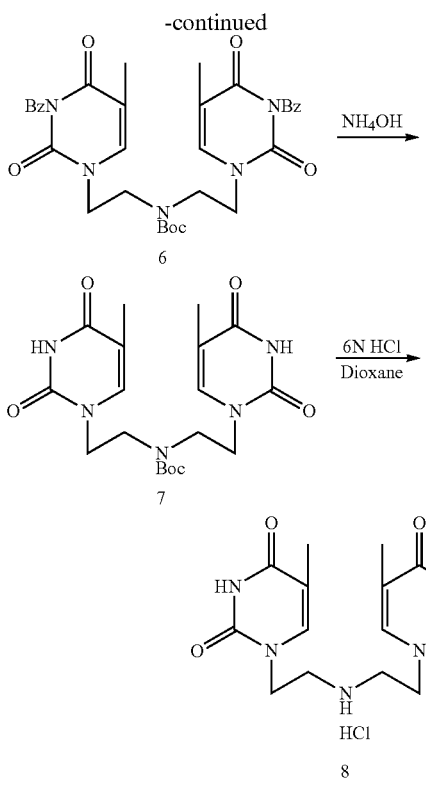

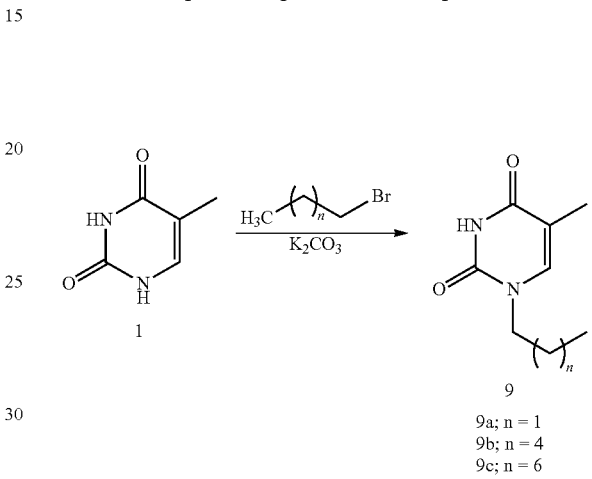

9a; n = 1
9b; n = 4
9c; n = 6

To a solution of thymine (1) in THF was added pyridine and the reaction was cooled to 0° C. Benzoyl chloride was added carefully at 0° C. and the reaction was stirred overnight at room temperature. The reaction mass was evaporated to give the crude solid which was purified by $SiO_2$ flash chromatography to give the N3-benzoyl thymine (4) as a white solid. $^1$H NMR (600 MHz, $CD_3OD$): δ 7.94 (m, 2H), 7.71 (t, 1H, J=7.3 Hz), 7.57 (m, 2H), 7.38 (s, 1H), 1.90 (s, 3H); Mass (ESI-MS): 231.22 (M+H); m.p: 178-180° C.

To a solution of $N^3$-benzoyl thymine in THF was added $PPh_3$ and DIAD and the reaction was cooled to at 0° C. Compound 5 in THF was added to the reaction mass drop-wise and the reaction was slowly brought to room temperature. Stirring was continued overnight. The organic solvents were evaporated to give the dark brown residue which was purified by $SiO_2$ flash chromatography to give the NBz-bisthymine compound 6. $^1$H NMR (600 MHz, DMSO-$d^6$): δ 7.91 (m, 4H), 7.74 (t, 2H, J=7.3 Hz), 7.67 (s, 2H), 7.56 (m, 4H), 3.74 (t, 4H, J=Hz), 2.79 (t, 4H, J=Hz), 1.79 (s, 6H), 1.43 (s, 9H); $^{13}$C NMR (150 MHz, DMSO-$d^6$): δ 170.36, 163.49, 163.25, 155.57, 150.01, 149.86, 143.07, 135.82, 135.78, 131.85, 131.57, 130.96, 130.60, 129.89, 129.64, 108.78, 108.11, 79.92, 47.12, 45.67, 44.34, 43.12, 28.15, 12.37, 12.22; Mass (ESI-MS): 630.33 (M+H); m.p: 164-166° C.

Compound 6 was dissolved in aqueous ammonia and stirred overnight at room temperature. The reaction was evaporated under vacuum to give the off-white solid which was purified by $SiO_2$ flash chromatography to give the intermediate 7. $^1$H NMR (600 MHz, DMSO-$d^6$): δ 7.93 (s, 1H), 5.56 (t, 1H), 5.21 (s, 1H), 5.06 (m, 1H), 4.99 (m, 1H), 4.36 (m, 1H), 4.06 (m, 1H), 3.84 (m, 2H), 3.58-3.51 (m, 2H), 2.86 (s, 3H), 2.71 (s, 3H), 1.51 (s, 9H); $^{13}$C NMR (150 MHz, DMSO-$d^6$): δ 162.75, 157.15, 154.08, 151.74, 135.97, 117.46, 117.14, 86.76, 85.62, 74.13, 70.08, 61.83, 36.22, 31.23, 25.56; Mass (ESI-MS): 422.43 (M+H); m.p: 254-256° C.

Compound 7 was dissolved in a solution of 6N HCl in dioxane and water (1:1) and stirred at 25° C. overnight. The solvents were evaporated under vacuum to give an oily residue which was obtained as white solid 8 after repeated evaporations with toluene. $^1$H NMR (600 MHz, DMSO-$d^6$): δ 11.23 (s, 2H); 8.01 (s, 1H), 5.74 (t, 1H), 5.47 (s, 1H), 5.68 (m, 1H), 5.01 (m, 1H), 4.93 (m, 1H), 4.53 (m, 1H), 4.01 (m, 2H), 3.85-3.65 (m, 2H), 2.95 (s, 3H), 2.85 (s, 3H); $^{13}$C NMR (150 MHz, DMSO-$d^6$): δ 165.81, 159.17, 155.80, 152.65, 136.01, 118.23, 117.94, 88.23, 86.75, 74.93, 71.48, 62.05, 36.76, 31.94; Mass (ESI-MS): 322.23 (M+H); m.p: >320° C.

Example 3: Preparation of Compound 9

To a solution of thymine 1 (5.01 g, 39.76 mmol) in anhydrous DMSO (135 mL) was added 1-bromopropane (1.601 g, 13.01 mmol) and anhydrous potassium carbonate (5.50 g, 39.28 mmol) and the resulting suspension was stirred for 10-12 h at room temperature. The solids were filtered off and the filtrate was evaporated under reduced pressure at 50° C. leaving a colorless semisolid which was suspended 500 mL water and extracted with chloroform (3×125 mL). The organic layer was dried over anhydrous $Na_2SO_4$, filtered and evaporated to give the light yellow solid which was recrystallized using absolute ethanol to give white crystalline solid 9a (0.875 g, 40.13% based on 1-bromopraopane). $^1$H NMR (600 MHz, DMSO-$d^6$): δ 11.19 (s, 1H), 7.5 (s, 1H), 3.59 (t, 2H, J=7.04 Hz), 1.72 (s, 3H), 1.59 (app. sext, 2H), 0.82 (t, 3H, J=7.63 Hz); $^{13}$C NMR (150 MHz, DMSO-$d^6$): δ 164.72, 151.32, 141.93, 108.72, 49.09, 22.16, 12.34, 11.09; Mass (ESI-MS): 169.191 (M+H); m.p: 133-135° C.

Compounds 9b and 9c were prepared in following the procedure described for compound 9a. 9b: $^1$H NMR (600 MHz, DMSO-$d^6$): δ 11.16 (s, 1H), 7.49 (s, 1H), 3.56 (t, 2H, J=7.05 Hz), 5.56 (t, 1H), 1.71 (s, 3H), 1.50-1.51 (m, 2H), 1.20-1.24 (m, 6H), 0.82 (t, 2H, J=7.04 Hz); $^{13}$C NMR (150 MHz, DMSO-$d^6$): δ 164.70, 151.28, 141.86, 108.78, 47.54, 31.26, 28.83, 25.89, 22.39, 14.27, 12.32; Mass (ESI-MS): 211.135 (M+H); m.p: 126-128° C.; 9c: $^1$H NMR (600 MHz, DMSO-$d^6$): δ 11.14 (s, 1H), 7.49 (s, 1H), 3.57 (t, 2H, J=7.63 Hz), 5.56 (t, 1H), 1.73 (s, 3H), 1.51-1.53 (m, 2H), 1.22 (m, 6H), 0.83 (t, 2H, J=7.04 Hz); $^{13}$C NMR (150 MHz, DMSO-$d^6$): δ 164.70, 151.29, 141.86, 108.78, 47.54, 31.62, 29.01, 28.86, 26.23, 22.49, 14.35, 12.33, Mass (ESI-MS): 354.141 (M+H); 239.210; m.p: 112-114° C.

Example 4: Preparation of Compound 10

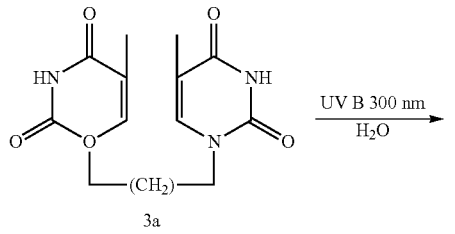

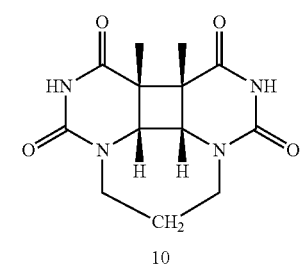

A solution of 3a (0.087 g, mmol) was dissolved in deionized water (175 mL, degassed) at 90° C., allowed to cool to room temperature in a 500 mL Pyrex flask. A stream of nitrogen was bubbled throughout the cooling to room temperature. The solution was irradiated at 300 nm in a Rayonett RPR 208 reactor and the reaction was monitored for the absorption at 270 nm with a 50:1 aliquot test solution every 1 h until reaction was complete (6 h). The irradiation was stopped and the round bottom flask was ca. taken out of the reactor. The pH was adjusted to 9 with aq.NaHCO$_3$. KMnO$_4$ (15 mg, 1.3 eq) was added and stirred at room temperature for 4-5 h. Saturated aq. NaSH (10 mL) precipitated MnO$_2$ which was removed by filtration. The carbonates in the filtrates were decomposed by careful addition of formic acid. Concentration of the solution to 30 mL furnished the photodimer as a crude product which was recrystallized from water to give the white solid 10 (0.048 g, 55.17%). $^1$H NMR (600 MHz, DMSO-d$^6$): δ 10.25 (s, 2H), 4.05 (d, 2H, J=12.91 Hz), 3.89 (m, 2H), 2.71 (m, 2H), 1.47-1.85 (m, 2H), 1.35 (s, 3H); $^{13}$C NMR (150 MHz, DMSO-d$^6$): δ 170.11, 151.29, 60.18, 46.99, 45.11, 23.96, 20.42; Mass (ESI-MS): 292.115 (M+H); m.p: >340° C.

Example 5: Preparation of Compound 11

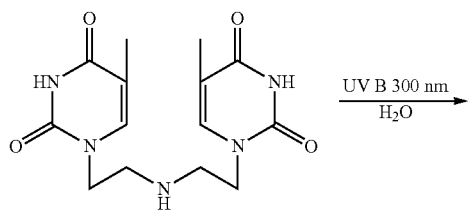

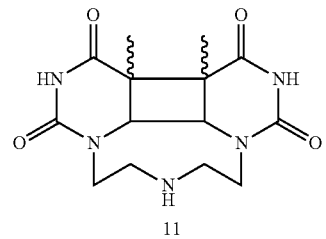

Compounds 11 were prepared in following the procedure described for compound 10 in Example 4. $^1$H NMR (600 MHz, DMSO-d$^6$): δ $^1$H NMR (600 MHz, DMSO-d$^6$): δ 10.23 (s, 2H), 5.45 (t, 1H), 5.47 (s, 1H), 5.68 (m, 1H), 5.01 (m, 1H), 4.93 (m, 1H), 4.53 (m, 1H), 4.01 (m, 2H), 3.85-3.65 (m, 2H), 2.95 (s, 3H), 2.85 (s, 3H); $^{13}$C NMR (150 MHz, DMSO-d$^6$): δ 165.81, 159.17, 155.80, 152.65, 136.01, 118.23, 117.94, 88.23, 86.75, 74.93, 71.48, 62.05, 36.76, 31.94; Mass (ESI-MS): 322.31 (M+H); m.p: >330° C.

Example 6: Preparation of Compound 12

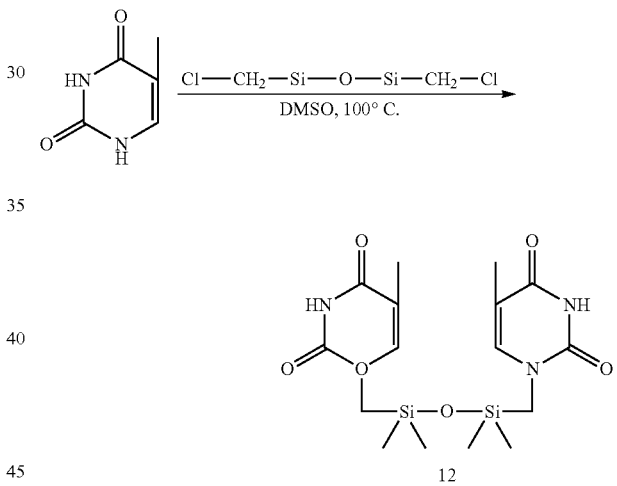

Sodium hydride (60% in mineral oil, 1.34 g, 54.33 mmol) was slowly added to a solution of thymine (6.025 g, 47.87 mmol) in dry DMSO (25 mL) and the mixture was stirred for 2 h at 50° C. Bis-chloromethyl-1,1,3,3-tetramethyldisiloxane (5.021 g, 21.73 mmol) was added and the mixture was heated for 3 days at 100° C. Reaction was brought to RT and 20 mL water was added. The reaction mass was extracted with ethyl acetate (3×50 mL). The organic layer was washed with water, brine and dried over anhydrous Na$_2$SO$_4$. The organic layer was filtered and dried under vacuum to yield the crude compound as white syrup which was recrystallized using a mixture of ethanol and ethyl acetate (9:1) and stored at −20° C. The precipitated compound was filtered and washed with 20 mL ethanol and dried under vacuum to give a white solid (6.35 g, 32.5%). $^1$H NMR (600 MHz, DMSO-d$^6$): δ (ppm) 11.14 (s, 1H), 10.89 (s, 1H), 7.30 (s, 1H), 3.09 (s, 4H), 1.64 (s, 7H), 0.00 (s, 12H); $^{13}$C NMR (150 MHz, DMSO-d$^6$): δ 164.93, 151.50, 137.73, 108.15, 45.14, 11.92, 0.00; Mass (APCI Neg.): 409.15 (M−H); m.p: 288-290° C.

Example 7: Preparation of Compound 13

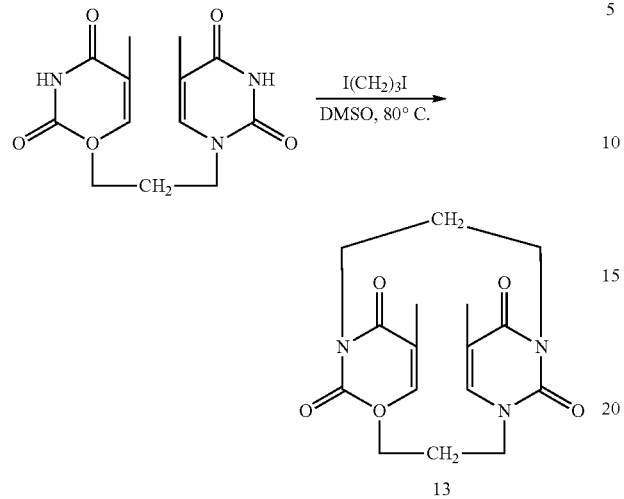

Sodium hydride 60% in oil (0.43 g, 10.7 mmol) was added to a suspension of 1,1' trimethylenebisthymine (1.51 g, 5.1 mmol) in dimethyl sulfoxide (80 mL) and stirred overnight at 60-65° C. 1, 3-Diiodopropane (1.63 g, 4.8 mmol) was added to the reaction mixture and stirred for 3 days at 80° C. to give a clear solution. The solvent was evaporated; the residual solid was washed with potassium carbonate aqueous solution (30 mL), methanol (20 mL), and diethyl ether (20 mL). The product in was purified by silica gel column using ethyl acetate/methanol as eluents to give the cyclic compound, II as a white solid (0.204 g, 12%). $^1$H NMR (600 MHz, CDCl$_3$, ppm): 7.05 (s, 2H, C6-H), 4.07 (t, 3H, N3-CH2), 3.75 (t, 4H, N1-CH2), 2.15 (t, 2H, N3-C—CH2), 1.98 (t, 2H, N1-C—CH2), 1.89 (s, 6H, C5-CH3); $^{13}$C NMR (150 MHz, CDCl$_3$): 164.11, 152.53, 141.21, 108.15, 51.20, 45.73, 28.20, 26.35, 10.35; Mass (APCI-Neg): 331.13 (M−H)

Example 8: Preparation of Compounds 24a, 24b, 24c, 24d, 24e, and 24f

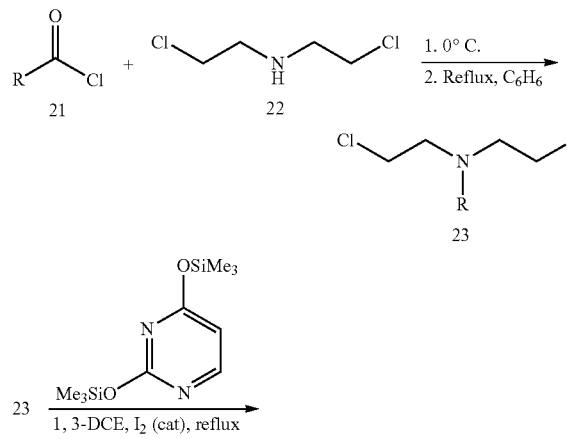

R = C$_3$H$_7$CO (24a); C$_{15}$H$_{31}$CO (24b); C$_{17}$H$_{35}$CO(24c)
Benzoyl (24d)
Cinnamoyl (24e)
OMe-cinnamoyl (24f)

To a solution of Bis-(chloroethyl)amine, 22 (1.393 g, 9.816 mmol) in benzene (20 mL) was added butyryl chloride (0.523 g, 4.908 mmol) dissolved in 10 mL benzene at 0° C. and stirred for 15 min. The reaction mass was refluxed for 1 h, cooled to RT and the precipitate was filtered off. The filtrates were evaporated to give the corresponding amide 23 (0.752 g, 72.3%) as a colorless oil. $^1$H NMR (600 MHz, DMSO-d$^6$): δ 3.75 (t, 4H), 3.51 (t, 4H), 2.71 (t, 2H), 1.45 (m, 2H), 0.76 (t, 3H); Mass (ESI-MS): 212.143 (M+H).

Compound 23 (0.251 g, 1.189 mmol) was dissolved in anhydrous 1,2-dcholoroethane (30 mL) at RT. O,O'-Bis (trimethylsilyl)-thymine (0.738 g, 2.733 mmol) was added in one portion followed by the addition of catalytic I$_2$ (14 mG, 0.05 eqv) and refluxed for 24 h. The reaction mass was evaporated to give the crude solid which was purified by SiO$_2$ flash chromatography to give the compound 24a (0.301 g, 70.82%) as an off white solid. $^1$H NMR (600 MHz, DMSO-d$^6$): δ 11.30 (s, 1H); 11.10 (s, 1H); 7.49 (s, 1H); 7.31 (s, 1H); 3.76 (t, 4H), 3.47 (t, 4H), 2.09 (t, 2H), 1.72 (s, 3H); 1.68 (s, 3H); 1.36 (t, 2H), 0.75 (t, 3H); $^{13}$C NMR (150 MHz, DMSO-d$^6$): δ 173.71, 164.41, 163.55, 152.23, 151.35, 141.74, 141.13, 109.23, 108.95, 57.74, 57.63, 47.63, 47.55, 35.84, 19.37, 13.55, 12.33, 12.21; Mass (ESI-MS): 392.19 (M+H); m.p: 298-300° C.

Compounds 24b, 24c, 24d, 24e and 24f were prepared following the procedure described for compound 24a. 24b: $^1$H NMR (600 MHz, DMSO-d$^6$): δ 11.52 (s, 1H); 11.31 (s, 1H); 7.55 (s, 1H); 7.41 (s, 1H); 3.72 (t, 4H), 3.43 (t, 4H), 2.11 (t, 2H), 1.75 (s, 3H); 1.65 (s, 3H); 1.53 (t, 2H), 1.33 (m, 2H); 1.29-1.25 (m, 22H); 0.95 (t, 3H); $^{13}$C NMR (150 MHz, DMSO-d$^6$): δ 173.15, 163.23, 163.10, 151.54, 151.43, 140.15, 139.85, 110.23, 110.20, 58.32, 58.30, 47.53, 47.50, 47.41, 35.33, 32.33, 30.68, 29.77, 29.75, 29.73, 29.72, 29.70, 29.68, 29.65, 28.98, 28.03, 23.15, 15.15, 12.85, 12.73; Mass (ESI-MS): 560.41 (M+H); m.p: 285-288° C. 24c: $^1$H NMR (600 MHz, DMSO-d$^6$): δ 11.68 (s, 1H); 11.53 (s, 1H); 7.58 (s, 1H); 7.49 (s, 1H); 3.78 (t, 4H), 3.51 (t, 4H), 2.35 (t, 2H), 1.85 (s, 3H); 1.78 (s, 3H); 1.63 (t, 2H), 1.46 (m, 2H); 1.35-1.21 (m, 28H); 0.98 (t, 3H); $^{13}$C NMR (150 MHz, DMSO-d$^6$): δ 173.31, 163.95, 163.23, 151.73, 151.81, 141.16, 140.95, 110.55, 110.34, 58.54, 58.50, 47.64, 47.61, 47.58, 35.43, 32.41, 30.72, 29.82, 29.75, 29.63, 29.71, 29.67, 29.65, 29.64, 29.61, 29.58, 28.88, 28.53, 23.45, 15.24, 12.21, 12.13; Mass (ESI-MS): 588.51 (M+H); m.p: 310-312° C. 24d: $^1$H NMR (600 MHz, DMSO-d$^6$): δ 11.57 (s, 1H), 11.48 (s, 1H), 8.33-7.68 (m, 5H), 7.54 (s, 1H), 7.45 (s, 1H), 3.81 (t, 4H), 3.76 (t, 4H), 1.71 (s, 3H), 1.68 (s, 3H); $^{13}$C NMR (150 MHz, DMSO-d$^6$): δ 170.71, 151.21, 150.11, 140.82, 139.95, 136.35, 129.36, 128.85, 128.73, 127.63, 109.83, 108.95, 58.54, 58.35, 48.42, 48.38, 28.77, 25.87;

12.35, 12.25; Mass (ESI-MS): 426.14 (M+H); m.p: 320-322° C. 24e: ¹H NMR (600 MHz, DMSO-d⁶): δ 11.63 (s, 1H), 11.53 (s, 1H), 8.43-7.87 (m, 5H), 7.64 (s, 1H), 7.59 (s, 1H), 7.37 (s, 1H), 7.28 (s, 1H) 3.73 (t, 4H), 3.64 (t, 4H), 1.81 (s, 3H), 1.76 (s, 3H); ¹³C NMR (150 MHz, DMSO-d⁶): δ 171.65, 152.21, 151.31, 142.24, 141.84, 140.55, 137.31, 130.26, 129.15, 129.13, 128.33, 120.33, 110.33, 110.51, 58.76, 58.55, 49.32, 49.71, 28.34, 26.67; 12.51, 12.45; Mass (ESI-MS): 452.17 (M+H); m.p: 315-317° C. 24f: ¹H NMR (600 MHz, DMSO-d⁶): δ 11.45 (s, 1H), 11.37 (s, 1H), 7.78-6.35 (m, 5H), 7.24 (s, 1H), 7.01 (s, 1H), 6.77 (s, 1H), 3.41 (t, 4H), 3.26 (t, 4H), 1.81 (s, 3H), 1.78 (s, 3H); Mass (ESI-MS): 482.45 (M+H); m.p: 298-300° C.

Example 9: Preparation of Compound 28

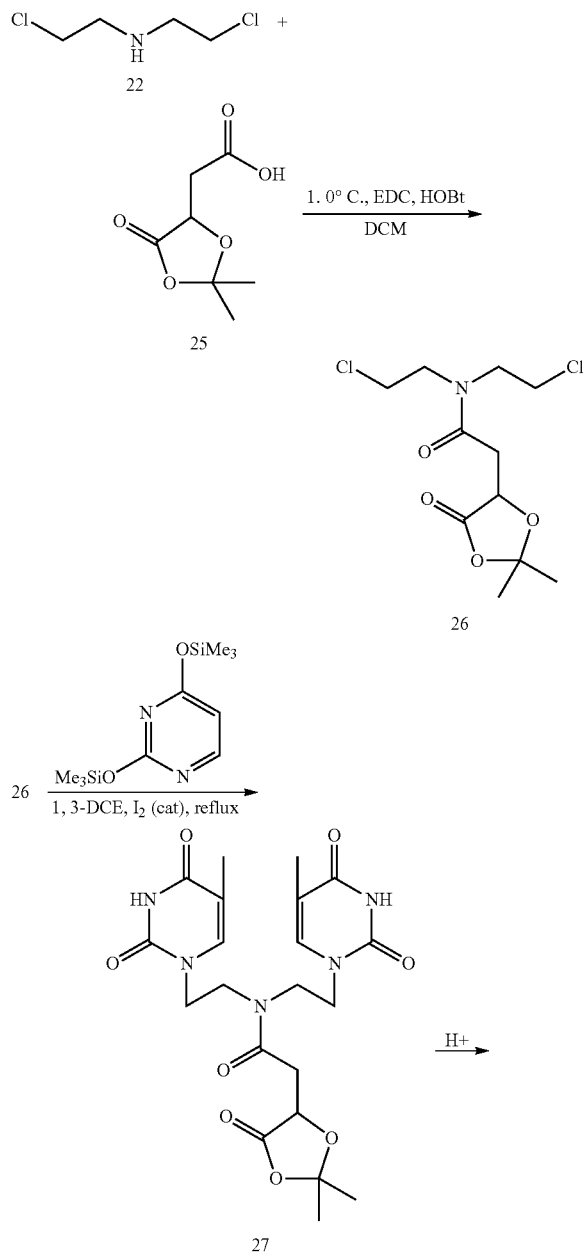

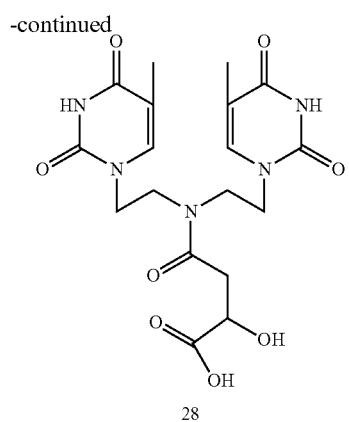

28

To a solution of acid 25 (1.752 g, 10.068 mmol) in anhydrous DCM (50 mL) was added 1-Ethyl-3-(3-dimethylaminopropyl) carbodiimide. HCl (2.922 g, 15.303 mmol) and N-hydroxybenzotriazole (2.038 g, 15.103 mmol) at 0° C. and stirred for 15 min. Bis-(chloroethyl) amine, 22 (1.511 g, 10.709 mmol) in DCM (10 mL) was added and the reaction mass was stirred overnight at RT. The reaction mass diluted with 50 mL of DCM and washed with aq. NaHO₃ solution (20 ml) and brine (20 mL). The organic layer was dried over anhydrous Na₂SO₄ and concentrated under vacuum to give the crude product which was purified by SiO₂ flash chromatography to give the compound 26 (2.651 g, 75%) as a colorless oil. ¹H NMR (600 MHz, DMSO-d⁶): δ 3.92 (t, 1H), 3.82-3.75 (m, 4H), 3.68 (m, 4H), 2.98-2.94 (dd, 2H), 1.55 (s, 3H), 1.59 (s, 3H); Mass (ESI-MS): 298.13 (M+H).

Compound 26 (1.253 g, 4.218 mmol) was dissolved in anhydrous 1,2-dcholoroethane (30 mL) at RT. O,O'-Bis (trimethylsilyl)-thymine (2.505 g, 9.281 mmol) was added in one portion followed by the addition of catalytic I₂ (20 mG, 0.05 eqv) and refluxed for 24 h. The reaction mass was evaporated to give the crude solid which was purified by SiO₂ flash chromatography to give the compound 27 (1.153 g, 56.79%) as an off white solid. ¹H NMR (600 MHz, DMSO-d⁶): δ 11.29 (s, 1H), 11.13 (s, 1H), 7.48 (s, 1H), 7.29 (s, 1H), 4.71 (t, 1H), 3.74-3.71 (m, 4H), 3.60-3.52 (m, 4H), 3.21-3.32 (m, 2H) 1.72 (s, 3H), 1.70 (s, 3H), 1.44 (s, 6H); Mass (ESI-MS): 478.67 (M+H); m.p: 285-287° C.

Compound 27 (0.851 g) was dissolved in 12N HCl in water and stirred overnight at RT. The reaction mass was concentrated under vacuum and the residue was freeze dried to obtain the compound 28 as white solid (0.725 g, 96%). ¹H NMR (600 MHz, DMSO-d⁶): δ 12.01 (br s, 1H), 11.36 (s, 1H), 11.23 (s, 1H), 7.57 (s, 1H), 7.37 (s, 1H), 4.34 (t, 1H), 3.82-3.75 (m, 4H), 3.71-3.58 (m, 4H), 3.31-3.28 (m, 2H), 2.83 (d, 1H), 1.79 (s, 3H), 1.80 (s, 3H), 1.78 (s, 6H); ¹³C NMR (150 MHz, DMSO-d⁶): δ 176.15, 171.87, 153.14, 152.34, 142.65, 142.11, 140.96, 137.84, 131.25, 129.62, 129.33, 128.72, 120.84, 109.31, 109.85, 71.21, 58.54, 49.75, 36.23, 28.34, 26.54; 12.35, 12.29; Mass (ESI-MS): 438.77 (M+H); m.p: 321-323° C.

Example 10: Preparation of Compound 32

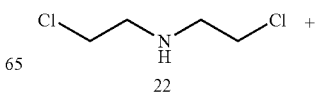

22

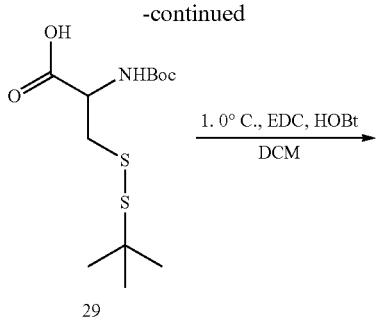

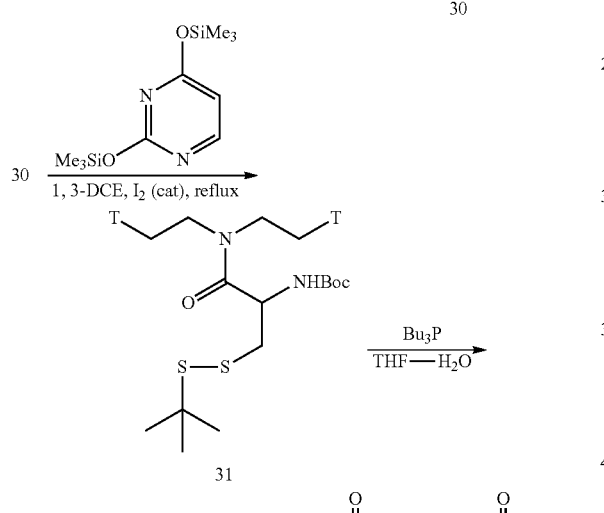

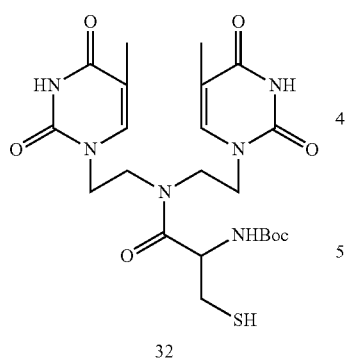

To a solution of acid 29 (1.250 g, 4.045 mmol) in anhydrous DCM (50 mL) was added 1-Ethyl-3-(3-dimethylaminopropyl) carbodiimide. HCl (0.819 g, 6.067 mmol) and N-hydroxybenzotriazole (1.158 g, 6.067 mmol) at 0° C. and stirred for 15 min. Bis-(chloroethyl)amine, 22 (0.684 g, 4.854 mmol) in DCM (10 mL) was added and the reaction mass was stirred overnight at RT. The reaction mass diluted with 50 mL of DCM and washed with aq. NaHO$_3$ solution (20 ml) and brine (20 mL). The organic layer was dried over anhydrous Na$_2$SO$_4$ and concentrated under vacuum to give the crude product which was purified by SiO$_2$ flash chromatography to give the compound 30 (1.035 g, 59.24%) as a colorless oil. $^1$H NMR (600 MHz, DMSO-d$^6$): δ 4.81 (m, 1H), 3.84-3.78 (m, 4H), 3.70-3.64 (m, 4H), 3.01-2.86 (dd, 2H), 1.43 (s, 9H), 1.34 (s, 9H); Mass (ESI-MS): 433.45 (M+H).

Compound 30 (0.752 g, 1.74 mmol) was dissolved in anhydrous 1,2-dcholoroethane (50 mL) at RT. O,O'-Bis(trimethylsilyl)-thymine (1.445 g, 5.353 mmol) was added in one portion followed by the addition of catalytic I$_2$ (20 mG) and refluxed for 24 h. The reaction mass was evaporated to give the crude solid which was purified by SiO$_2$ flash chromatography to give the compound 11 (0.575 g, 55.82%) as an off white solid. $^1$H NMR (600 MHz, DMSO-d$^6$): δ 11.63 (s, 1H), 11.45 (s, 1H), 7.54 (s, 1H), 7.50 (s, 1H), 4.93 (m, 1H), 4.01-3.84 (m, 4H), 3.91-3.72 (m, 4H), 3.76-2.92 (dd, 2H), 1.75 (s, 6H), 1.51 (s, 9H), 1.45 (s, 9H); Mass (ESI-MS): 613.51 (M+H); m.p: 275-280° C.

Compound 31 (0.425 g, 0.857 mmol) was dissolved in THF-H$_2$O (1:1) and tri-butyl phosphine (0.173 g, 1.027 mmol) was added and the reaction mass was stirred at RT for 24 h.

The solvents were evaporated to give the crude solid which was purified by SiO$_2$ flash chromatography to give the compound 32 (0.245 g, 67.5%) as white solid. $^1$H NMR (600 MHz, DMSO-d$^6$): δ 11.74 (s, 1H), 11.65 (s, 1H), 7.36 (s, 1H), 7.31 (s, 1H), 5.01 (m, 1H), 4.17-4.01 (m, 4H), 3.98-3.81 (m, 4H), 3.76-3.52 (dd, 2H), 1.73 (s, 6H), 1.35 (s, 9H); $^{13}$C NMR (150 MHz, DMSO-d$^6$): δ 170.11, 163.65, 163.52, 155.81, 151.43, 151.38, 140.61, 110.32, 80.21, 58.67, 57.43, 47.81, 28.21, 28.18, 28.17 27.51, 12.25, 12.28; Mass (ESI-MS): 525.13 (M+H); m.p: 300-305° C.

Example 11: Preparation of Compounds 115 and 116

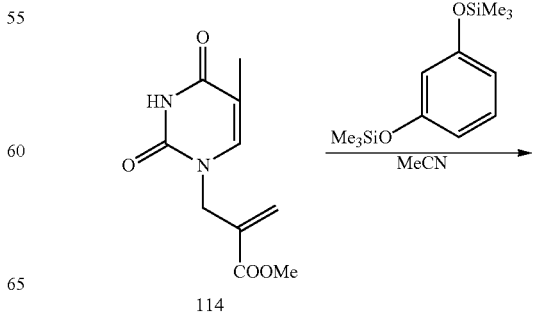

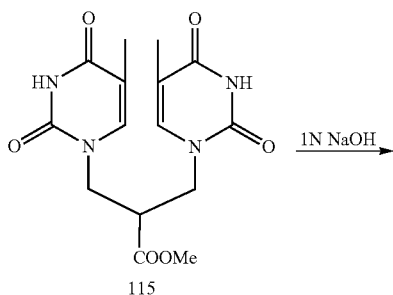

115

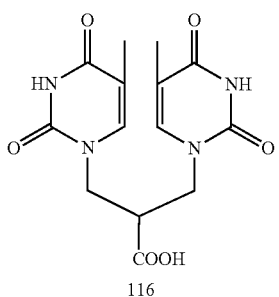

116

To a solution of O,O'-Bis(trimethylsilyl)-thymine (0.401 g, 1.482 mmol) in anhydrous DMF was added the dibromoester, 113 (0.255 g, 0.988 mmol) at RT and the reaction was heated to 75-80° C. The reaction mass was evaporated to give an oily residue which was purified by SiO$_2$ flash chromatography to give the compound 114 (0.143 g, 64.7%) as an off white solid. $^1$H NMR (600 MHz, DMSO-d$^6$): δ 11.09 (s, 1H), 7.23 (s, 1H), 6.26 (s, 1H), 5.52 (s, 1H), 4.01 (s, 2H), 3.43 (s, 3H), 1.85 (s, 3H); Mass (ESI-MS): 224.36 (M+).

To a solution of compound 114 (0.125 g, 0.558 mmol) in acetonitrile (30 mL) was added the O,O'-Bis(trimethylsilyl)-thymine (0.181 g, 0.669 mmol) at RT and the reaction was stirred at RT. The reaction mass was evaporated to give the crude solid which was purified by SiO$_2$ flash chromatography to give the compound 115 (0.139 g, 71.28%) as an off white solid. $^1$H NMR (600 MHz, DMSO-d$^6$): δ 11.25 (s, 2H), 7.46 (s, 2H), 3.83 (d, 4H), 3.54 (s, 3H), 3.43 (m, 1H), 1.71 (s, 6H); $^{13}$C NMR (150 MHz, DMSO-d$^6$): δ 174.12, 164.51, 151.35, 139.24, 53.11, 50.23, 40.34, 15.21, 15.18; Mass (ESI-MS): 351.75 (M+H).

To a solution of compound 115 (0.113 g, 0.322 mmol) in water (10 mL) was added 1N NaOH (10 mL) at 0° C. and stirred carefully for 2-3 h. The pH of the reaction was adjusted to acidic (pH-2) and the precipitated reaction mass was filtered, washed with dioxane-MeOH (1:1, 20 mL) and dried under vacuum to give the compound 116 (0.072 g, 66.71%) as a white solid. $^1$H NMR (600 MHz, DMSO-d$^6$): δ 12.81 (s. 1H), 11.24 (s, 2H), 7.44 (s, 2H), 3.81 (d, 4H), 3.15 (m, 1H), 1.70 (s, 6H); $^{13}$C NMR (150 MHz, DMSO-d$^6$): δ 179.25, 164.87, 152.33, 140.27, 51.47, 42.33, 16.22, 16.20; Mass (ESI-MS): 335.13 (M−H).

Example 12: Preparation of Salts 117 and 118

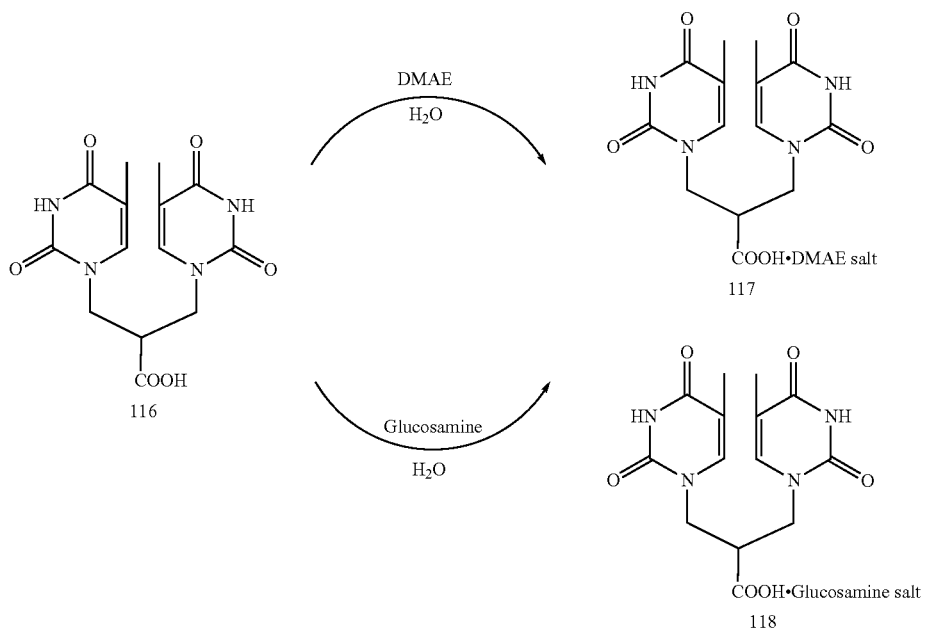

To a solution of the acid 116 (0.105 g, 0.312 mmol) in water (20 mL) was slowly added N,N-dimethylaminoethanol (DMAE) (0.027 g, 0.312 mmol)) at RT. The contents were stirred for 1-2 h at RT. The solvent was lyophilized to give an amorphous solid which was washed with diethyl ether (25 mL) and dried under vacuum to give the DMAE salt of the acid 117, as an off white powder. (0.125 g, 94%). $^1$H NMR (600 MHz, DMSO-d$^6$): δ 10.76 (s, 2H), 7.16 (s, 2H), 3.71 (d, 4H), 3.42 (d, 2H), 3.01 (m, 1H), 2.71 (d, 2H), 2.44 (s, 6H), 1.63 (s, 6H); Mass (ESI-MS): 335.46 (M−H)

To a solution of the acid 116 (0.125 g, 0.372 mmol)) in water (20 mL) was slowly added glucosamine (0.066 g, 0.372 mmol) at RT. The contents were stirred for 1-2 h at RT. The solvent was lyophilized to give an amorphous solid and washed with diethyl ether (30 mL). The solids were dried under vacuum to give the glucosamine salt of the acid 118, as a white powder (0.173 g, 90.57%). $^1$H NMR (600 MHz, DMSO-d$^6$): 11.12 (s, 2H), 7.21 (s, 2H), 5.65 (d, 1H), 4.12-3.81 (m, 1H), 4.01-2.91 (m, 1H), 3.73 (d, 4H), 3.66 (m, 1H), 3.45 (m, 1H), 1.71 (s, 6H); Mass (ESI-MS): 335.87 (M−H).

Example 13: Preparation of Compound 121

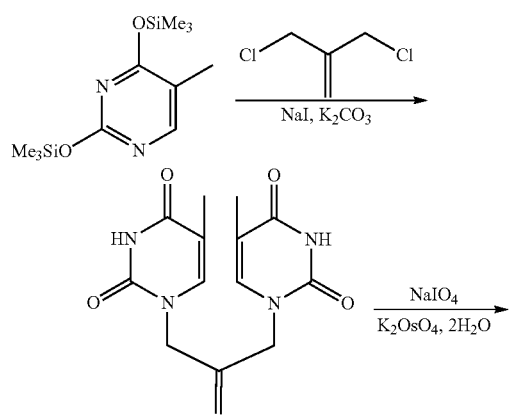

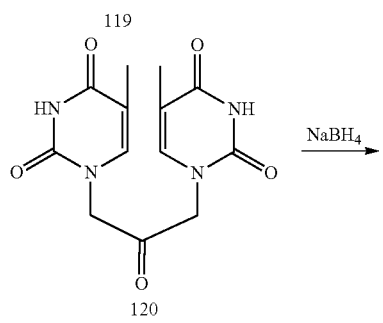

To a solution of O,O'-Bis(trimethylsilyl)-thymine (1.186 g, 4.392 mmol) was added 3-chloro-(2-chloromethyl)prop-1-ene (0.252 g, 1.640 mmol), NaI (20 mG, 0.157 mmol) and potassium carbonate (0.559 g, 3.992 mmol) in anhydrous DMF (50 mL). The mixture was heated to 80° C. and stirred overnight. DMF was evaporated and the residue was purified by SiO$_2$ flash chromatography to give the compound 119 as a white solid (0.345 g, 56.3%). $^1$H NMR (600 MHz, DMSO-d$^6$): 11.23 (s, 2H), 7.01 (s, 2H), 5.45 (s, 1H), 5.21 (s, 1H), 5.65 (d, 1H), 3.81 (s, 4H); 1.75 (s, 6H); Mass (ESI-MS): 304.71 (M+).

Compound 119 (0.301 g, 0.99 mmol) was dissolved in a mixture of THF-H$_2$O (1:0.5 ratio; 30 mL). Sodium-periodate (1.059 g, 4.948 mmol) was added in portion and stirred for 10 min at RT. Potassium osmate(VI) dihydrate (0.036 g, 0.099 mmol) was added to the reaction mass and stirred overnight at RT. The solvents were evaporated and methanol (10 mL) was added to dissolve the product and filtered. The filtrate were evaporated and the residue was purified by SiO$_2$ flash chromatography to give the compound 120 as a white solid (0.125 g, 41.31%). $^1$H NMR (600 MHz, DMSO-d$^6$): 11.12 (s, 2H), 6.31 (s, 2H), 4.13 (s, 4H), 1.81 (s, 6H); $^{13}$C NMR (150 MHz, DMSO-d$^6$): δ 198.12, 163.34, 151.17, 140.57, 110.34, 55.73, 15.23, 15.22; Mass (ESI-MS): 304.63 (M+); m.p: 320-331° C.

The compound 120 (0.158 g, 0.516 mmol) was suspended in H$_2$O (20 mL) and cooled to 0° C. Sodiumborohydride (0.191 g, 5.613 mmol) was carefully added to the reaction mixture in two portions. The reaction was stirred for 2 h at 0° C. and slowly brought to RT. Methanol (10 mL) was carefully introduced followed by the addition of H$_2$O (25 mL) to precipitate the solids. The compound was recrystallized using a mixture of water and ethanol (1:1) to give the compound 121 as a white solid (0.105 g, 66.03%). $^1$H NMR (600 MHz, DMSO-d$^6$): 11.01 (s, 2H), 6.45 (s, 2H), 4.66-3.33 (m, 6H), 2.11 (s, 6H); $^{13}$C NMR (150 MHz, DMSO-d$^6$): δ 165.37, 150.43, 142.51, 111.57, 65.77, 1.23, 15.31, 15.28; Mass (ESI-MS): 308.71 (M+); m.p: 319-322° C.

Example 14: Preparation of Compound 122

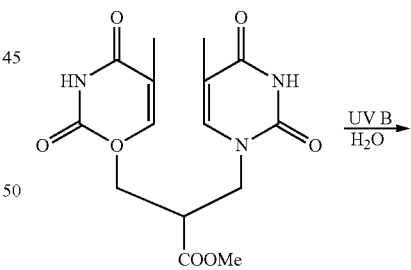

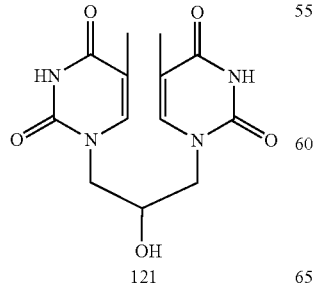

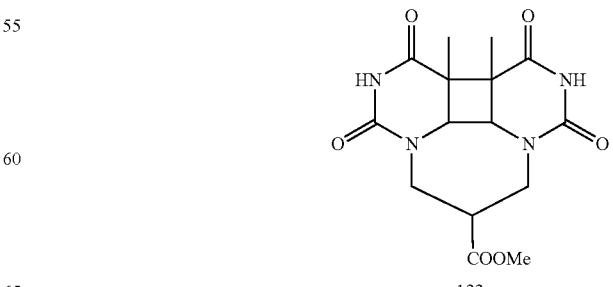

A solution of 115 (0.052 g, 0.148 mmol) was dissolved in deionized water (100 mL, degassed) at 90° C., allowed to cool to room temperature in a 500 mL Pyrex flask. A stream of nitrogen was bubbled throughout the cooling to room temperature. The solution was irradiated at 300 nm in a Rayonet RPR 208 reactor and the reaction was monitored for the absorption at 270 nm with a 50:1 aliquot test solution every 1 h until reaction was complete (6 h). The irradiation was stopped and the round bottom flask was ca. taken out of the reactor. The pH was adjusted to 9 with aq.NaHCO$_3$. KMnO$_4$ (10 mg, 1.3 eqv) was added and stirred at room temperature for 4-5 h. Saturated aq. NaSH (10 mL) precipitated MnO$_2$ which was removed by filtration. The carbonates in the filtrates were decomposed by careful addition of formic acid. Concentration of the solution to 30 mL furnished the photodimer as a crude product which was recrystallized from water to give the white solid 122 (0.025 g, 48.07%). $^1$H NMR (600 MHz, DMSO-d$^6$): δ 10.35 (s, 2H), 4.01 (d, 2H), 3.76 (d, 4H), 3.54 (s, 3H), 3.21 (m, 1H), 1.35 (s, 6H); $^{13}$C NMR (150 MHz, DMSO-d$^6$): δ 173.21, 161.15, 151.35, 57.13, 40.45, 15.33, 15.28; Mass (ESI-MS): 351.25 (M+H).

Example 15: Preparation of Salts 123 and 124

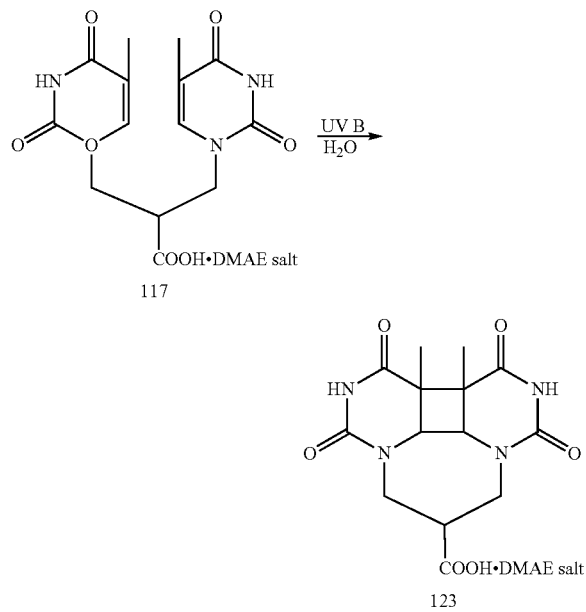

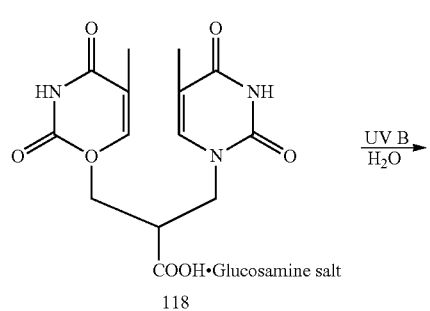

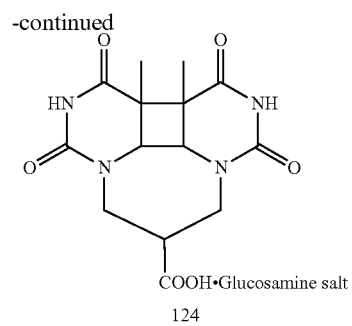

COOH•Glucosamine salt
124

A solution of DMAE salt of the acid, 117 (0.095 g, 0.223 mmol) was dissolved in deionized water (100 mL, degassed) in a 500 mL Pyrex flask. A stream of nitrogen was bubbled throughout the cooling to room temperature. The solution was irradiated at 300 nm in a Rayonet RPR 208 reactor and the reaction was monitored for the absorption at 270 nm with a 50:1 aliquot test solution every 1 h until reaction was complete (6 h). The irradiation was stopped and the round bottom flask was ca. taken out of the reactor. The pH was adjusted to 9 with aq.NaHCO$_3$. KMnO$_4$ (10 mg, 1.3 eqv) was added and stirred at room temperature for 4-5 h. Saturated aq. NaSH (10 mL) precipitated MnO$_2$ which was removed by filtration. The carbonates in the filtrates were decomposed by careful addition of formic acid. Concentration of the solution to 30 mL furnished the photodimer as a crude product which was recrystallized from water to give the white solid 123 (0.054 g, 56.84%). $^1$H NMR (600 MHz, DMSO-d$^6$): δ 10.22 (s, 2H), 4.22 (d, 2H), 3.97-3.86 (d, 4H), 3.76 (d, 4H), 3.54 (s, 3H), 3.21 (m, 1H), 3.11 (m, 1H), 2.61 (d, 2H), 2.47 (s, 6H), 1.31 (s, 6H); $^{13}$C NMR (150 MHz, DMSO-d$^6$): δ 179.31, 161.60, 153.54, 59.13, 65.12, 59.10, 58.64, 52.34, 47.25, 46.67, 41.45, 14.31, 14.27; Mass (ESI-MS): 335.65 (M+H).

Compound 124 was prepared from the glucosamine salt of the acid (118) in following the procedure described for compound 123. $^1$H NMR (600 MHz, DMSO-d$^6$): δ 11.23 (s, 2H), 5.54 (d, 1H), 4.22-3.95 (m, 1H), 4.11-3.01 (m, 1H), 3.43 (d, 4H), 3.76 (m, 1H), 3.55 (m, 1H), 1.71 (s, 6H); $^{13}$C NMR (150 MHz, DMSO-d$^6$): δ 178.35, 161.75, 152.34, 100.12, 59.33, 71.23, 74.24, 66.21, 65.23, 63.15, 59.56, 58.34, 57.43, 52.71, 47.35, 46.61, 41.51, 14.23, 14.19; Mass (ESI-MS): 335.55 (M+H).

Example 16

The following illustrate representative compositions of the invention containing a compound of formula I ('Compound X').

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |

-continued

| | |
|---|---|
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

Example 17

The following illustrates a representative dermatological compositions of the invention containing a compound as described in Formula I or Formula II ('Compound X').

| Cream: 2-12% Active ingredients (Compound X) and 88-98% Inactive ingredients | |
|---|---|
| Inactive Ingredients | % (w/w) |
| Water | 65 |
| Hexadecan-1-ol ($C_{16}H_{34}O$, Cetyl alcohol) | 3.0 |
| Octadecan-1-ol ($C_{18}H_{38}O$, Stearyl alcohol) | 8.5 |
| Isopropyl myristate ($C_{17}H_{34}O_2$) | 1.0 |
| Glycerine | 0.3 |
| Propylene glycol | 20.0 |
| Polysorbate 20 (TWEEN 20) | 2.0 |
| Isopropyl palmitate | 0.2 |
| Total for inactive ingredients | 100.00 |

The above formulations may be obtained by conventional procedures well known in the pharmaceutical art.

Example 18: Pigment Changes with Topical Application of Compounds 10, 117 and 123

Compounds 10, 117 and 123 in a solution of 75% PG/25% DMSO at 300 μM and 600 μM were provided in light tight containers and stored at 4 degrees C. Solutions were brought to room temp and vortexed prior to each use. Female Guinea pigs were shaved with electric clippers and the remaining stubble removed with Nair. The dorsal area of each guinea pig was divided into 2-3 sections. Treatment with compounds/vehicle began immediately after Nair application. 25 μL of each solution was applied to the assigned treatment site twice daily for 5 days. Hair removal, monitoring and photography continued once weekly for 30 days. Photos were taken with a Nikon D80 Digital SLR camera and Miravex Antera Melanin sensing camera.

All publications, patents, and patent documents are incorporated by reference herein, as though individually incorporated by reference. The invention has been described with reference to various specific embodiments and techniques. However, it should be understood that many variations and modifications may be made while remaining within the spirit and scope of the invention.

What is claimed is:

1. A method of tanning mammalian skin comprising administering to mammalian skin in need thereof, an effective amount of a sunless tanning composition comprising a compound of formula I:

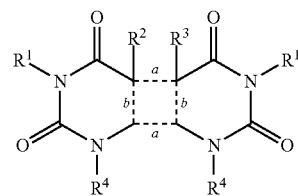

wherein:
each $R^1$ is independently H, ($C_1$-$C_6$)alkyl, ($C_3$-$C_7$)carbocycle or $R_aC(\!\!=\!\!O)$—, and the two $R^4$ groups together form a —($C_3$-$C_8$)alkyl- group, a —($C_2$-$C_6$)alkyl-Y—($C_2$-$C_6$)alkyl- group or a —($C_1$-$C_6$)alkyl-Y'—($C_1$-$C_6$)alkyl- group; or each $R^4$ is independently H, ($C_1$-$C_6$)alkyl, ($C_3$-$C_7$)carbocycle or $R_aC(\!\!=\!\!O)$—, and the two $R^1$ groups together form a —($C_3$-$C_8$)alkyl- group, a —($C_2$-$C_6$)alkyl-Y—($C_2$-$C_6$)alkyl- group or a —($C_1$-$C_6$)alkyl-Y'—($C_1$-$C_6$)alkyl- group; or the two $R^4$ groups together form a —($C_3$-$C_8$)alkyl- group, a —($C_2$-$C_6$)alkyl-Y—($C_2$-$C_6$)alkyl group or a —($C_1$-$C_6$)alkyl-Y'—($C_1$-$C_6$)alkyl- group and the two $R^1$ groups together form a —($C_3$-$C_8$)alkyl- group, a —($C_2$-$C_6$)alkyl-Y—($C_2$-$C_6$)alkyl- group or a —($C_1$-$C_6$)alkyl-Y'—($C_1$-$C_6$)alkyl- group;

the dashed bonds labeled "a" are absent and the dashed bonds labeled "b" are double bonds; or all the dashed bonds are single bonds;

$R^2$ is H, ($C_1$-$C_6$)alkyl or aryl, wherein aryl is optionally substituted with one or more $Z^1$ groups;

$R^3$ is H, ($C_1$-$C_6$)alkyl or aryl, wherein aryl is optionally substituted with one or more $Z^1$ groups;

Y is O, S, NH, $NR_c$, P, P($\!\!=\!\!O$) or POH;

Y' is Si($R_b$)$_2$ or —Si($R_b$)$_2$—O—Si($R_b$)$_2$—;

each $R_a$ is independently ($C_1$-$C_6$)alkyl, ($C_3$-$C_7$)carbocycle or aryl, wherein aryl is optionally substituted with one or more $Z^1$ groups;

each $R_b$ is independently ($C_1$-$C_6$)alkyl, ($C_3$-$C_7$)carbocycle or aryl, wherein aryl is optionally substituted with one or more $Z^1$ groups;

each $R_c$ is independently $R_g$ or a $C_1$-$C_{18}$ saturated or unsaturated carbon chain that is optionally substituted with one or more groups independently selected from oxo (=O), hydroxy, mercapto, ($C_1$-$C_6$)alkoxy, ($C_1$-$C_6$)alkoxycarbonyl, ($C_1$-$C_6$)alkanoyloxy, $NR_dR_e$, carboxy, and aryl, wherein any aryl of $R_c$ is optionally substituted with one or more $R_f$;

each $R_d$ and $R_e$ is independently selected from H, ($C_1$-$C_6$)alkyl, ($C_1$-$C_6$)alkanoyl, phenyl, benzyl, and $R_g$;

each $R_f$ is independently selected from ($C_1$-$C_6$)alkyl, ($C_1$-$C_6$)alkoxy, ($C_1$-$C_6$)alkoxycarbonyl, ($C_1$-$C_6$)alkanoyloxy, —C(=O)-phenyl, and —C(=O)CH$_2$C(=O)-phenyl, wherein any phenyl is optionally substituted with one or more groups independently selected from ($C_1$-$C_6$)alkyl, —SO$_3$H, and ($C_1$-$C_6$)alkoxy;

each $R_g$ is

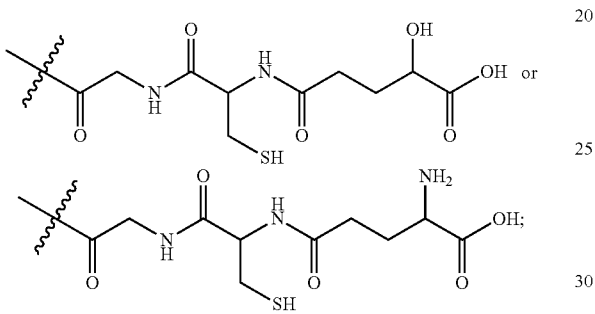

each $Z^1$ is independently selected from ($C_1$-$C_6$)alkyl, halogen, —CN, —$OR_{n1}$, —$NR_{q1}R_{r1}$, —$NR_{n1}COR_{p1}$, —$NR_{n1}CO_2R_{p1}$, NO$_2$, —C(O)$R_{n1}$, —C(O)$OR_{n1}$ and —C(O)$NR_{q1}R_{r1}$, wherein any ($C_1$-$C_6$)alkyl of $Z^1$ is optionally substituted with one or more (e.g. 1, 2, 3, 4, 5 or 6) halogen;

each $R_{n1}$ is independently selected from H and ($C_1$-$C_6$)alkyl, wherein any ($C_1$-$C_6$)alkyl of $R_{n1}$ is optionally substituted with one or more (e.g. 1, 2, 3, 4, 5 or 6) halogen;

each $R_{p1}$ is independently ($C_1$-$C_6$)alkyl; and $R_{q1}$ and $R_{r1}$ are each independently selected from H and ($C_1$-$C_6$)alkyl or $R_{q1}$ and $R_{r1}$ together with the nitrogen to which they are attached form a piperidine, pyrrolidine, morpholine, azetidine, thiomorpholine, piperazine or 4-methylpiperazine;

or a salt thereof.

2. The method of claim 1 wherein the wherein the sunless tanning composition comprises a compound of formula I selected from:

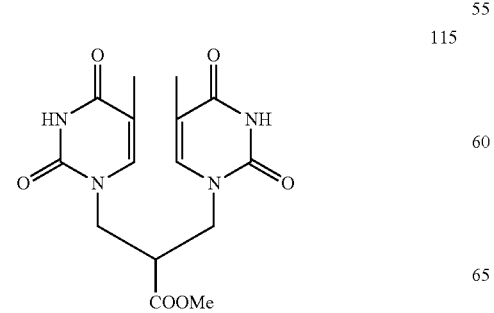

115

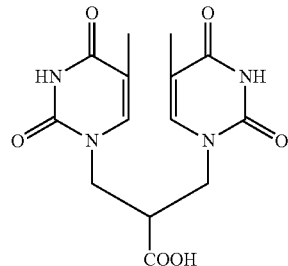

116

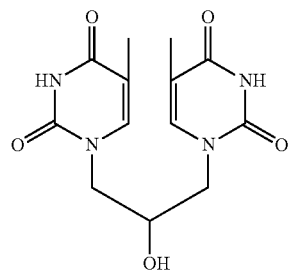

121

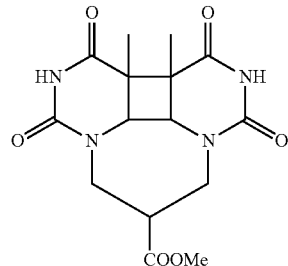

122

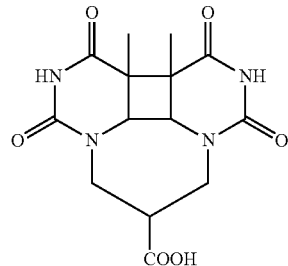

130

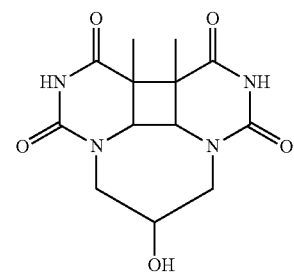

51
-continued
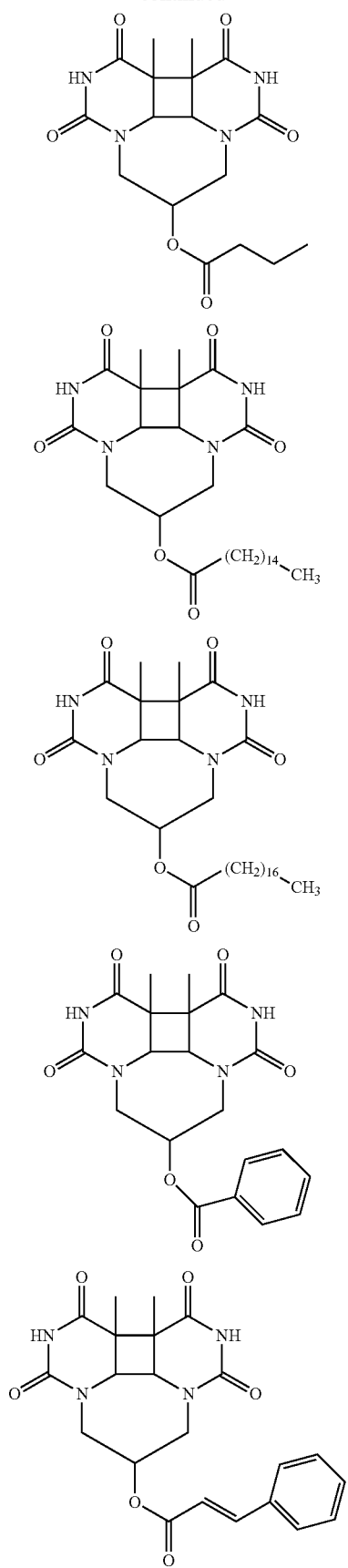
52
-continued
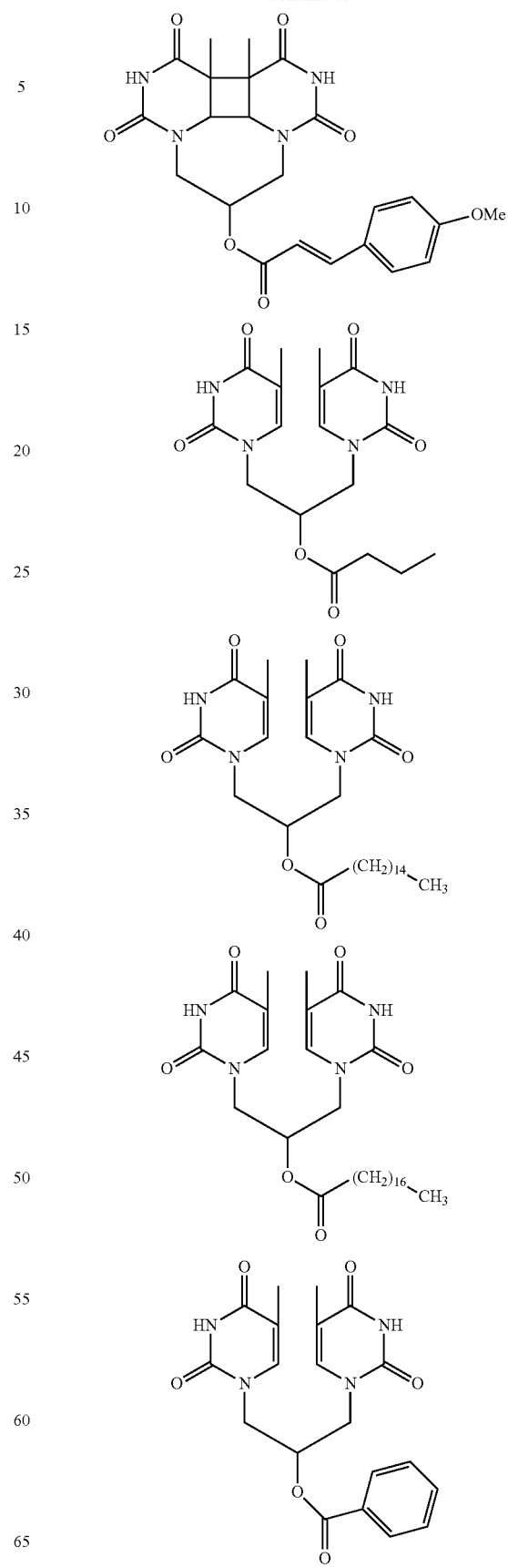

53
-continued
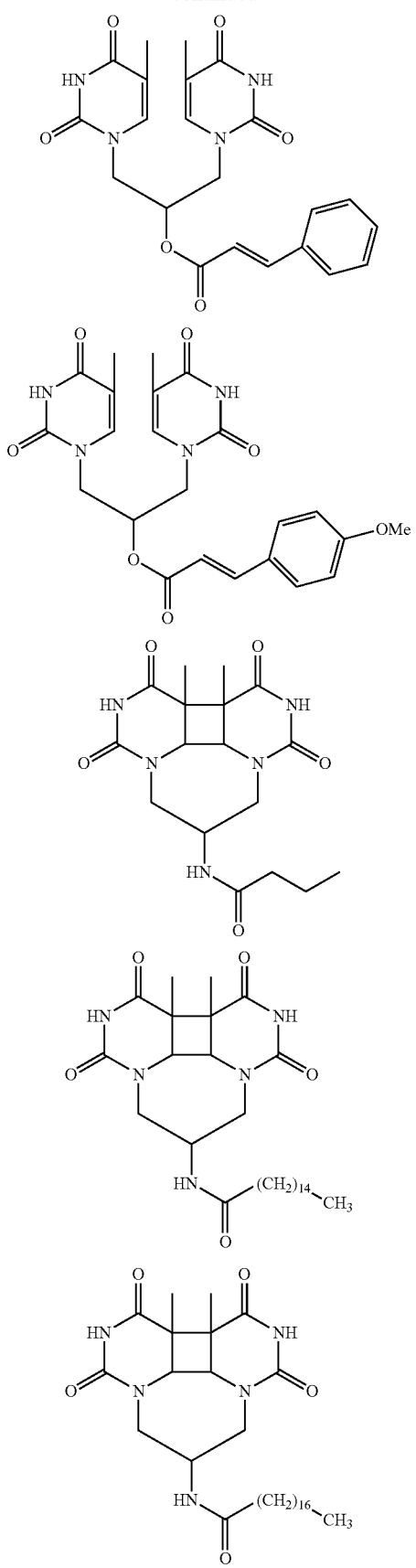
54
-continued
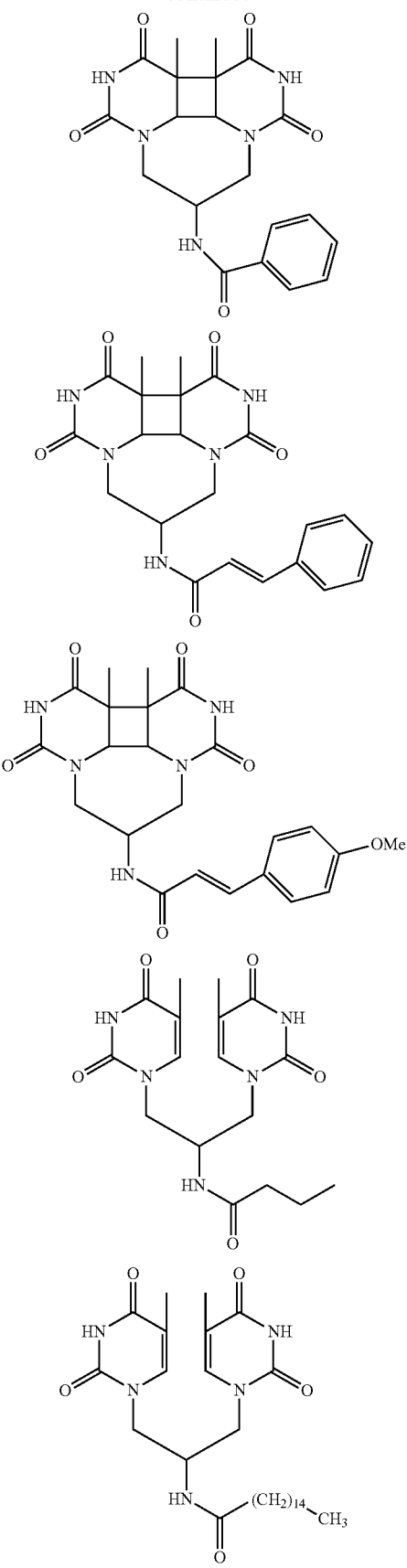

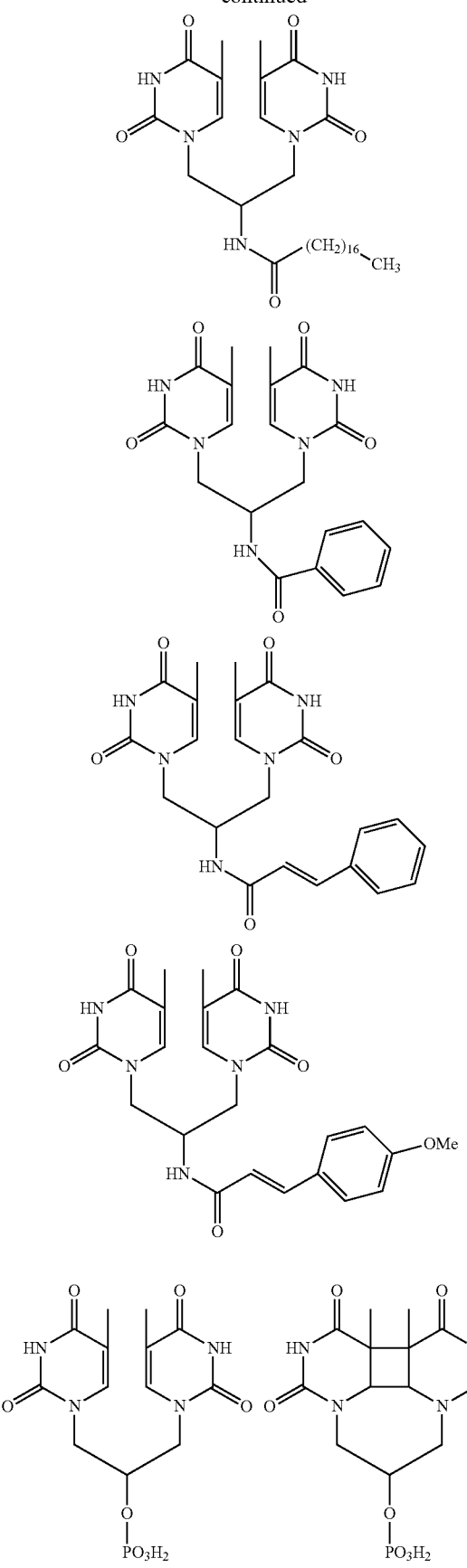

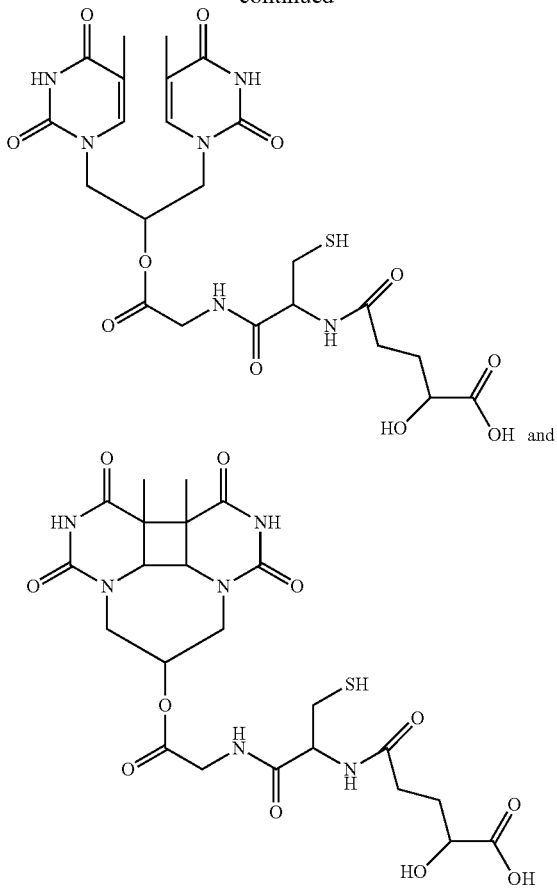

or a salt thereof.

3. A method of providing an artificial tan to mammalian skin comprising administering to mammalian skin in need thereof, an effective amount of a sunless tanning composition comprising a compound of formula I:

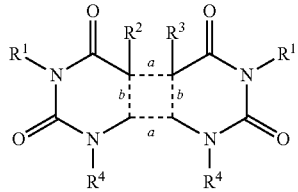

wherein:
each $R^1$ is independently H, $(C_1-C_6)$alkyl, $(C_3-C_7)$carbocycle or $R_aC(=O)—$, and the two $R^4$ groups together form a $—(C_3-C_5)$alkyl- group, a $—(C_2-C_6)$alkyl-Y—$(C_2-C_6)$alkyl- group or a $—(C_1-C_6)$alkyl-Y'—$(C_1-C_6)$alkyl- group; or each $R^4$ is independently H, $(C_1-C_6)$alkyl, $(C_3-C_7)$carbocycle or $R_aC(=O)—$, and the two $R^1$ groups together form a $—(C_3-C_5)$alkyl- group, a $—(C_2-C_6)$alkyl-Y—$(C_2-C_6)$alkyl- group or a $—(C_1-C_6)$alkyl-Y'—$(C_1-C_6)$alkyl- group; or the two $R^4$ groups together form a $—(C_3-C_5)$alkyl- group, a $—(C_2-C_6)$alkyl-Y—$(C_2-C_6)$alkyl group or a $—(C_1-C_6)$alkyl-Y'—$(C_1-C_6)$alkyl- group and the two $R^1$ groups together form a —(C$_3$-C$_8$)alkyl- group, a —(C$_2$-C$_6$)alkyl-Y—(C$_2$-C$_6$)alkyl- group or a —(C$_1$-C$_6$)alkyl-Y'—(C$_1$-C$_6$)alkyl- group;

the dashed bonds labeled "a" are absent and the dashed bonds labeled "b" are double bonds; or all the dashed bonds are single bonds;

R$^2$ is H, (C$_1$-C$_6$)alkyl or aryl, wherein aryl is optionally substituted with one or more Z$^1$ groups;

R$^3$ is H, (C$_1$-C$_6$)alkyl or aryl, wherein aryl is optionally substituted with one or more Z$^1$ groups;

Y is O, S, NH, NR$_c$, P, P(=O) or POH;

Y' is Si(R$_b$)$_2$ or —Si(R$_b$)$_2$—O—Si(R$_b$)$_2$—;

each R$_a$ is independently (C$_1$-C$_6$)alkyl, (C$_3$-C$_7$)carbocycle or aryl, wherein aryl is optionally substituted with one or more Z$^1$ groups;

each R$_b$ is independently (C$_1$-C$_6$)alkyl, (C$_3$-C$_7$)carbocycle or aryl, wherein aryl is optionally substituted with one or more Z$^1$ groups;

each R$_c$ is independently R$_g$ or a C$_1$-C$_{18}$ saturated or unsaturated carbon chain that is optionally substituted with one or more groups independently selected from oxo (=O), hydroxy, mercapto, (C$_1$-C$_6$)alkoxy, (C$_1$-C$_6$)alkoxycarbonyl, (C$_1$-C$_6$)alkanoyloxy, NR$_d$R$_e$, carboxy, and aryl, wherein any aryl of R$_c$ is optionally substituted with one or more R$_f$;

each R$_d$ and R$_e$ is independently selected from H, (C$_1$-C$_6$)alkyl, (C$_1$-C$_6$)alkanoyl, phenyl, benzyl, and R;

each R$_f$ is independently selected from (C$_1$-C$_6$)alkyl, (C$_1$-C$_6$)alkoxy, (C$_1$-C$_6$)alkoxycarbonyl, (C$_1$-C$_6$)alkanoyloxy, —C(=O)-phenyl, and —C(=O)CH$_2$C(=O)-phenyl, wherein any phenyl is optionally substituted with one or more groups independently selected from (C$_1$-C$_6$)alkyl, —SO$_3$H, and (C$_1$-C$_6$)alkoxy;

each R$_g$ is

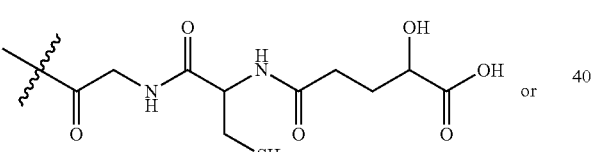

or

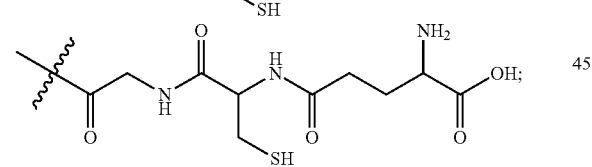

each Z$^1$ is independently selected from (C$_1$-C$_6$)alkyl, halogen, —CN, —OR$_{n1}$, —NR$_{q1}$R$_{r1}$, —NR$_{n1}$COR$_{p1}$, —NR$_{n1}$CO$_2$R$_{p1}$, NO$_2$, —C(O)R$_{n1}$, —C(O)OR$_{n1}$ and —C(O)NR$_{q1}$R$_{r1}$, wherein any (C$_1$-C$_6$)alkyl of Z$^1$ is optionally substituted with one or more (e.g. 1, 2, 3, 4, 5 or 6) halogen;

each R$_{n1}$ is independently selected from H and (C$_1$-C$_6$)alkyl, wherein any (C$_1$-C$_6$)alkyl of R$_{n1}$ is optionally substituted with one or more (e.g. 1, 2, 3, 4, 5 or 6) halogen;

each R$_{p1}$ is independently (C$_1$-C$_6$)alkyl; and

R$_{q1}$ and R$_{r1}$ are each independently selected from H and (C$_1$-C$_6$)alkyl or R$_{q1}$ and R$_{r1}$ together with the nitrogen to which they are attached form a piperidine, pyrrolidine, morpholine, azetidine, thiomorpholine, piperazine or 4-methylpiperazine;

or a salt thereof.

4. The method of claim 3 wherein the wherein the sunless tanning composition comprises a compound of formula I selected from:

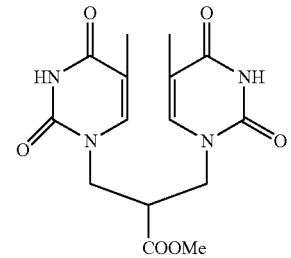

115

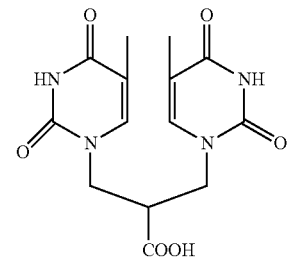

116

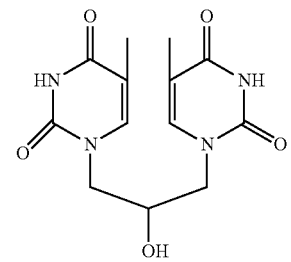

121

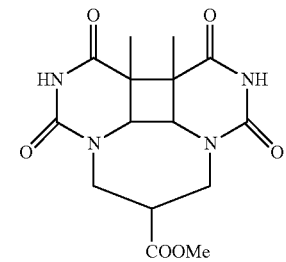

122

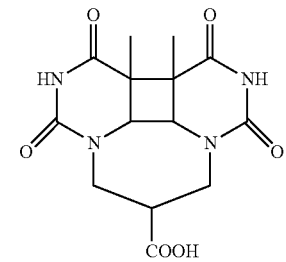

130

59
-continued
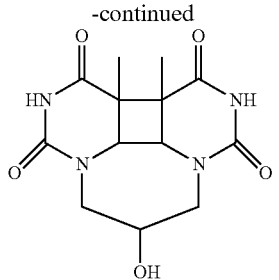
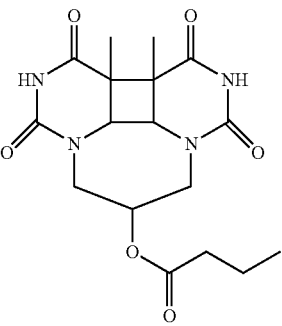
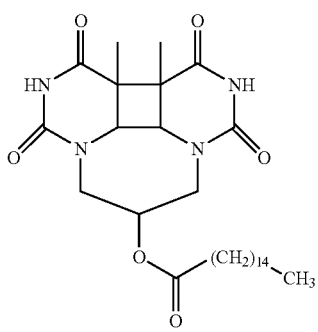
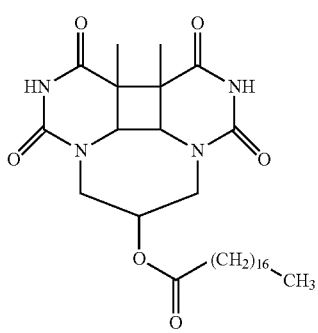
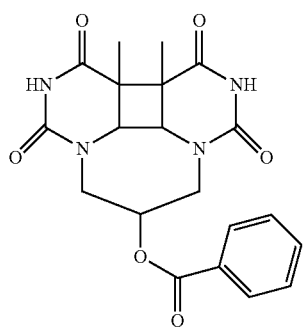
60
-continued
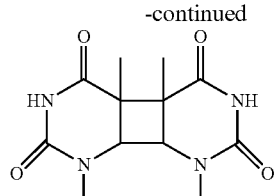
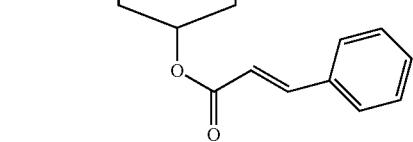
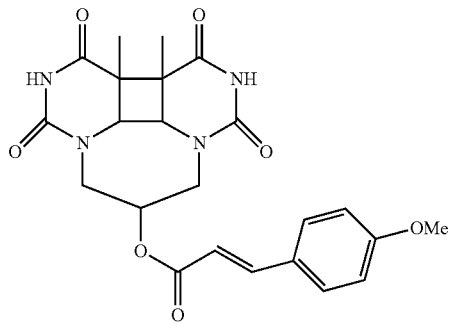
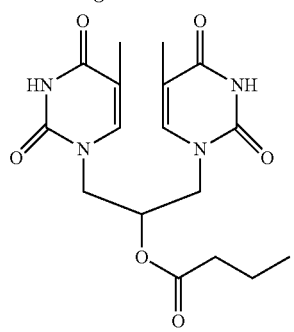
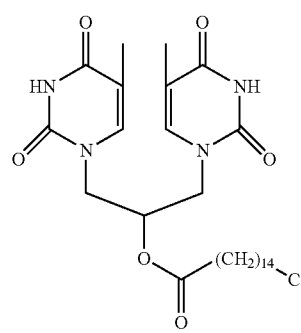
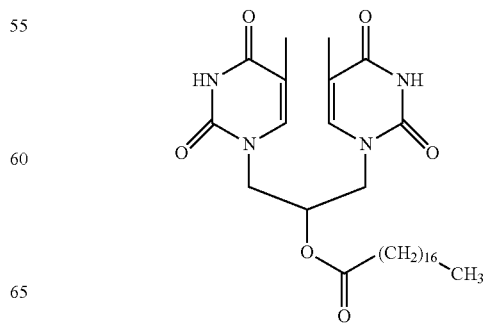

61
-continued
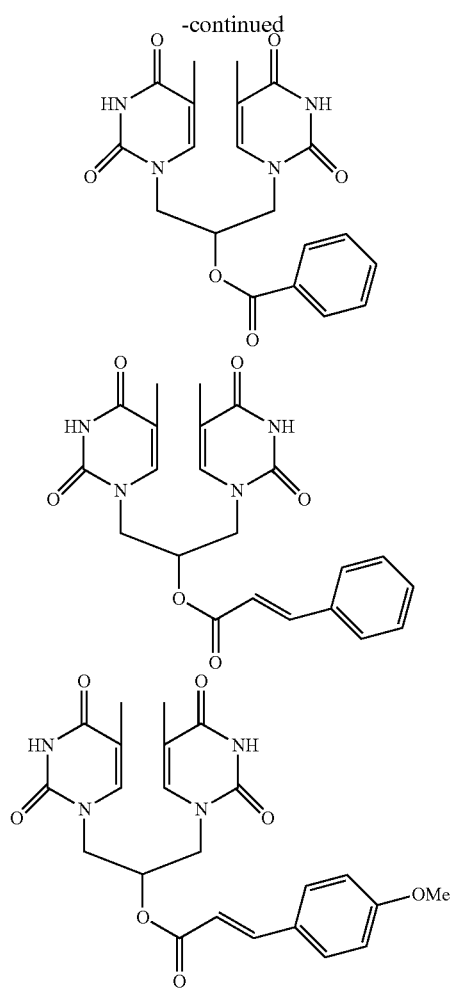
62
-continued
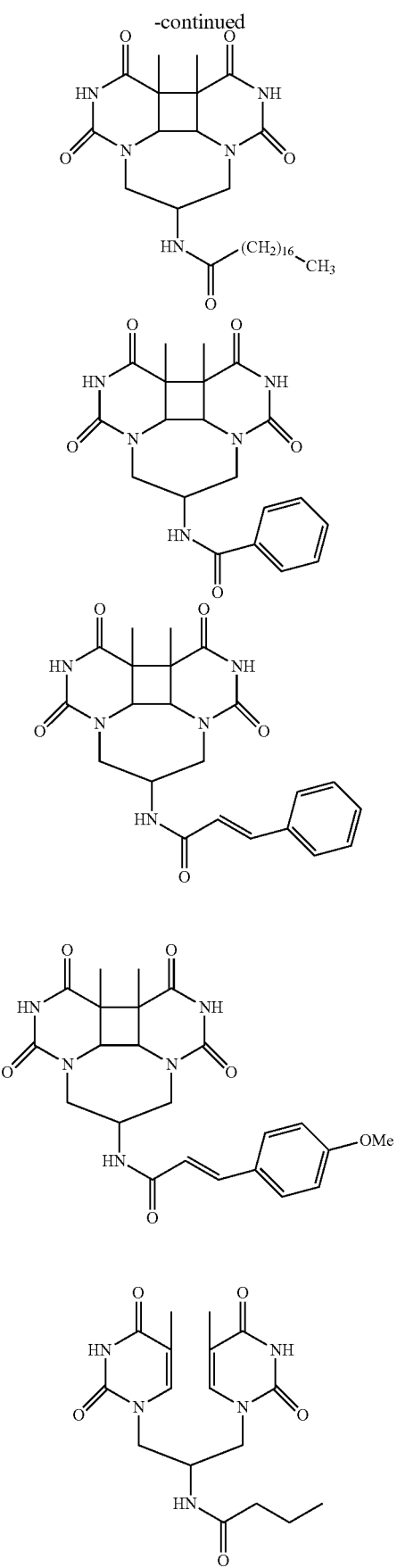

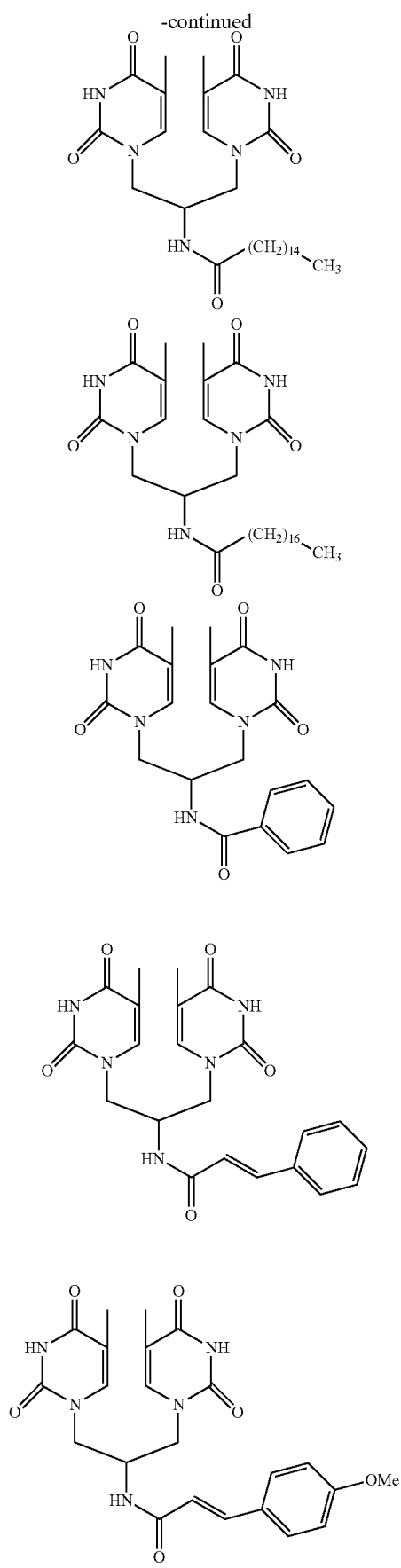
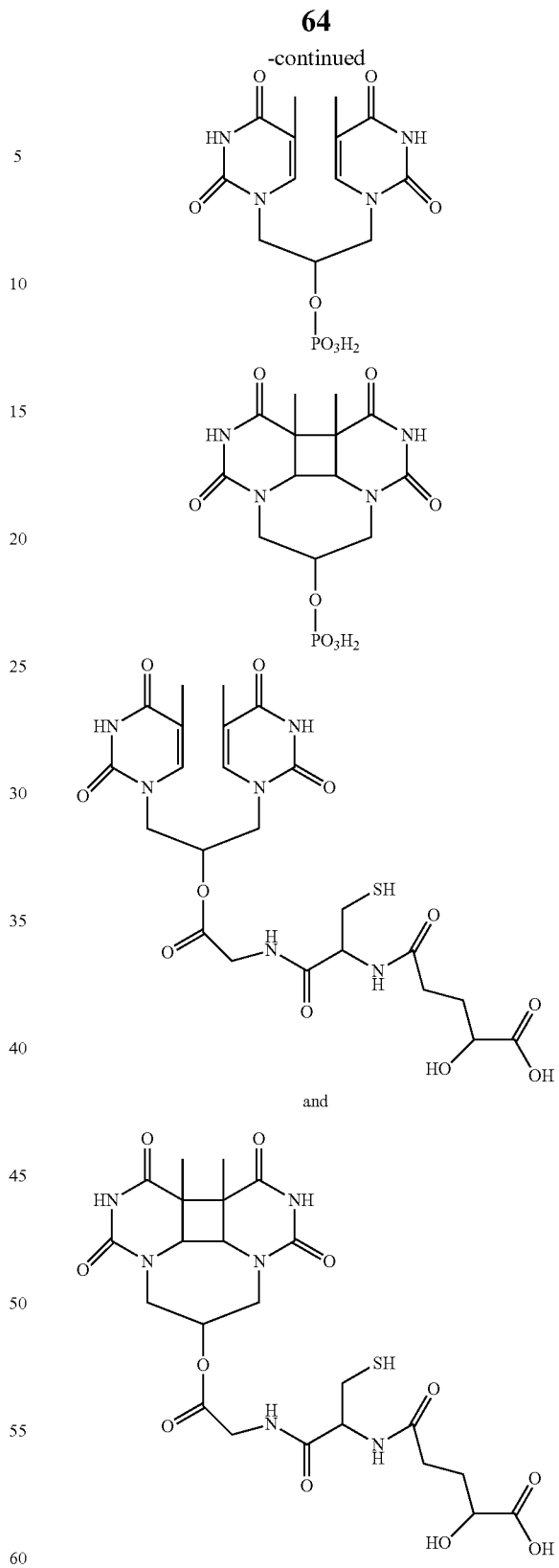
or a salt thereof.
5. A method of coloring mammalian skin, comprising administering to mammalian skin in need thereof, an effective amount of a sunless tanning composition comprising a compound of formula I:

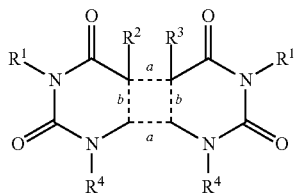

I wherein:
each $R^1$ is independently H, $(C_1-C_6)$alkyl, $(C_3-C_7)$carbocycle or $R_aC(=O)$—, and the two $R^4$ groups together form a —$(C_3-C_5)$alkyl- group, a —$(C_2-C_6)$alkyl-Y—$(C_2-C_6)$alkyl- group or a —$(C_1-C_6)$alkyl-Y'—$(C_1-C_6)$alkyl- group; or each $R^4$ is independently H, $(C_1-C_6)$alkyl, $(C_3-C_7)$carbocycle or $R_aC(=O)$—, and the two $R^1$ groups together form a —$(C_3-C_5)$alkyl- group, a —$(C_2-C_6)$alkyl-Y—$(C_2-C_6)$alkyl- group or a —$(C_1-C_6)$alkyl-Y'—$(C_1-C_6)$alkyl- group; or the two $R^4$ groups together form a —$(C_3-C_5)$alkyl- group, a —$(C_2-C_6)$alkyl-Y—$(C_2-C_6)$alkyl group or a —$(C_1-C_6)$alkyl-Y'—$(C_1-C_6)$alkyl- group and the two $R^1$ groups together form a —$(C_3-C_8)$alkyl- group, a —$(C_2-C_6)$alkyl-Y—$(C_2-C_6)$alkyl- group or a —$(C_1-C_6)$alkyl-Y'—$(C_1-C_6)$alkyl- group;

the dashed bonds labeled "a" are absent and the dashed bonds labeled "b" are double bonds; or all the dashed bonds are single bonds;

$R^2$ is H, $(C_1-C_6)$alkyl or aryl, wherein aryl is optionally substituted with one or more $Z^1$ groups;

$R^3$ is H, $(C_1-C_6)$alkyl or aryl, wherein aryl is optionally substituted with one or more $Z^1$ groups;

Y is O, S, NH, $NR_c$, P, P(=O) or POH;

Y' is $Si(R_b)_2$ or —$Si(R_b)_2$—O—$Si(R_b)_2$—;

each $R_a$ is independently $(C_1-C_6)$alkyl, $(C_3-C_7)$carbocycle or aryl, wherein aryl is optionally substituted with one or more $Z^1$ groups;

each $R_b$ is independently $(C_1-C_6)$alkyl, $(C_3-C_7)$carbocycle or aryl, wherein aryl is optionally substituted with one or more $Z^1$ groups;

each $R_c$ is independently $R_g$ or a $C_1-C_{18}$ saturated or unsaturated carbon chain that is optionally substituted with one or more groups independently selected from oxo (=O), hydroxy, mercapto, $(C_1-C_6)$alkoxy, $(C_1-C_6)$alkanoyloxy, $NR_dR_e$, carboxy, and aryl, wherein any aryl of $R_e$ is optionally substituted with one or more $R_f$;

each $R_d$ and $R_e$ is independently selected from H, $(C_1-C_6)$alkyl, $(C_1-C_6)$alkanoyl, phenyl, benzyl, and $R_g$;

each $R_f$ is independently selected from $(C_1-C_6)$alkyl, $(C_1-C_6)$alkoxy, $(C_1-C_6)$alkoxycarbonyl, $(C_1-C_6)$alkanoyloxy, —C(=O)-phenyl, and —C(=O)CH$_2$C(=O)-phenyl, wherein any phenyl is optionally substituted with one or more groups independently selected from $(C_1-C_6)$alkyl, —SO$_3$H, and $(C_1-C_6)$alkoxy;

each $R_g$ is

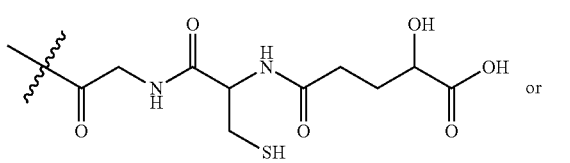 or each $Z^1$ is independently selected from $(C_1-C_6)$alkyl, halogen, —CN, —$OR_{n1}$, —$NR_{q1}R_{r1}$, —$NR_{n1}COR_{p1}$, —$NR_{n1}CO_2R_{p1}$, NO$_2$, —$C(O)R_{n1}$, —$C(O)OR_{n1}$ and —$C(O)NR_{q1}R_{r1}$, wherein any $(C_1-C_6)$alkyl of $Z^1$ is optionally substituted with one or more (e.g. 1, 2, 3, 4, 5 or 6) halogen;

each $R_{n1}$ is independently selected from H and $(C_1-C_6)$alkyl, wherein any $(C_1-C_6)$alkyl of $R_{n1}$ is optionally substituted with one or more (e.g. 1, 2, 3, 4, 5 or 6) halogen;

each $R_{p1}$ is independently $(C_1-C_6)$alkyl and $R_{q1}$ and $R_{r1}$ are each independently selected from H and $(C_1-C_6)$alkyl or $R_q$ and $R_{r1}$ together with the nitrogen to which they are attached form a piperidine, pyrrolidine, morpholine, azetidine, thiomorpholine, piperazine or 4-methylpiperazine;

or a salt thereof.

6. The method of claim 5 wherein the wherein the sunless tanning composition comprises a compound of formula I selected from:

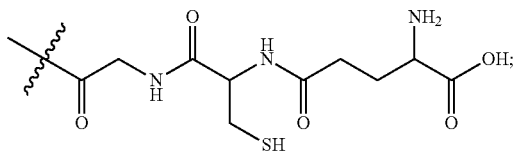

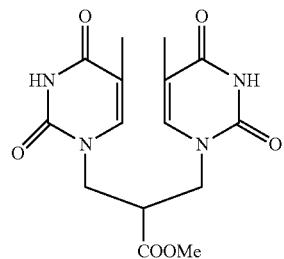

115

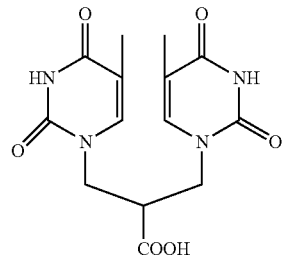

116

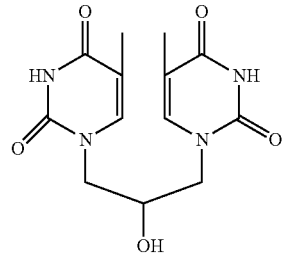

121

122
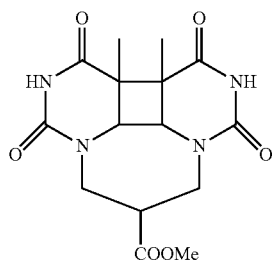
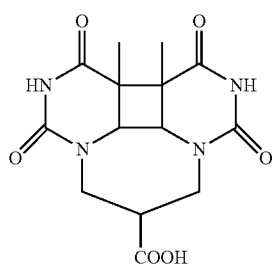
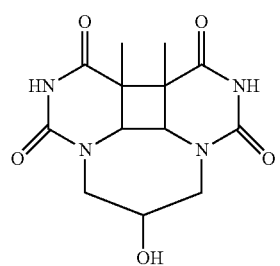
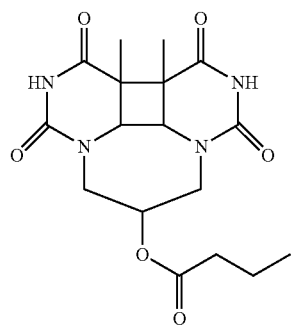
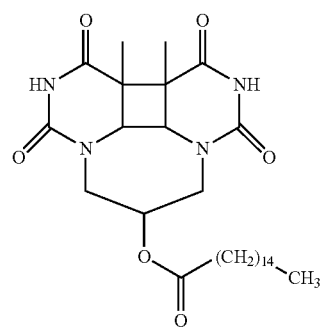
130
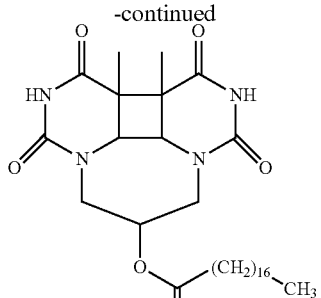
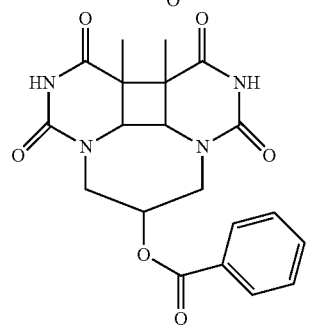
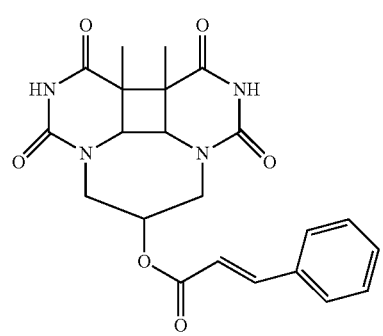
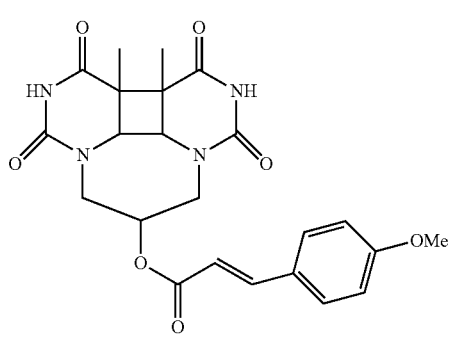
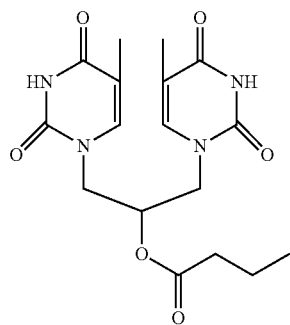

69
-continued
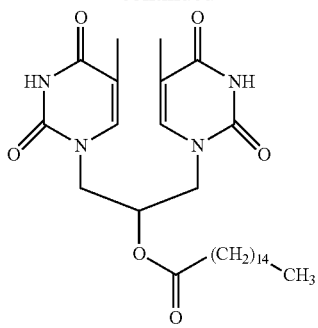
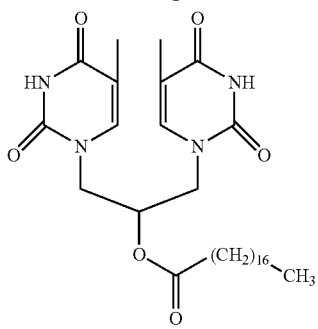
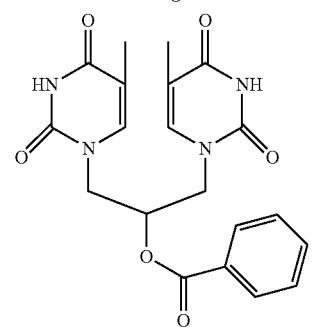
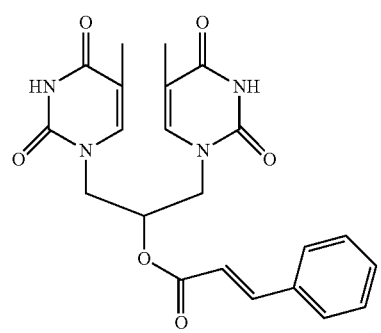
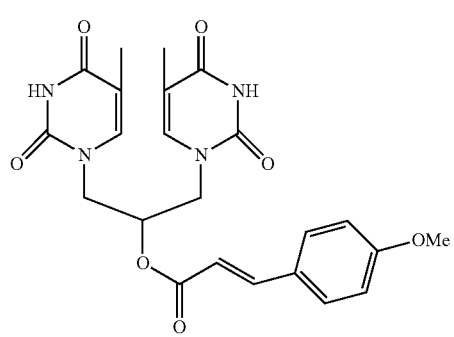
70
-continued
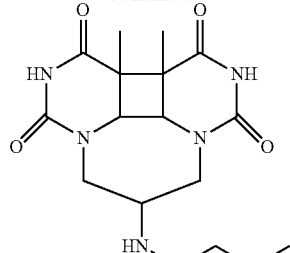
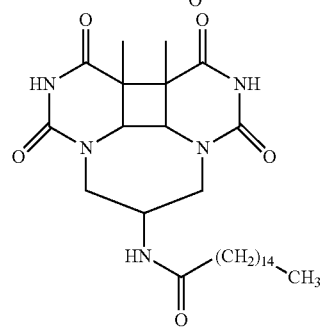
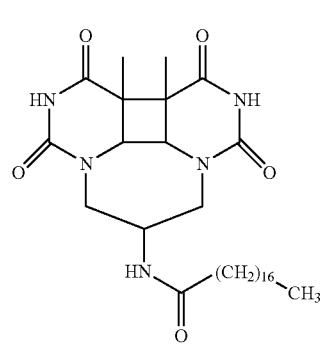
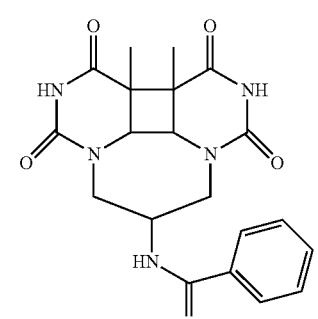
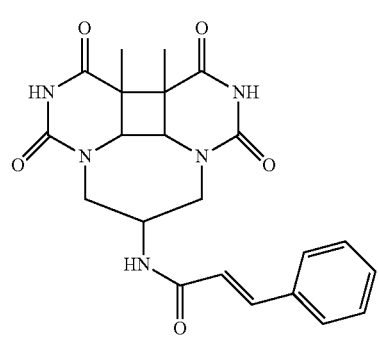

71
-continued
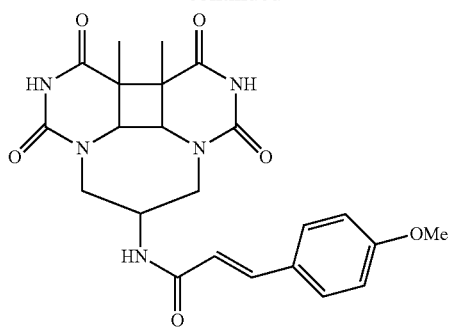
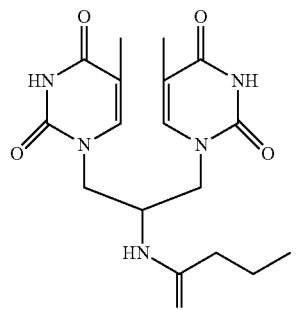
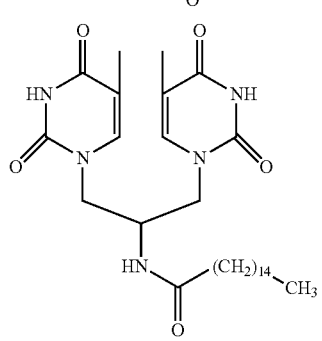
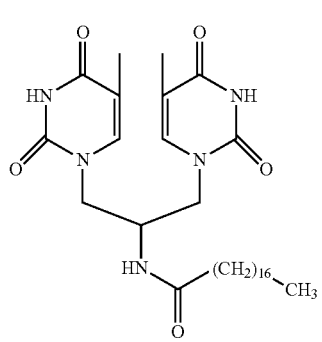
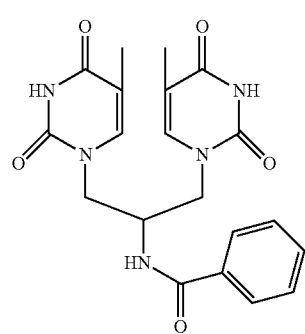
72
-continued
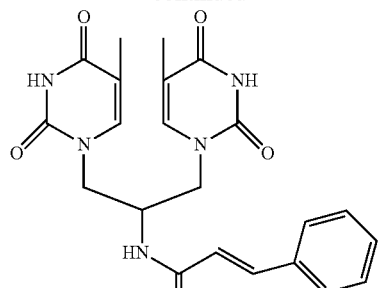
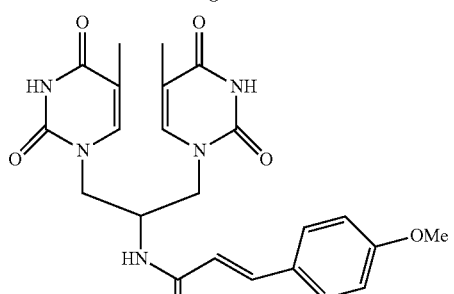
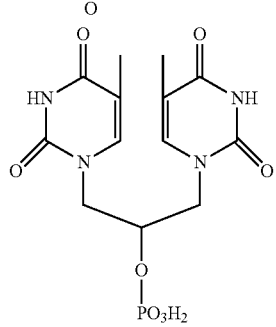
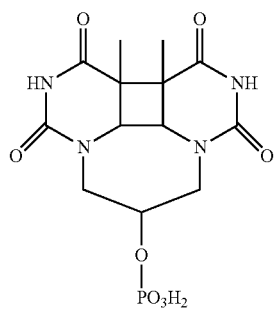
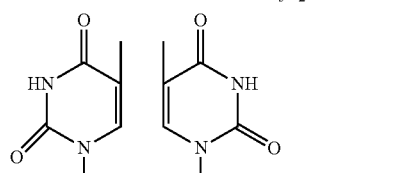
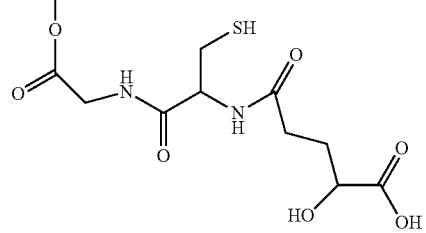

-continued
and

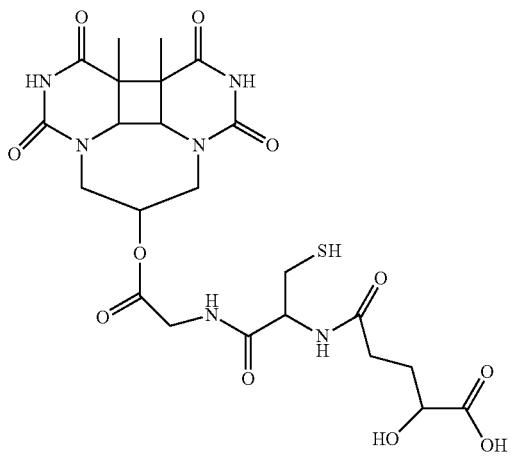

or a salt thereof.

7. A method of stimulating pigmentation in mammalian skin, comprising administering to mammalian skin in need thereof, an effective amount of a sunless tanning composition comprising a compound of formula I:

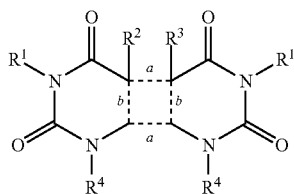

wherein:
each $R^1$ is independently H, $(C_1\text{-}C_6)$alkyl, $(C_3\text{-}C_7)$carbocycle or $R_aC(=O)-$, and the two $R^4$ groups together form a $-(C_3\text{-}C_8)$alkyl- group, a $-(C_2\text{-}C_6)$alkyl-Y-$(C_2\text{-}C_6)$alkyl- group or a $-(C_1\text{-}C_6)$alkyl-Y'-$(C_1\text{-}C_6)$alkyl- group; or
each $R^4$ is independently H, $(C_1\text{-}C_6)$alkyl, $(C_3\text{-}C_7)$carbocycle or $R_aC(=O)-$, and the two $R^1$ groups together form a $-(C_3\text{-}C_8)$alkyl- group, a $-(C_2\text{-}C_6)$alkyl-Y-$(C_2\text{-}C_6)$alkyl- group or a $-(C_1\text{-}C_6)$alkyl-Y'-$(C_1\text{-}C_6)$alkyl- group; or
the two $R^4$ groups together form a $-(C_3\text{-}C_8)$alkyl- group, a $-(C_2\text{-}C_6)$alkyl-Y-$(C_2\text{-}C_6)$alkyl group or a $-(C_1\text{-}C_6)$alkyl-Y'-$(C_1\text{-}C_6)$alkyl- group and the two $R^1$ groups together form a $-(C_3\text{-}C_8)$alkyl- group, a $-(C_2\text{-}C_6)$alkyl-Y-$(C_2\text{-}C_6)$alkyl- group or a $-(C_1\text{-}C_6)$alkyl-Y'-$(C_1\text{-}C_6)$alkyl- group;
the dashed bonds labeled "a" are absent and the dashed bonds labeled "b" are double bonds; or all the dashed bonds are single bonds;
$R^2$ is H, $(C_1\text{-}C_6)$alkyl or aryl, wherein aryl is optionally substituted with one or more $Z^1$ groups;
$R^3$ is H, $(C_1\text{-}C_6)$alkyl or aryl, wherein aryl is optionally substituted with one or more $Z^1$ groups;
Y is O, S, NH, $NR_c$, P, P(=O) or POH;
Y' is $Si(R_b)_2$ or $-Si(R_b)_2-O-Si(R_b)_2-$;
each $R_a$ is independently $(C_1\text{-}C_6)$alkyl, $(C_3\text{-}C_7)$carbocycle or aryl, wherein aryl is optionally substituted with one or more $Z^1$ groups;
each $R_b$ is independently $(C_1\text{-}C_6)$alkyl, $(C_3\text{-}C_7)$carbocycle or aryl, wherein aryl is optionally substituted with one or more $Z^1$ groups;
each $R_c$ is independently $R_g$ or a $C_1\text{-}C_{18}$ saturated or unsaturated carbon chain that is optionally substituted with one or more groups independently selected from oxo (=O), hydroxy, mercapto, $(C_1\text{-}C_6)$alkoxy, $(C_1\text{-}C_6)$alkoxycarbonyl, $(C_1\text{-}C_6)$alkanoyloxy, $NR_dR_e$, carboxy, and aryl, wherein any aryl of $R_c$ is optionally substituted with one or more $R_f$;
each $R_d$ and $R_e$ is independently selected from H, $(C_1\text{-}C_6)$alkyl, $(C_1\text{-}C_6)$alkanoyl, phenyl, benzyl, and $R_g$;
each $R_f$ is independently selected from $(C_1\text{-}C_6)$alkyl, $(C_1\text{-}C_6)$alkoxy, $(C_1\text{-}C_6)$alkoxycarbonyl, $(C_1\text{-}C_6)$alkanoyloxy, $-C(=O)$-phenyl, and $-C(=O)CH_2C(=O)$-phenyl, wherein any phenyl is optionally substituted with one or more groups independently selected from $(C_1\text{-}C_6)$alkyl, $-SO_3H$, and $(C_1\text{-}C_6)$alkoxy;
each $R_g$ is

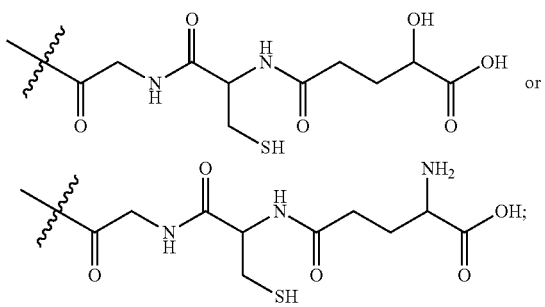

each $Z^1$ is independently selected from $(C_1\text{-}C_6)$alkyl, halogen, $-CN$, $-OR_{n1}$, $-NR_{q1}R_{r1}$, $-NR_{n1}COR_{p1}$, $-NR_{n1}CO_2R_{p1}$, $NO_2$, $-C(O)R_{n1}$, $-C(O)OR_{n1}$ and $-C(O)NR_{q1}R_{r1}$, wherein any $(C_1\text{-}C_6)$alkyl of $Z^1$ is optionally substituted with one or more (e.g. 1, 2, 3, 4, 5 or 6) halogen;
each $R_{n1}$ is independently selected from H and $(C_1\text{-}C_6)$alkyl, wherein any $(C_1\text{-}C_6)$alkyl of $R_{n1}$ is optionally substituted with one or more (e.g. 1, 2, 3, 4, 5 or 6) halogen;
each $R_1$ is independently $(C_1\text{-}C_6)$alkyl; and
$R_{q1}$ and $R_{r1}$ are each independently selected from H and $(C_1\text{-}C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine;
or a salt thereof.

8. The method of claim 7 wherein the wherein the sunless tanning composition comprises a compound of formula I selected from:

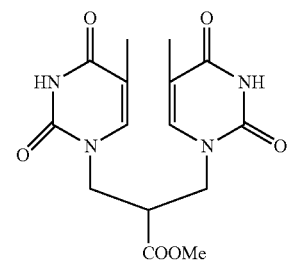

75
-continued
116
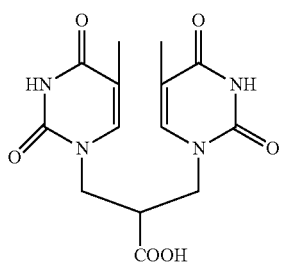
121
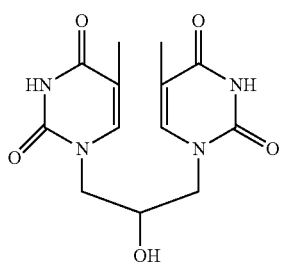
122
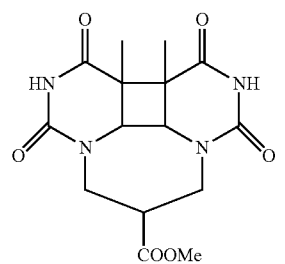
130
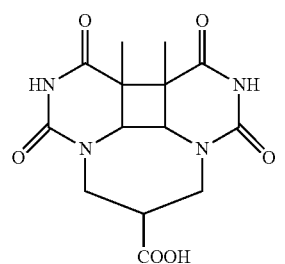
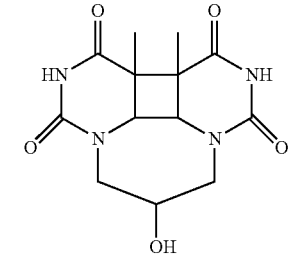
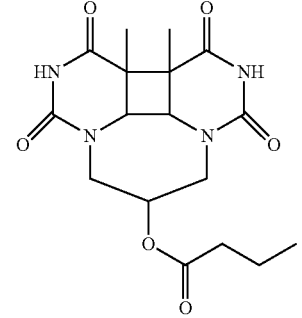
76
-continued
5
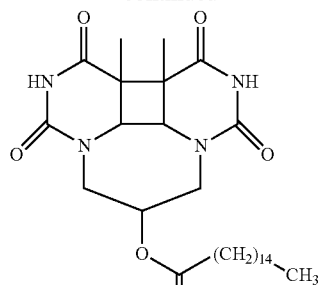
15
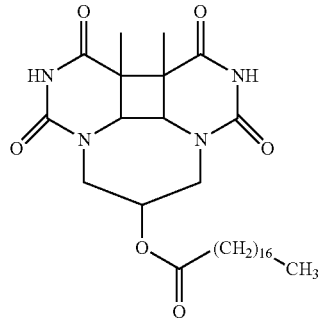
25
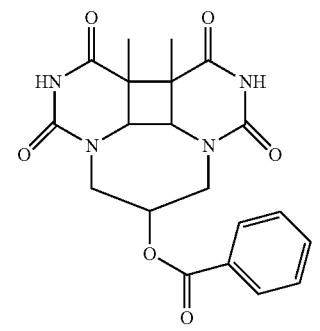
35
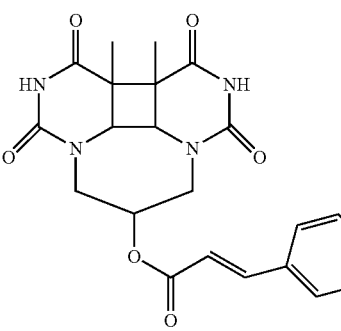
45
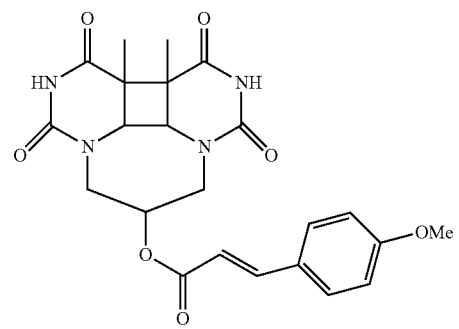

77
-continued
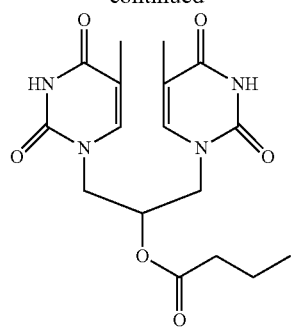
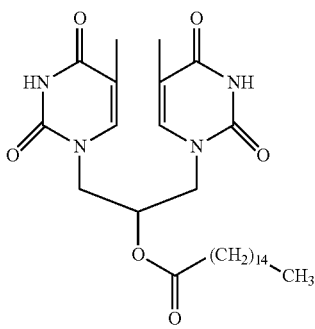
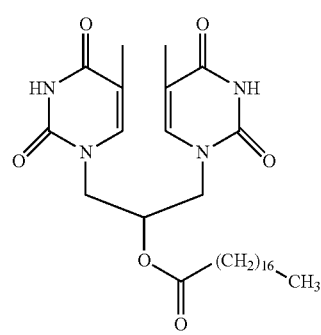
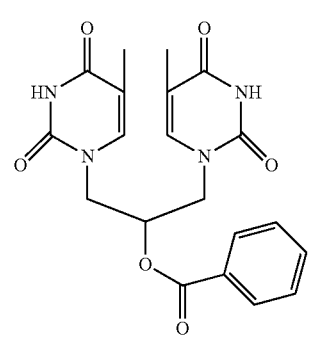
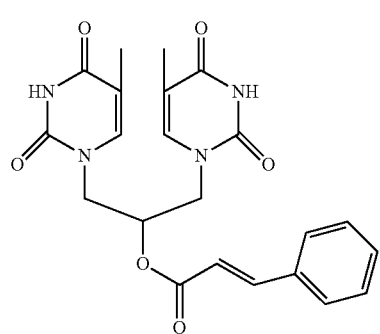
78
-continued
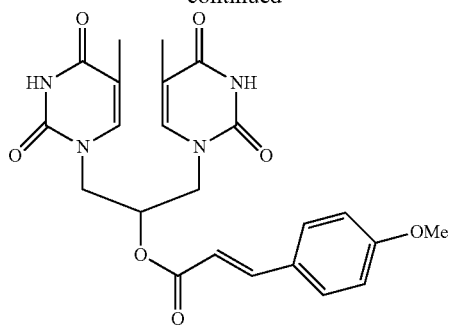
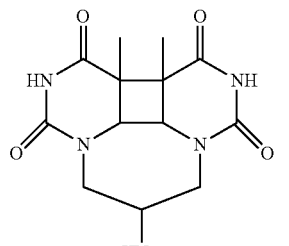
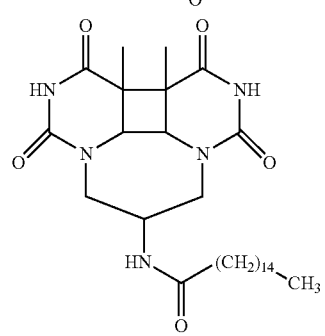
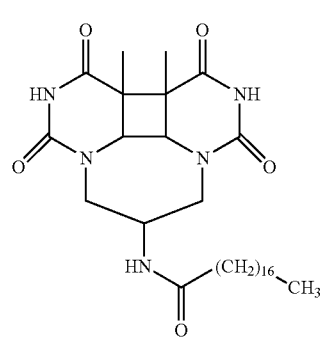
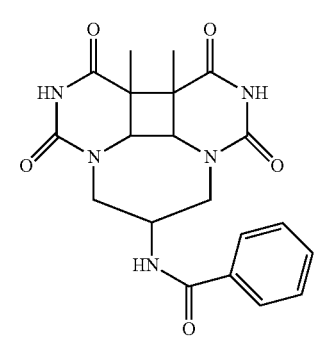

79
-continued
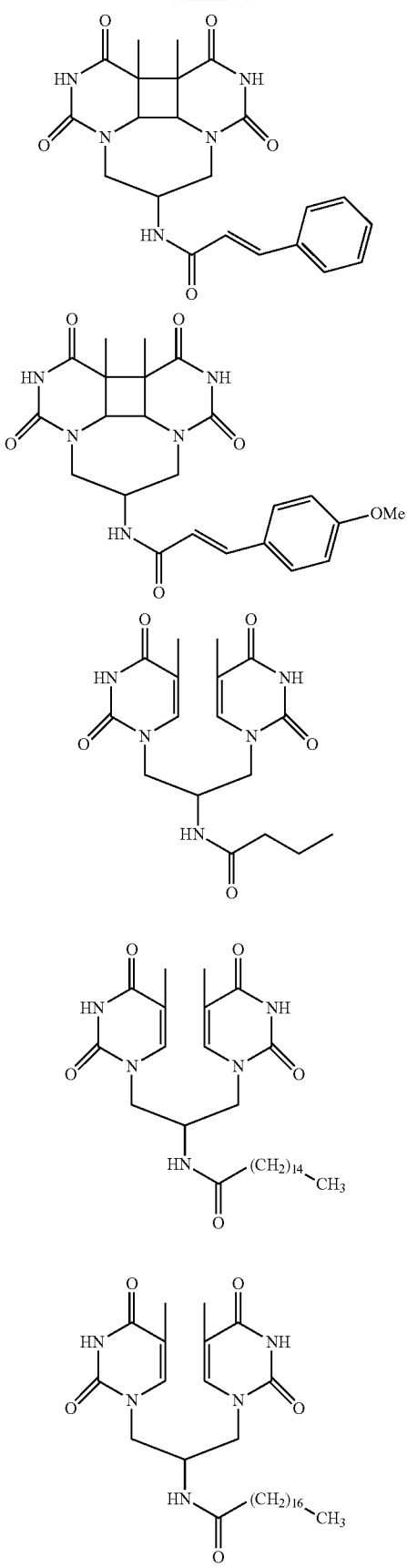
80
-continued
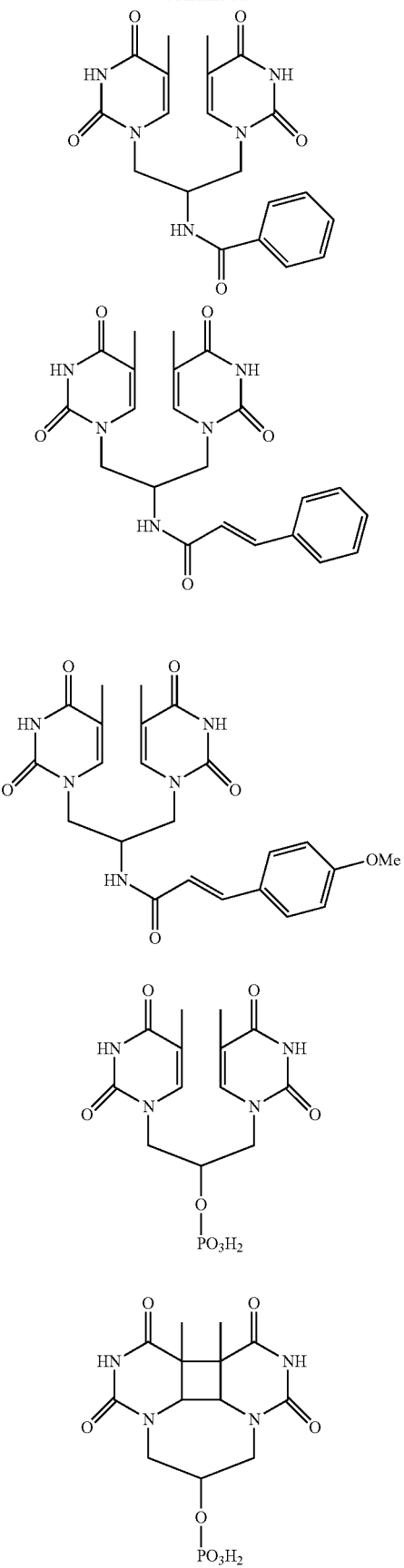

-continued

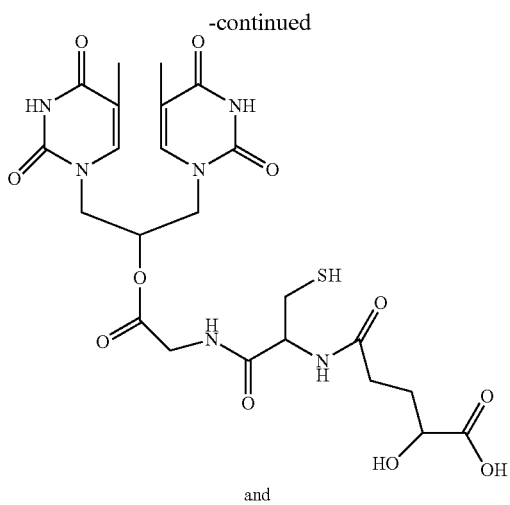

and

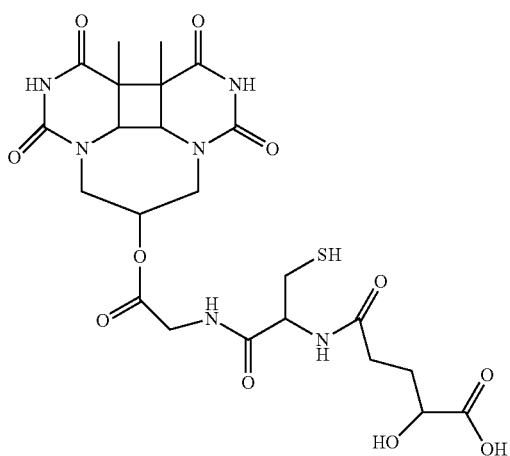

or a salt thereof.

9. A method of stimulating the production of melanin in melanocytes in skin of a mammal, comprising administering to mammalian skin in need thereof, an effective amount of a sunless tanning composition comprising a compound of formula I:

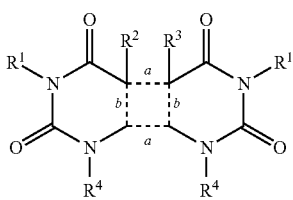

I wherein:
each $R^1$ is independently H, $(C_1-C_6)$alkyl, $(C_3-C_7)$carbocycle or $R_aC(=O)—$, and the two $R^4$ groups together form a $—(C_3-C_5)$alkyl- group, a $—(C_2-C_6)$alkyl-Y—$(C_2-C_6)$alkyl- group or a $—(C_1-C_6)$alkyl-Y'—$(C_1-C_6)$alkyl- group; or
each $R^4$ is independently H, $(C_1-C_6)$alkyl, $(C_3-C_7)$carbocycle or $R_aC(=O)—$, and the two $R^1$ groups together form a $—(C_3-C_5)$alkyl- group, a $—(C_2-C_6)$alkyl-Y—$(C_2-C_6)$alkyl- group or a $—(C_1-C_6)$alkyl-Y'—$(C_1-C_6)$alkyl- group; or the two $R^4$ groups together form a $—(C_3-C_5)$alkyl- group, a $—(C_2-C_6)$alkyl-Y—$(C_2-C_6)$alkyl group or a $—(C_1-C_6)$alkyl-Y'—$(C_1-C_6)$alkyl- group and the two $R^1$ groups together form a $—(C_3-C_8)$alkyl- group, a $—(C_2-C_6)$alkyl-Y—$(C_2-C_6)$alkyl- group or a $—(C_1-C_6)$alkyl-Y'—$(C_1-C_6)$alkyl- group;

the dashed bonds labeled "a" are absent and the dashed bonds labeled "b" are double bonds; or all the dashed bonds are single bonds;

$R^2$ is H, $(C_1-C_6)$alkyl or aryl, wherein aryl is optionally substituted with one or more $Z^1$ groups;

$R^3$ is H, $(C_1-C_6)$alkyl or aryl, wherein aryl is optionally substituted with one or more $Z^1$ groups;

Y is O, S, NH, $NR_c$, P, P(=O) or POH;

Y' is $Si(R_b)_2$ or $—Si(R_b)_2—O—Si(R_b)_2—$;

each $R_a$ is independently $(C_1-C_6)$alkyl, $(C_3-C_7)$carbocycle or aryl, wherein aryl is optionally substituted with one or more $Z^1$ groups;

each $R_b$ is independently $(C_1-C_6)$alkyl, $(C_3-C_7)$carbocycle or aryl, wherein aryl is optionally substituted with one or more $Z^1$ groups;

each $R_c$ is independently $R_g$ or a $C_1-C_{18}$ saturated or unsaturated carbon chain that is optionally substituted with one or more groups independently selected from oxo (=O), hydroxy, mercapto, $(C_1-C_6)$alkoxy, $(C_1-C_6)$alkoxycarbonyl, $(C_1-C_6)$alkanoyloxy, $NR_dR_e$, carboxy, and aryl, wherein any aryl of $R_e$ is optionally substituted with one or more $R_f$;

each $R_d$ and $R_e$ is independently selected from H, $(C_1-C_6)$alkyl, $(C_1-C_6)$alkanoyl, phenyl, benzyl, and $R_g$;

each $R_f$ is independently selected from $(C_1-C_6)$alkyl, $(C_1-C_6)$alkoxy, $(C_1-C_6)$alkoxycarbonyl, $(C_1-C_6)$alkanoyloxy, $—C(=O)$-phenyl, and $—C(=O)CH_2C(=O)$-phenyl, wherein any phenyl is optionally substituted with one or more groups independently selected from $(C_1-C_6)$alkyl, $—SO_3H$, and $(C_1-C_6)$alkoxy:

each $R_g$ is

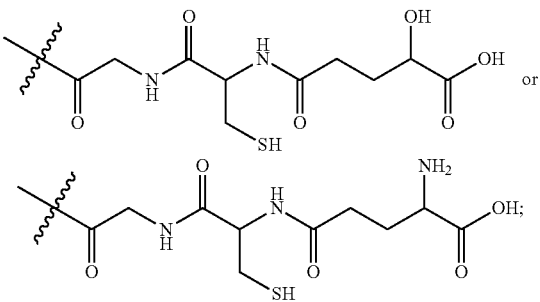

each $Z^1$ is independently selected from $(C_1-C_6)$alkyl, halogen, $—CN$, $—OR_{n1}$, $—NR_{q1}R_{r1}$, $—NR_{n1}COR_{p1}$, $—NR_{n1}CO_2R_{p1}$, $NO_2$, $—C(O)R_{n1}$, $—C(O)OR_{n1}$ and $—C(O)NR_{q1}R_{r1}$, wherein any $(C_1-C_6)$alkyl of $Z^1$ is optionally substituted with one or more (e.g. 1, 2, 3, 4, 5 or 6) halogen;

each $R_{n1}$ is independently selected from H and $(C_1-C_6)$alkyl, wherein any $(C_1-C_6)$alkyl of $R_{n1}$ is optionally substituted with one or more (e.g. 1, 2, 3, 4, 5 or 6) halogen;

each $R_{p1}$ is independently $(C_1-C_6)$alkyl; and $R_{q1}$ and $R_{r1}$ are each independently selected from H and $(C_1-C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine;
or a salt thereof.
10. The method of claim 9 wherein the wherein the sunless tanning composition comprises a compound of formula I selected from:
115
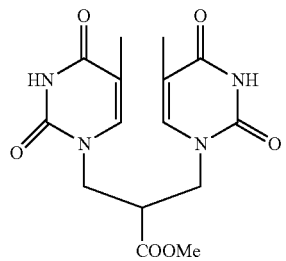
116
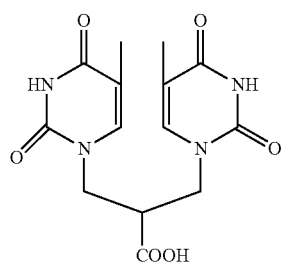
121
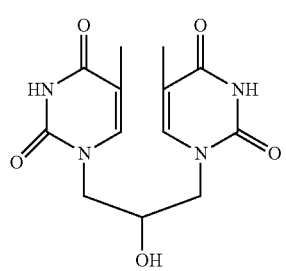
122
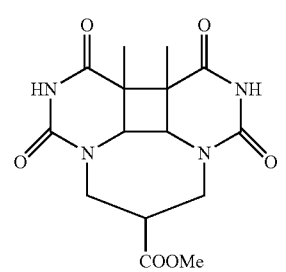
130
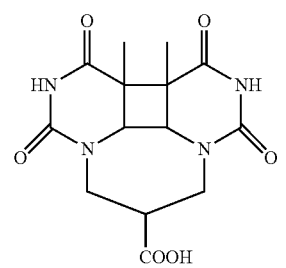
-continued
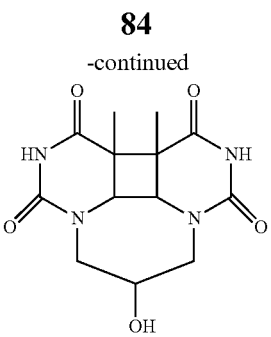
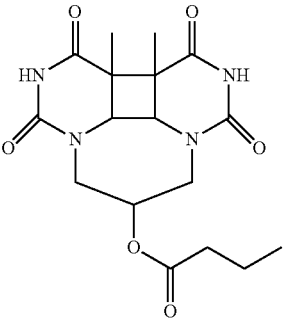
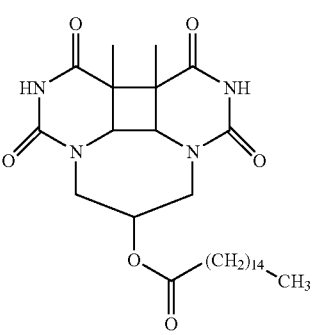
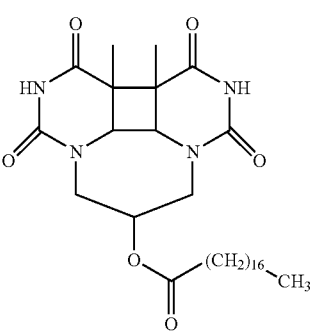
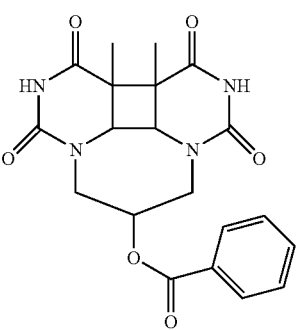

85
-continued
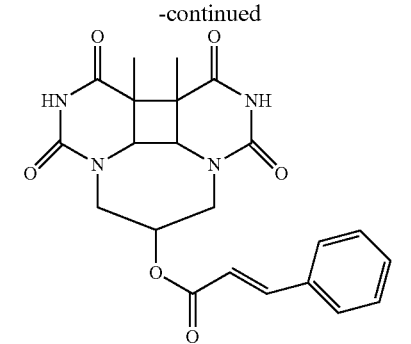
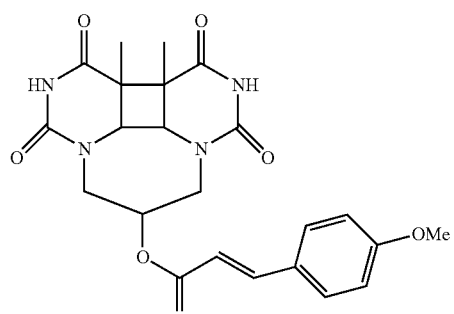
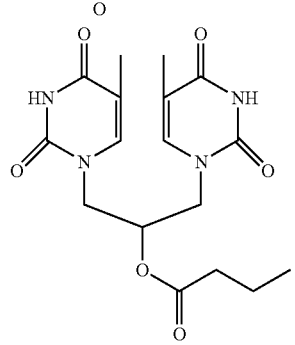
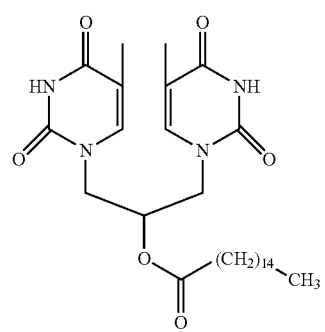
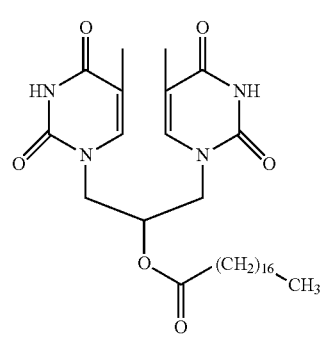
86
-continued
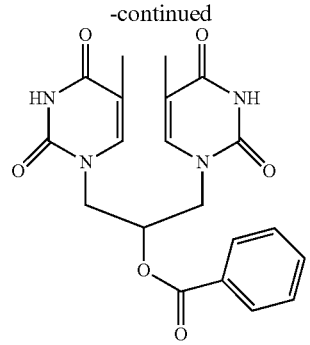
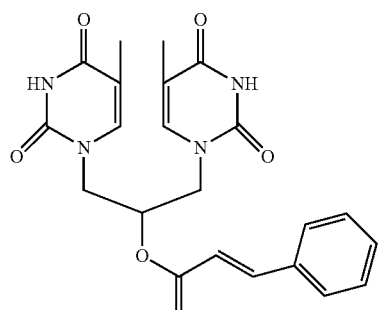
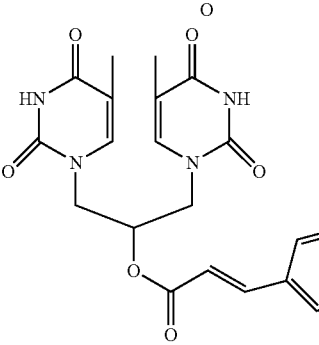
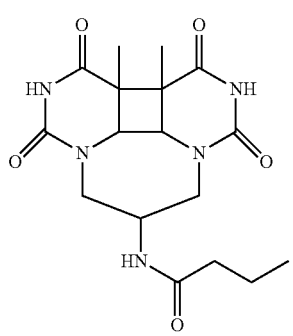
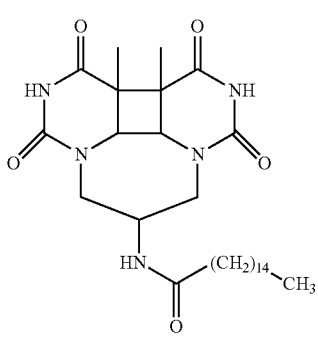

87
-continued
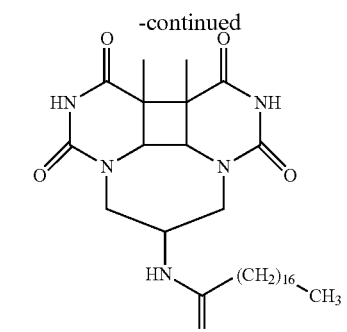
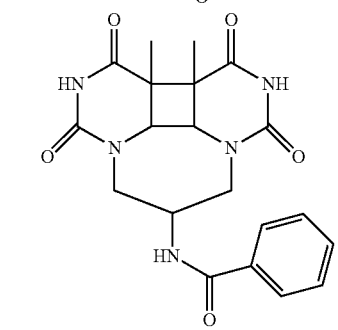
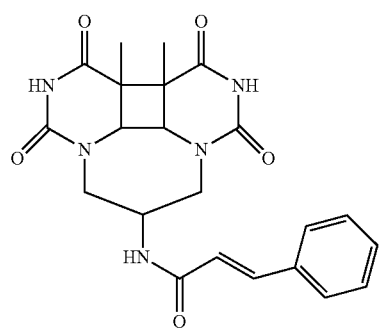
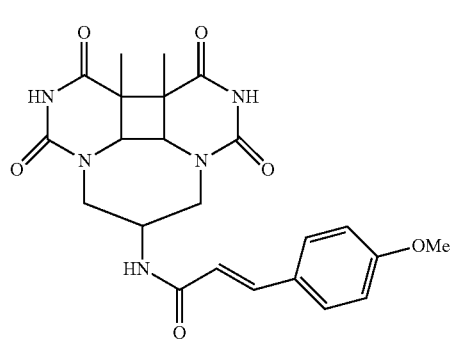
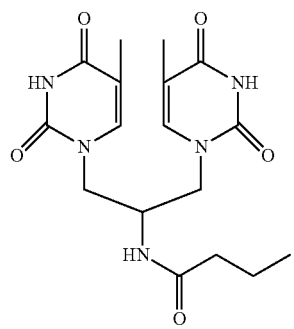
88
-continued
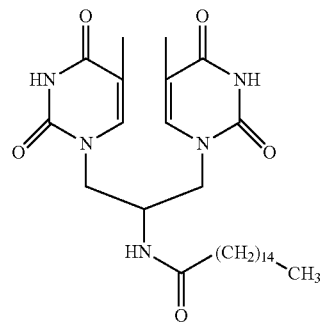
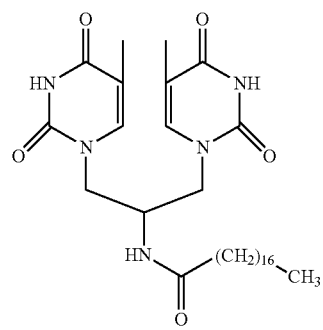
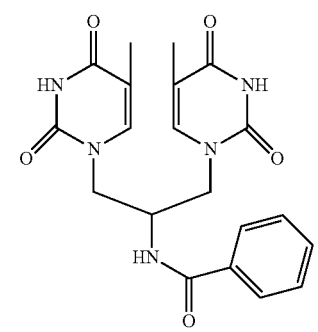
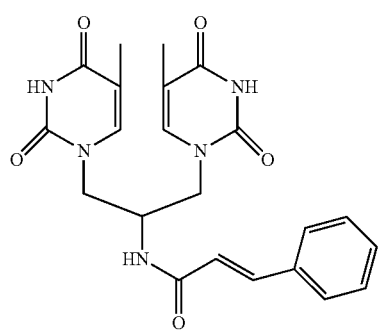

89
-continued
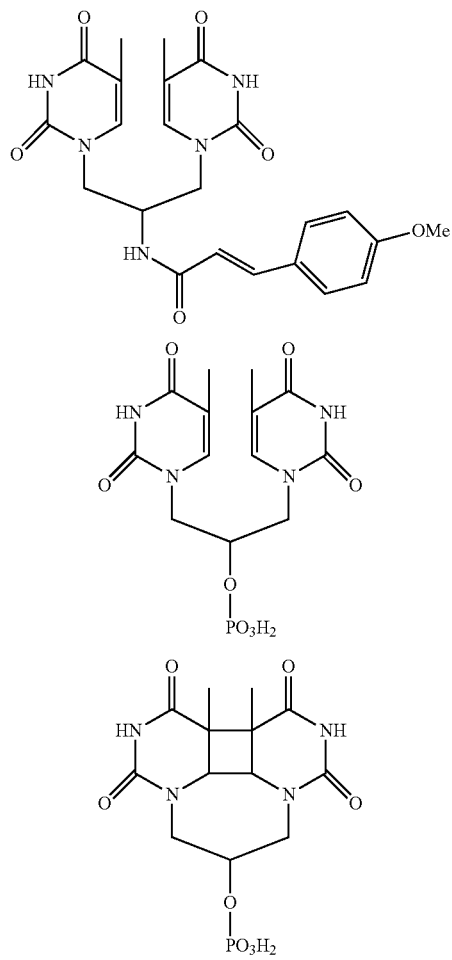
90
-continued
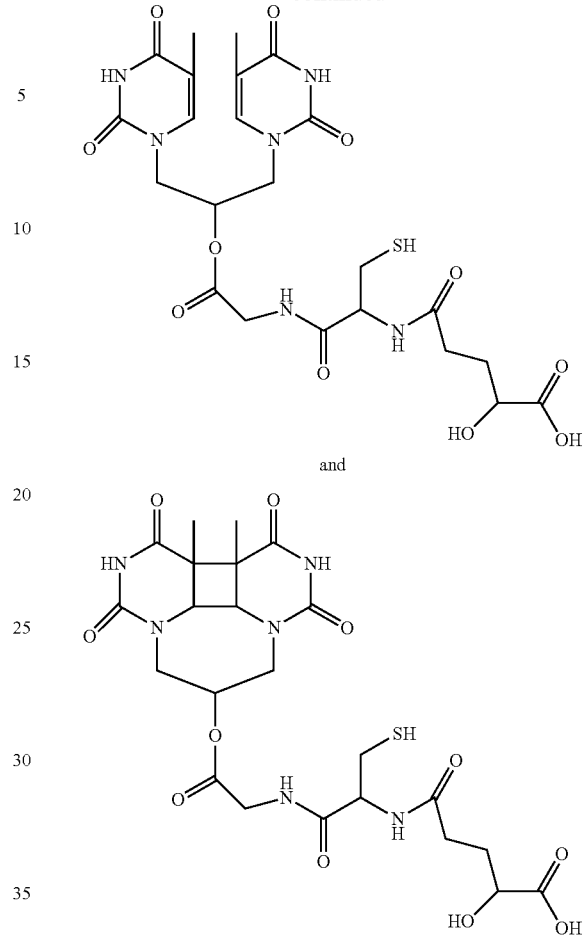
or a salt thereof.
* * * * *

UNITED STATES PATENT AND TRADEMARK OFFICE
CERTIFICATE OF CORRECTION

PATENT NO. : 9,987,211 B2
APPLICATION NO. : 14/901979
DATED : June 5, 2018
INVENTOR(S) : Robert Vince, Abbas Raza and Christine Dreis It is certified that error appears in the above-identified patent and that said Letters Patent is hereby corrected as shown below:

In the Claims

Column 56, Line 57, Claim 3, please delete "$(C_3-C_5)$alkyl" and insert -- $(C_3-C_8)$alkyl --;

Column 56, Line 62, Claim 3, please delete "$(C_3-C_5)$alkyl" and insert -- $(C_3-C_8)$alkyl --;

Column 56, Line 65, Claim 3, please delete "$(C_3-C_5)$alkyl" and insert -- $(C_3-C_8)$alkyl --;

Column 57, Line 27, Claim 3, please delete "and R;" and insert -- and $R_g$; --;

Column 65, Line 14, Claim 5, please delete "$(C_3-C_5)$alkyl" and insert -- $(C_3-C_8)$alkyl --;

Column 65, Line 19, Claim 5, please delete "$(C_3-C_5)$alkyl" and insert -- $(C_3-C_8)$alkyl --;

Column 65, Line 22, Claim 5, please delete "$(C_3-C_5)$alkyl" and insert -- $(C_3-C_8)$alkyl --;

Column 65, Line 48, Claim 5, please delete "of $R_e$ is" and insert -- of $R_c$ is --;

Column 66, Line 23, Claim 5, please delete "or $R_q$ and" and insert -- or $R_{q1}$ and --;

Column 74, Line 44, Claim 7, please delete "each $R_1$ is" and insert -- each $R_{p1}$ --;

Column 81, Line 60, Claim 9, please delete "$(C_3-C_5)$alkyl" and insert -- $(C_3-C_8)$alkyl --;

Column 81, Line 65, Claim 9, please delete "$(C_3-C_5)$alkyl" and insert -- $(C_3-C_8)$alkyl --;

Column 82, Line 1, Claim 9, please delete "$(C_3-C_5)$alkyl" and insert -- $(C_3-C_8)$alkyl --;

Column 82, Line 27, Claim 9, please delete "of $R_e$ is" and insert -- of $R_c$ is -- therefor.

Signed and Sealed this
Thirty-first Day of July, 2018

Andrei Iancu
*Director of the United States Patent and Trademark Office*